(12) United States Patent
Yoshioka et al.

(10) Patent No.: US 10,559,763 B2
(45) Date of Patent: Feb. 11, 2020

(54) PHOTOELECTRIC CONVERSION ELEMENT, IMAGING DEVICE, OPTICAL SENSOR, AND METHOD OF USING PHOTOELECTRIC CONVERSION ELEMENT

(71) Applicant: FUJIFILM Corporation, Tokyo (JP)

(72) Inventors: Tomoaki Yoshioka, Kanagawa (JP); Masaaki Tsukase, Kanagawa (JP); Takahiko Ichiki, Kanagawa (JP); Daigo Sawaki, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/186,373

(22) Filed: Nov. 9, 2018

(65) Prior Publication Data

US 2019/0081250 A1    Mar. 14, 2019

Related U.S. Application Data

(60) Division of application No. 14/863,962, filed on Sep. 24, 2015, now Pat. No. 10,177,320, which is a
(Continued)

(30) Foreign Application Priority Data

Mar. 28, 2013  (JP) ................................ 2013-069206
Aug. 22, 2013  (JP) ................................ 2013-172087

(51) Int. Cl.
*C07D 471/04* (2006.01)
*C07D 519/00* (2006.01)
(Continued)

(52) U.S. Cl.
CPC ........ *H01L 51/0073* (2013.01); *C07D 209/86* (2013.01); *C07D 471/04* (2013.01);
(Continued)

(58) Field of Classification Search
CPC ............ H01L 51/0073; H01L 51/0046; H01L 51/0053; H01L 51/0072; H01L 51/0071;
(Continued)

(56) References Cited

U.S. PATENT DOCUMENTS

2006/0044561 A1    3/2006  Nii
2009/0223566 A1    9/2009  Mitsui et al.
(Continued)

FOREIGN PATENT DOCUMENTS

JP    2004-010736 A    1/2004
JP    2006-100767 A    4/2006
(Continued)

OTHER PUBLICATIONS

International Search Report of PCT/JP2014/056870 dated May 19, 2014.
(Continued)

*Primary Examiner* — Susan D Leong
(74) *Attorney, Agent, or Firm* — Studebaker & Brackett PC

(57) ABSTRACT

The present invention provides a photoelectric conversion element having a photoelectric conversion film which exhibits excellent photoelectric conversion efficiency and responsiveness, an imaging device, an optical sensor, and a method of using a photoelectric conversion element. In the photoelectric conversion element of the invention, a photoelectric conversion material contains at least one selected from the group consisting of a compound represented by General formula (1), a compound represented by General formula (2), and a compound represented by General formula (3).
(Continued)

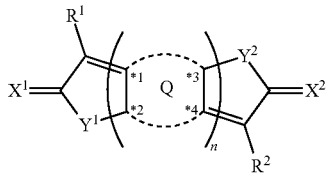

General formula (1)

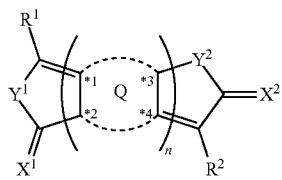

General formula (2)

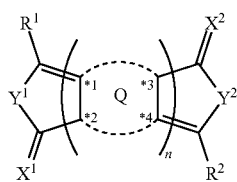

General formula (3)

3 Claims, 2 Drawing Sheets

Related U.S. Application Data continuation of application No. PCT/JP2014/056870, filed on Mar. 14, 2014.

(51) Int. Cl.

| | | |
|---|---|---|
| *C07D 209/86* | (2006.01) | |
| *C07D 493/04* | (2006.01) | |
| *C07D 495/04* | (2006.01) | |
| *H01L 51/00* | (2006.01) | |
| *H01L 27/30* | (2006.01) | |
| *H01L 51/42* | (2006.01) | |

(52) U.S. Cl.
CPC ......... *C07D 493/04* (2013.01); *C07D 495/04* (2013.01); *C07D 519/00* (2013.01); *H01L 27/305* (2013.01); *H01L 27/307* (2013.01); *H01L 51/006* (2013.01); *H01L 51/0046* (2013.01); *H01L 51/0058* (2013.01); *H01L 51/0061* (2013.01); *H01L 51/0067* (2013.01); *H01L 51/0071* (2013.01); *H01L 51/0072* (2013.01); *H01L 51/0053* (2013.01); *H01L 51/4273* (2013.01)

(58) Field of Classification Search
CPC ............... H01L 51/0061; H01L 51/006; H01L 51/0058; C07D 209/86; C07D 471/04; C07D 493/04; C07D 494/04; C07D 519/00
See application file for complete search history.

(56) References Cited

U.S. PATENT DOCUMENTS

| | | |
|---|---|---|
| 2013/0015435 A1 | 1/2013 | Sawaki et al. |
| 2013/0181202 A1 | 7/2013 | Yofu et al. |

FOREIGN PATENT DOCUMENTS

| | | | |
|---|---|---|---|
| JP | 2007-258235 A | 10/2007 | |
| JP | 2010-103457 A | 5/2010 | |
| JP | 2011-222949 A | 11/2011 | |
| JP | 2012-077064 A | 4/2012 | |
| WO | 2007003520 A1 | 1/2007 | |
| WO | 2013013765 A1 | 1/2013 | |

OTHER PUBLICATIONS

Translation of the International Preliminary Report on Patentability of PCT/JP2014/056870 dated Oct. 8, 2015.
An Office Action; "Notification of Reasons for Refusal," issued by the Japanese Patent Office dated Apr. 5, 2016, which corresponds to Japanese Patent Application No. 2014-051959 and is related to U.S. Appl. No. 14/863,962; with English language translation.
An Office Action; "Notification of Reasons for Refusal," issued by the Korean Patent Office dated Jan. 16, 2017, which corresponds to Korean Patent Application No. 10-2015-7026454 and is related to U.S. Appl. No. 14/863,962; with English language translation.

«PHOTOELECTRIC CONVERSION ELEMENT, IMAGING DEVICE, OPTICAL SENSOR, AND METHOD OF USING PHOTOELECTRIC CONVERSION ELEMENT»

PHOTOELECTRIC CONVERSION ELEMENT, IMAGING DEVICE, OPTICAL SENSOR, AND METHOD OF USING PHOTOELECTRIC CONVERSION ELEMENT

CROSS-REFERENCE TO RELATED APPLICATIONS

This application is a Divisional Application of Ser. No. 14/863,962 filed Sep. 24, 2015 which is a Continuation of PCT International Application No. PCT/JP2014/056870 filed on Mar. 14, 2014, which claims priority under 35 U.S.C. § 119(a) to Japanese Patent Application No. 2013-069206 filed on Mar. 28, 2013 and Japanese Patent Application No. 2013-172087 filed on Aug. 22, 2013. Each of the above applications is hereby expressly incorporated by reference, in its entirety, into the present application.

BACKGROUND OF THE INVENTION

The present invention relates to a photoelectric conversion element, an imaging device, an optical sensor, and a method of using a photoelectric conversion element.

A conventional optical sensor is an element in which a photodiode (PD) is formed in a semiconductor substrate such as silicon (Si), and as a solid-state imaging device, a planar solid-state imaging device, in which PDs are two-dimensionally arranged and signal charge generated by each PD is read out by a circuit, is widely used.

In order to obtain a color solid-state imaging device, a structure in which color filters that transmit light of a specific wavelength are arranged in a light incident surface of the planar solid-state imaging device is generally used. Currently, a single plate solid-state imaging device, in which color filters that transmit blue (B) light, green (G) light, and red (R) light are regularly arranged on each of the two-dimensionally arranged PDs, is well known and is widely used in a digital camera and the like.

In the single plate solid-state imaging device, the light not transmitted through the color filters is not utilized, and accordingly, light use efficiency is poor. Moreover, in recent years, the number of pixels has been increased, and the pixel size has been reduced. Consequentially, decrease in aperture ratio and decrease in light-collecting efficiency have become problems.

As a solution to the above problems, a structure obtained by forming a photoelectric conversion film formed of amorphous silicon on a substrate for reading out signal is known.

Regarding the photoelectric conversion element, imaging device, and optical sensor using a photoelectric conversion film, several examples of the prior art exist.

For example, JP 2006-100767 A discloses an imaging device using a photoelectric conversion film that uses a quinacridone-based compound.

SUMMARY OF THE INVENTION

In recent years, imaging devices, optical sensors, and the like have been required to be improved in terms of the performance, and accordingly, improvement of various characteristics, such as photoelectric conversion efficiency, responsiveness and the like, required for the photoelectric conversion element including the photoelectric conversion film used therein have also been required.

The inventors of the present invention prepared a photoelectric conversion film by using the compound (S-9) disclosed in the example section of JP 2006-100767 A. As a result, they found that in terms of photoelectric conversion efficiency and responsiveness, the photoelectric conversion element formed using the photoelectric conversion film does not reach a currently required level and needs to be further improved.

The present invention has been made in consideration of the aforementioned circumstances, and an object thereof is to provide a photoelectric conversion element which exhibits excellent photoelectric conversion efficiency and responsiveness.

Another object of the present invention is to provide an imaging device and an optical sensor each of which includes the photoelectric conversion element.

In order to achieve the aforementioned objects, the inventors of the present invention conducted intensive examination. As a result, the inventors obtained knowledge that by using a photoelectric conversion film containing a compound having a predetermined structure, the aforementioned objects can be achieved. Based on the knowledge, the inventors accomplished the present invention.

That is, the aforementioned objects can be achieved by the following means.

(1) A photoelectric conversion element in which a conductive film, a photoelectric conversion film containing a photoelectric conversion material, and a transparent conductive film are laminated in this order, wherein the photoelectric conversion material contains at least one compound selected from the group consisting of a compound represented by General formula (1) described below, a compound represented by General formula (2) described below, and a compound represented by General formula (3) described below.

(2) The photoelectric conversion element according to (1), wherein the photoelectric conversion material contains at least one compound selected from the group consisting of a compound represented by General formula (12) described below and a compound represented by General formula (13) described below.

(3) The photoelectric conversion element according to (1) or (2), wherein each of $R^1$ and $R^2$ in General formulae (1) to (3) represents an aryl group which may have a substituent or a heteroaryl group which may have a substituent.

(4) The photoelectric conversion element according to any one of (1) to (3), wherein at least one of $R^1$ and $R^2$ in General formulae (1) to (3) is a group represented by General formula (14) described below.

(5) The photoelectric conversion element according to (4), wherein in General formula (14), $R^{30}$ and $R^{31}$, $R^{30}$ and $R^{32}$, or $R^{31}$ and $R^{32}$ form a ring by being directly bonded to each other or by being bonded to each other through a linking group.

(6) The photoelectric conversion element according to any one of (1) to (5), wherein in General formulae (1) to (3), at least one of $R^1$ and $R^2$ is a group represented by General formula (18) described below.

(7) The photoelectric conversion element according to any one of (1) to (6), wherein in General formulae (1) to (3), at least one of $R^1$ and $R^2$ is a group represented by General formula (15) described below.

(8) The photoelectric conversion element according to any one of (1) to (7), wherein in General formulae (1) to (3), n=0.

(9) The photoelectric conversion element according to any one of (1) to (8), wherein in General formulae (1) to (3), $R^1$ and $R^2$ represent a same substituent.

(10) The photoelectric conversion element according to (6), wherein $R^1$ and $R^2$ both represent the group represented by General formula (18) described below, each of $X^1$ and $X^2$ represents an oxygen atom, each of $Y^1$ and $Y^2$ represents an oxygen atom, n=0, and $R^1$ and $R^2$ represent a same substituent.

(11) The photoelectric conversion element according to any one of (1) to (10), wherein the photoelectric conversion film further contains an n-type organic compound.

(12) The photoelectric conversion element according to (11), wherein the n-type organic compound contains a fullerene-based compound selected from the group consisting of fullerenes and derivatives thereof.

(13) The photoelectric conversion element according to (12), wherein a content ratio of the fullerene-based compound to a sum of the fullerene-based compound and one or more of the compounds represented by General formulae (1) to (3) (film thickness of the fullerene-based compound expressed in terms of a single layer/(film thickness of one or more of the compounds represented by General formulae (1) to (3) expressed in terms of a single layer+film thickness of the fullerene-based compound expressed in terms of a single layer)) is equal to or greater than 50% by volume.

(14) The photoelectric conversion element according to any one of (1) to (13), wherein a charge blocking film is disposed between the conductive film and the transparent conductive film.

(15) The photoelectric conversion element according to (14), comprising the conductive film, the charge blocking film, the photoelectric conversion film, and the transparent conductive film in this order, or the conductive film, the photoelectric conversion film, the charge blocking film, and the transparent conductive film in this order.

(16) The photoelectric conversion element according to any one of (1) to (15), wherein light enters the photoelectric conversion film via the transparent conductive film.

(17) The photoelectric conversion element according to any one of (1) to (16), wherein the transparent conductive film is composed of a transparent conductive metal oxide.

(18) An imaging device comprising the photoelectric conversion element according to any one of (1) to (17).

(19) An optical sensor comprising the photoelectric conversion element according to any one of (1) to (17).

(20) A method of using the photoelectric conversion element according to any one of (1) to (17), wherein the conductive film and the transparent conductive film constitute a pair of electrodes, and an electric field of $1 \times 10^{-5}$ V/cm to $1 \times 10^7$ V/cm is applied between the pair of electrodes.

(21) A compound represented by General formula (16) described below.

(22) A compound represented by General formula (17) described below.

According to the present invention, it is possible to provide a photoelectric conversion element which exhibits excellent photoelectric conversion efficiency and responsiveness.

Furthermore, according to the present invention, it is possible to provide an imaging device and an optical sensor each of which includes the photoelectric conversion element.

BRIEF DESCRIPTION OF THE DRAWINGS

Each of FIG. 1A

DETAILED DESCRIPTION OF THE INVENTION

Figure 1A:
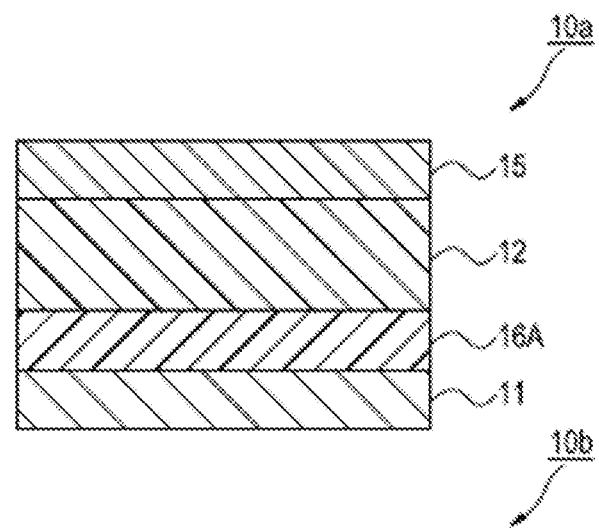
FIG. 1B is a schematic cross-sectional view showing an example of configuration of a photoelectric conversion element.

Hereinafter, preferred embodiments of the photoelectric conversion element of the present invention will be described.

First, characteristics of the present invention will be specifically described through comparison with the technique of the prior art.

As described above, in the present invention, it was found that, by using a photoelectric conversion film containing a compound having a predetermined structure, intended effects can be obtained.

Hereinafter, preferable embodiments of the photoelectric conversion element of the present invention will be described with reference of drawings. FIG. 1 are schematic cross-sectional views of an embodiment of the photoelectric conversion element of the present invention.

A photoelectric conversion element 10a shown in FIG. 1A has a configuration in which a conductive film 11 (hereinafter, also referred to as a "lower electrode") that functions as a lower electrode, an electron blocking film 16A that is formed on the lower electrode 11, a photoelectric conversion film 12 that is formed on the electron blocking film 16A, and a transparent conductive film 15 (hereinafter, also referred to as an "upper electrode") that functions as an upper electrode are laminated on one another in this order.

Figure 1B:
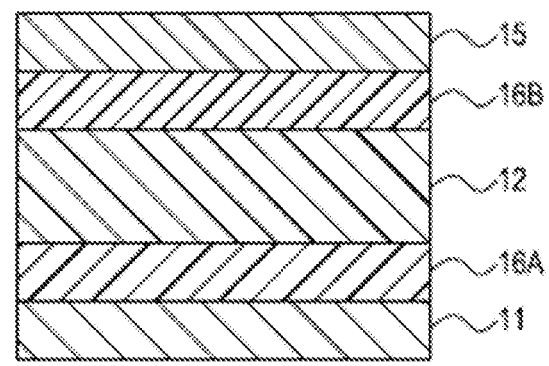

FIG. 1B shows an example of configuration of another photoelectric conversion element. A photoelectric conversion element 10b shown in FIG. 1B has a configuration in which on the lower electrode 11, the electron blocking film 16A, the photoelectric conversion film 12, a hole blocking film 16B, and the upper electrode 15 are laminated in this order. The electron blocking film 16A, the photoelectric conversion film 12, and the hole blocking film 16B in FIG. 1A and FIG. 1B may be laminated in an inverse order, according to the intended use and characteristics of the element. For example, the positions of the electron blocking film 16A and the photoelectric conversion film 12 may be switched.

In the configuration of the photoelectric conversion element 10a (10b), it is preferable for light to enter the photoelectric conversion film 12 through the transparent conductive film 15.

Furthermore, when the photoelectric conversion element 10a (10b) is used, an electric field can be applied thereto. In this case, the conductive film 11 and the transparent conductive film 15 constitute a pair of electrodes, and it is preferable to apply an electric field of $1 \times 10^{-5}$ V/cm to $1 \times 10^7$ V/cm between the pair of electrodes. From the viewpoint of performance and power consumption, an electric field of $1 \times 10^{-4}$ V/cm to $1 \times 10^6$ V/cm is preferable, and an electric field of $1 \times 10^{-3}$ V/cm to $5 \times 10^5$ V/cm is particularly preferable.

Regarding a voltage applying method, it is preferable to apply voltage such that the electron blocking film 16A becomes a negative pole, and the photoelectric conversion film 12 becomes a positive pole, in FIG. 1A and FIG. 1B. When the photoelectric conversion element 10a (10b) is used as an optical sensor or included in an imaging device, voltage can be applied by the same method as described above.

Hereinafter, embodiments of the respective layers (the photoelectric conversion film 12, the electron blocking film 16A, the lower electrode 11, the upper electrode 15, the hole blocking film 16B, and the like) constituting the photoelectric conversion element 10a (10b) will be described in detail.

First, the photoelectric conversion film 12 will be described in detail.

[Photoelectric Conversion Film]

The photoelectric conversion film 12 is a film containing, as a photoelectric conversion material, at least one compound selected from the group consisting of a compound represented by General formula (1), a compound represented by General formula (2), and a compound represented by General formula (3), which will be described later. By the use of such a compound, a photoelectric conversion element which exhibits excellent photoelectric conversion efficiency and responsiveness is obtained.

First, the compounds represented by General formulae (1) to (3) used in the photoelectric conversion film 12 will be specifically described.

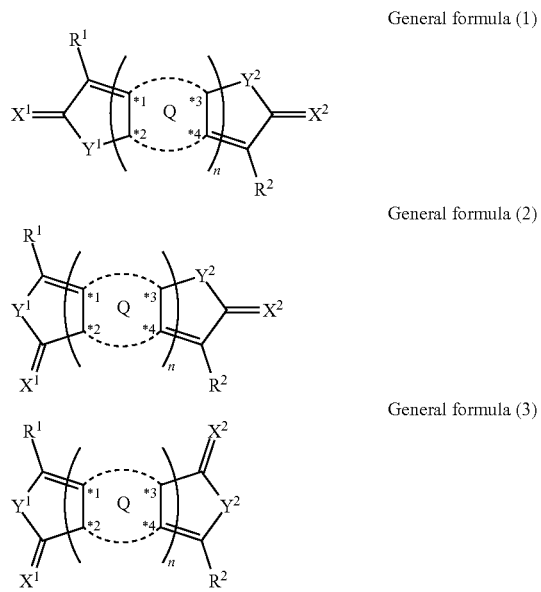

In General formulae (1) to (3), each of $R^1$ and $R^2$ independently represents a substituent. Examples of the substituent include a substituent W which will be described later. Examples of the substituent specifically include an alkyl group which may have a substituent, an amino group which may have a substituent (for example, a diarylamino group), an aryl group which may have a substituent (for example, an aryl group having an alkoxy group, a group represented by General formula (14) which will be described later, a group represented by General formula (18) which will be described later, or a group represented by General formula (15) which will be described later), a heteroaryl group which may have a substituent, and the like. Among these, because the characteristics (photoelectric conversion efficiency or responsiveness) of the photoelectric conversion element are further improved (hereinafter, also simply described as "because the effects of the present invention are further improved"), an aryl group which may have a substituent and a heteroaryl group which may have a substituent are preferable.

The number of carbon atoms in the alkyl group is not particularly limited. Because the characteristics (photoelectric conversion efficiency or responsiveness) of the photoelectric conversion element are further improved, the number of carbon atoms is preferably 1 to 10, more preferably 1 to 6, and even more preferably 1 to 3. The alkyl group may have any of a linear structure, a branched structure, and a cyclic structure.

Preferred examples of the alkyl group include a methyl group, an ethyl group, an n-propyl group, an n-butyl group, an n-hexyl group, and the like.

The alkyl group may have the substituent W which will be described later.

The amino group may be an unsubstituted amino group or an amino group which has a substituent. Because the characteristics (photoelectric conversion efficiency or responsiveness) of the photoelectric conversion element are further improved, an amino group which has a substituent (substituted amino group) is preferable, and a diarylamino group is particularly preferable.

The definition of the aryl group contained in the diarylamino group is the same as the definition of the aryl group which will be described later.

The number of carbon atoms in the aryl group is not particularly limited. Because the characteristics (photoelectric conversion efficiency or responsiveness) of the photoelectric conversion element are further improved, the number of carbon atoms is preferably 6 to 30, and more preferably 6 to 18. The aryl group may have a monocyclic structure or a fused ring structure in which two or more rings are fused with each other. Furthermore, the aryl group may have the substituent W which will be described later.

Examples of the aryl group include a phenyl group, a naphthyl group, an anthryl group, a pyrenyl group, a phenanthrenyl group, a biphenyl group, a fluorenyl group, and the like. Among these, a phenyl group, a naphthyl group, and an anthryl group are preferable.

The number of carbon atoms in the heteroaryl group (a monovalent aromatic heterocyclic group) is not particularly limited. Because the characteristics (photoelectric conversion efficiency or responsiveness) of the photoelectric conversion element are further improved, the number of carbon atoms is preferably 3 to 30, and more preferably 3 to 18. The heteroaryl group may have the substituent W which will be described later.

The heteroaryl group contains a heteroatom in addition to carbon atoms and hydrogen atoms. Examples of the heteroatom include a nitrogen atom, a sulfur atom, an oxygen atom, a selenium atom, a tellurium atom, a phosphorus atom, a silicon atom, and a boron atom. Among these, a nitrogen atom, a sulfur atom, and an oxygen atom are preferable. The number of the heteroatoms contained in the heteroaryl group is not particularly limited. Generally, the number of the heteroatoms is about 1 to 10, and preferably 1 to 4.

The number of ring members of the heteroaryl group is not particularly limited. The heteroaryl group is preferably a 3- to 8-membered ring, more preferably a 5- to 7-membered ring, and particularly preferably a 5- to 6-membered ring.

Examples of the heteroaryl group include a pyridyl group, a quinolyl group, an isoquinolyl group, an acridinyl group, a phenanthridinyl group, a pteridinyl group, a pyrazinyl group, a quinoxalinyl group, a pyrimidinyl group, a quinazolyl group, a pyridazinyl group, a cinnolinyl group, a phthalazinyl group, a triazinyl group, an oxazolyl group, a benzoxazolyl group, a triazolyl group, a benzothiazolyl group, an imidazolyl group, a benzimidazolyl group, a pyrazolyl group, an indazolyl group, an isoxazolyl group, a benzisoxazolyl group, an isothiazolyl group, a benzisothiazolyl group, an oxadiazolyl group, a thiadiazolyl group, a triazolyl group, a tetrazolyl group, a furyl group, a benzofuryl group, a thienyl group, a benzothienyl group, a thienothienyl group, a dibenzofuryl group, a dibenzothienyl group, a pyrrolyl group, an indolyl group, an imidazopyridinyl group, a carbazolyl group, and the like.

$R^1$ and $R^2$ may represent different groups from each other. Because the characteristics (photoelectric conversion efficiency or responsiveness) of the photoelectric conversion element are further improved, it is preferable that $R^1$ and $R^2$ represent the same substituent (the same type of substituent).

As a preferred embodiment of $R^1$ and $R^2$, a group represented by General formula (14) is illustrated. At least one of $R^1$ and $R^2$ is preferably the group represented by General formula (14).

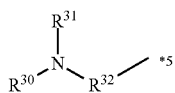

General formula (14)

In General formula (14), each of $R^{30}$ and $R^{31}$ independently represents an alkyl group, an aryl group which may have a substituent, or a heteroaryl group which may have a substituent. The definitions of the alkyl group, aryl group, and heteroaryl group are as described above.

$R^{32}$ represents an arylene group which may have a substituent or a heteroarylene group which may have a substituent.

*5 represents a bonding position.

The number of carbon atoms in the arylene group is not particularly limited. Because the characteristics (photoelectric conversion efficiency or responsiveness) of the photoelectric conversion element are further improved, the number of carbon atoms is preferably 6 to 30, and more preferably 6 to 20.

Examples of the arylene group include a phenylene group, a biphenylene group, a terphenylene group, a naphthylene group, an anthrylene group, a phenanthrylene group, a pyrenediyl group, a perylenediyl group, a fluorenediyl group, a chrysenediyl group, a triphenylenediyl group, a benzanthracenediyl group, a benzophenanthrenediyl group, and the like.

The number of carbon atoms in the heteroarylene group is not particularly limited. Because the characteristics (photoelectric conversion efficiency or responsiveness) of the photoelectric conversion element are further improved, the number of carbon atoms is preferably 1 to 20, and more preferably 2 to 12.

Examples of the heteroarylene group include a pyridylene group, a quinolilene group, an isoquinolilene group, an acridinediyl group, a phenanthridinediyl group, a pyrazinediyl group, a quinoxalinediyl group, a pyrimidinediyl group, a triazinediyl group, an imidazolediyl group, a pyrazolediyl group, an oxadiazolediyl group, a triazolediyl group, a furylene group, a thienylene group, a benzothienylene group, a thienothienylene group, a pyrrolediyl group, an indolediyl group, a carbazolediyl group, and the like.

$R^{30}$ to $R^{32}$ may form a ring by being linked to each other.

In terms of bonding, $R^{30}$ and $R^{31}$, $R^{30}$ and $R^{32}$, or $R^{31}$ and $R^{32}$ preferably form a ring by being directly bonded to each other or by being bonded to each other through a linking group. Because the characteristics (photoelectric conversion efficiency or responsiveness) of the photoelectric conversion element are further improved, $R^{30}$ and $R^{31}$, $R^{30}$ and $R^{32}$, or $R^{31}$ and $R^{32}$ more preferably form a ring by being bonded to each other through a linking group.

The structure of the linking group is not particularly limited. Examples of the linking group include an oxygen atom, a sulfur atom, an alkylene group, a silylene group, an alkenylene group, a cycloalkylene group, a cycloalkenylene group, an arylene group, a divalent heterocyclic group, an imino group, and combination groups thereof. These groups may each further have a substituent. Among these, an alkylene group, a silylene group, an alkenylene group, a cycloalkylene group, a cycloalkenylene group, an arylene group, and the like are preferable, and an alkylene group is more preferable.

As a more preferred embodiment of $R^1$ and $R^2$ (preferred embodiment of the group represented by General formula (14)), a group represented by General formula (18) is illustrated. At least one of $R^1$ and $R^2$ is preferably the group represented by General formula (18).

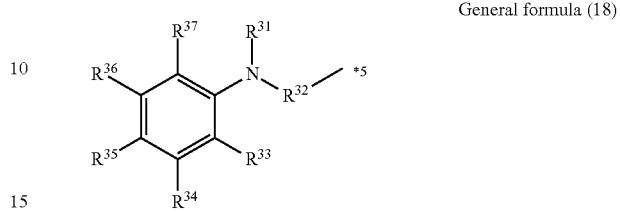

General formula (18)

In General formula (18), $R^{31}$ represents an alkyl group, an aryl group which may have a substituent, or a heteroaryl group which may have a substituent. The definition of $R^{31}$ is as described above.

$R^{32}$ represents an arylene group which may have a substituent or a heteroarylene group which may have a substituent. The definition of $R^{32}$ is as described above.

Each of $R^{33}$ to $R^{37}$ independently represents a hydrogen atom or a substituent. The definition and preferred embodiment of the substituent are the same as those of the substituent represented by each of $R^1$ and $R^2$ described above.

*5 represents a bonding position.

$R^{33}$ and $R^{32}$, $R^{37}$ and $R^{31}$, or $R^{31}$ and $R^{32}$ may form a ring by being linked to each other. In terms of bonding, $R^{37}$ and $R^{31}$, $R^{32}$ and $R^{33}$, or $R^{32}$ and $R^{31}$ preferably form a ring by being directly bonded to each other or by being bonded to each other through a linking group. Because the characteristics (photoelectric conversion efficiency or responsiveness) of the photoelectric conversion element are further improved, $R^{37}$ and $R^{31}$, $R^{32}$ and $R^{33}$, or $R^{32}$ and $R^{31}$ more preferably form a ring by being bonded to each other through a linking group. The definition of the linking group is as described above.

As a more preferred embodiment of $R^1$ and $R^2$ (preferred embodiment of the group represented by General formula (14)), a group represented by General formula (15) is illustrated. At least one of $R^1$ and $R^2$ is preferably the group represented by General formula (15).

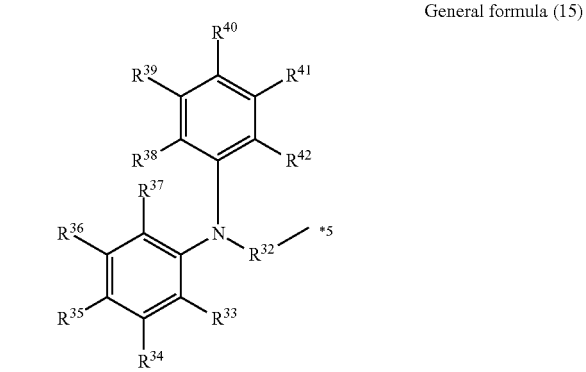

General formula (15)

In General formula (15), each of $R^{33}$ to $R^{42}$ independently represents a hydrogen atom or a substituent. The definition and preferred embodiment of the substituent are the same as those of the substituent represented by each of $R^1$ and $R^2$ described above.

$R^{32}$ represents an arylene group which may have a substituent or a heteroarylene group which may have a substituent. The definition of $R^{32}$ is as described above.

*5 represents a bonding position.

$R^{37}$ and $R^{38}$, $R^{32}$ and $R^{33}$, or $R^{32}$ and $R^{42}$ may form a ring by being linked to each other. In terms of bonding, $R^{37}$ and $R^{38}$, $R^{32}$ and $R^{33}$, or $R^{32}$ and $R^{42}$ preferably form a ring by being directly bonded to each other or by being bonded to each other through a linking group. Because the characteristics (photoelectric conversion efficiency or responsiveness) of the photoelectric conversion element are further improved, $R^{37}$ and $R^{38}$, $R^{32}$ and $R^{33}$, or $R^{32}$ and $R^{42}$ more preferably form a ring by being bonded to each other through a linking group. The definition of the linking group is as described above.

In General formulae (1) to (3), each of $X^1$ and $X^2$ independently represents an oxygen atom, a sulfur atom, $=CR^{1a}R^{1b}$, or $=NR^{1c}$.

Each of $Y^1$ and $Y^2$ independently represents an oxygen atom, a sulfur atom, $>CR^{1d}R^{1e}$, or $>SiR^{1f}R^{1g}$.

Each of $R^{1a}$ to $R^{1g}$ independently represents a hydrogen atom or a substituent. Examples of the substituent include the substituent W which will be described later. Specifically, examples of the substituent include an alkyl group and the like.

The combinations of $X^1$ and $X^2$ as well as $Y^1$ and $Y^2$ in General formulae (1) to (3) are not particularly limited. Because the effects of the present invention are further improved, these groups preferably establish $X^1=X^2$ and $Y^1=Y^2$, and it is more preferable that all of the groups are oxygen atoms.

In particular, because the effects of the present invention are further improved, a compound represented by General formula (12) and a compound represented by General formula (13) are preferable. The definition of each of the groups in General formulae (12) and (13) is as described above.

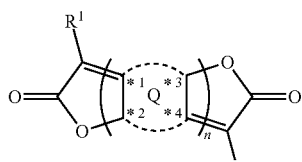

General formula (12)

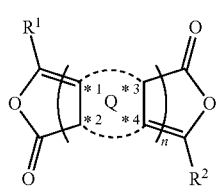

General formula (13)

Q represents one selected from the group consisting of the groups represented by General formulae (4) to (8).

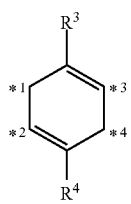

General formula (4)

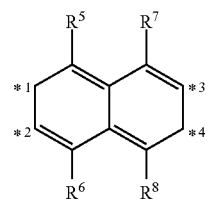

General formula (5)

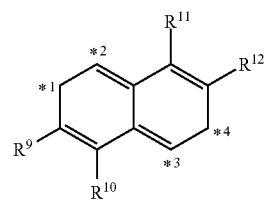

General formula (6)

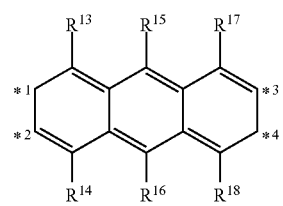

General formula (7)

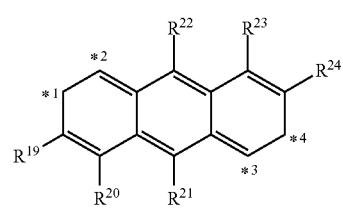

General formula (8)

In General formulae (4) to (8), each of $R^3$ to $R^{24}$ independently represents a hydrogen atom or a substituent. Examples of the substituent include the substituent W which will be described later. Specifically, examples of the substituent include an alkyl group, an alkoxy group, a halogen atom, and the like. In particular, because the characteristics (photoelectric conversion efficiency or responsiveness) of the photoelectric conversion element are further improved, each of $R^3$ to $R^{24}$ preferably represents a hydrogen atom.

The carbon atoms represented by *1 to *4 in General formulae (4) to (8) respectively correspond to the carbon atoms represented by *1 to *4 in General formulae (1) to (3). More specifically, in cases where the group represented by each of General formulae (4) to (8) is introduced into Q in each of General formulae (1) to (3), the structural formulae are as shown below.

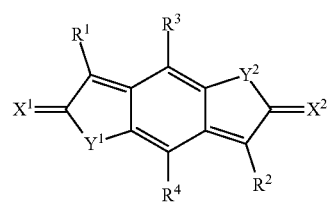

General formula (4A)

-continued
General formula (4B)
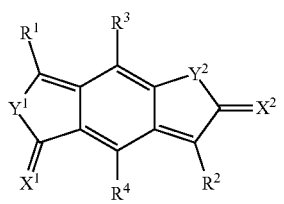
General formula (4C)
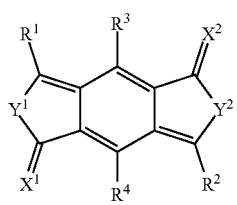
General formula (5A)
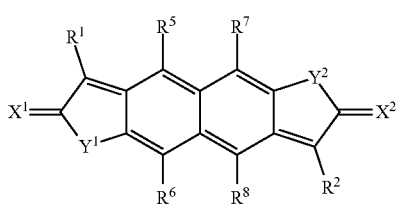
General formula (5B)
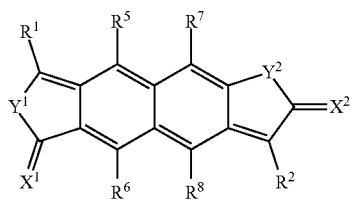
General formula (5C)
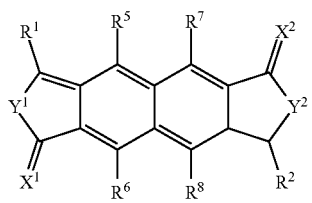
General formula (6A)
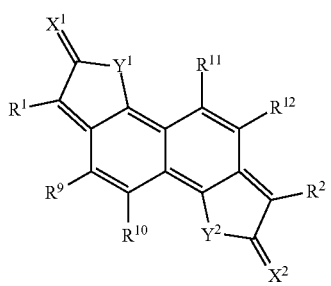
General formula (6B)
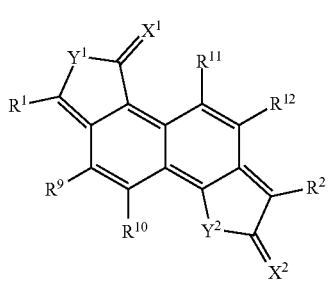
-continued
General formula (6C)
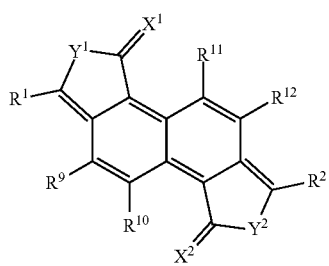
General formula (7A)
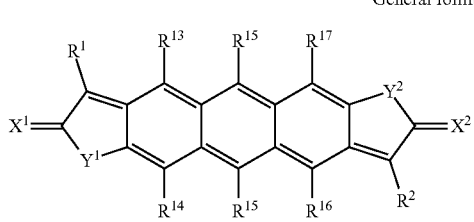
General formula (7B)
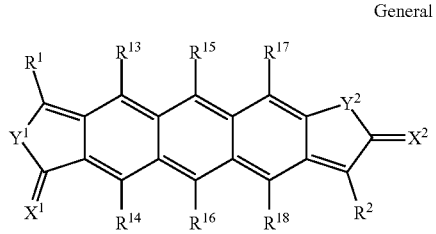
General formula (7C)
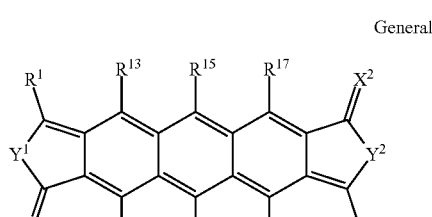
General formula (8A)
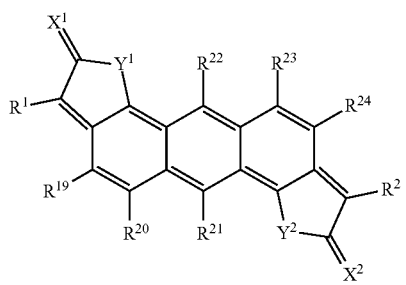
General formula (8B)
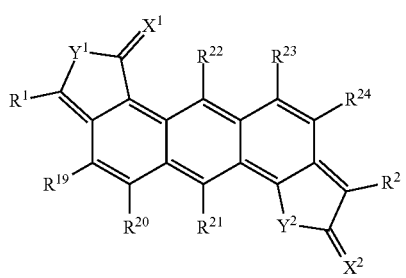

General formula (8C)

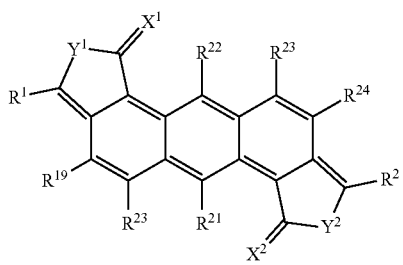

n represents 0 or 1. In particular, because the characteristics (photoelectric conversion efficiency or responsiveness) of the photoelectric conversion element are further improved, n is preferably 0.

When n is 1, the compounds represented by General formulae (4A) to (8C) described above are illustrated.

When n is 0, the carbon atom represented by *1 is identical to the carbon atom represented by *3, and the carbon atom represented by *2 is identical to the carbon atom represented by *4. That is, when n=0, the compounds represented by General formulae (1) to (3) are the compounds represented by General formulae (9) to (11) shown below, respectively.

The definition of each of the groups in General formulae (9) to (11) is as described above.

General formula (9)

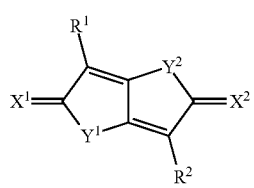

General formula (10)

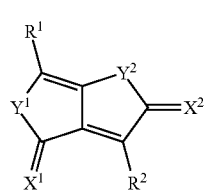

General formula (11)

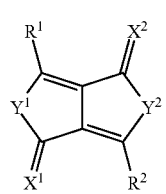

In particular, because the effects of the present invention are further improved, a compound represented by General formula (16) and a compound represented by General formula (17) are more preferable.

General formula (16)

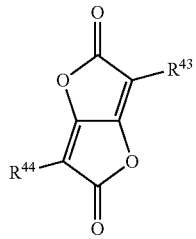

In General formula (16), each of $R^{43}$ and $R^{44}$ independently represents an aryl group which may have a substituent or a heteroaryl group which may have a substituent. At least one of $R^{43}$ and $R^{44}$ is the group represented by General formula (14) described above.

The definitions of the aryl group and the heteroaryl group are as described above.

General formula (17)

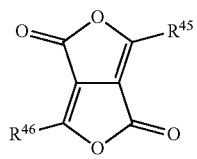

In General formula (17), each of $R^{45}$ and $R^{46}$ independently represents an aryl group which may have a substituent or a heteroaryl group which may have a substituent. At least one of $R^{45}$ and $R^{46}$ is the group represented by General formula (14) described above.

The definitions of the aryl group and the heteroaryl group are as described above.

The substituent W in the present specification will be described.

Examples of the substituent W include a halogen atom, an alkyl group (including a cycloalkyl group, a bicycloalkyl group, and a tricycloalkyl group), an alkenyl group (including a cycloalkenyl group and a bicycloalkenyl group), an alkynyl group, an aryl group, a heterocyclic group, a cyano group, a hydroxy group, a nitro group, a carboxy group, an alkoxy group, an aryloxy group, a silyloxy group, a heterocyclic oxy group, an acyloxy group, a carbamoyloxy group, an alkoxycarbonyloxy group, an aryloxycarbonyloxy group, an amino group (including an anilino group), an ammonio group, an acylamino group, an aminocarbonylamino group, an alkoxycarbonylamino group, an aryloxycarbonylamino group, a sulfamoylamino group, an alkyl or aryl sulfonylamino group, a mercapto group, an alkylthio group, an arylthio group, a heterocyclic thio group, a sulfamoyl group, a sulfo group, an alkyl or aryl sulfinyl group, an alkyl or aryl sulfonyl group, an acyl group, an aryloxycarbonyl group, an alkoxycarbonyl group, a carbamoyl group, an aryl or heterocyclic azo group, an imide group, a phosphino group, a phosphinyl group, a phosphinyloxy group, a phosphinylamino group, a phosphono group, a silyl group, a hydrazino group, an ureide group, a boronic acid group (—B(OH)$_2$), a phosphate group (—OPO(OH)$_2$), a sulfate group (—OSO$_3$H), and other known substituents.

The details of the substituent W are described in paragraph of JP 2007-234651 A.

The compounds represented by General formulae (1) to (3) are illustrated below. Herein, one kind of the compounds represented by General formulae (1) to (3) may be used singly, or two or more kinds thereof may be used.

15                                    16
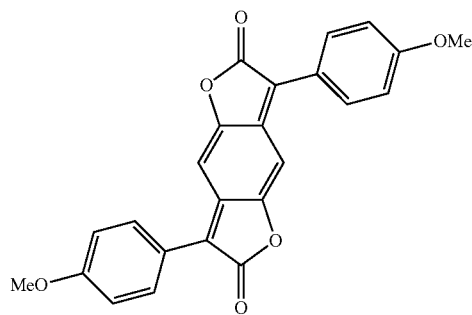
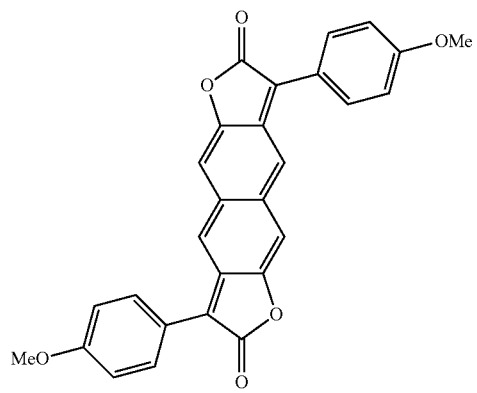
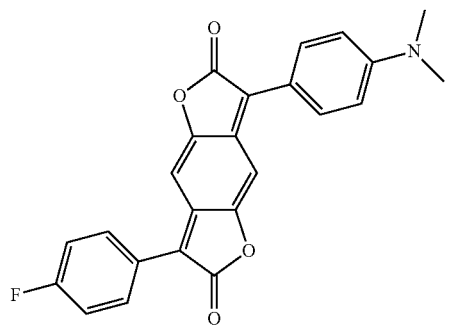
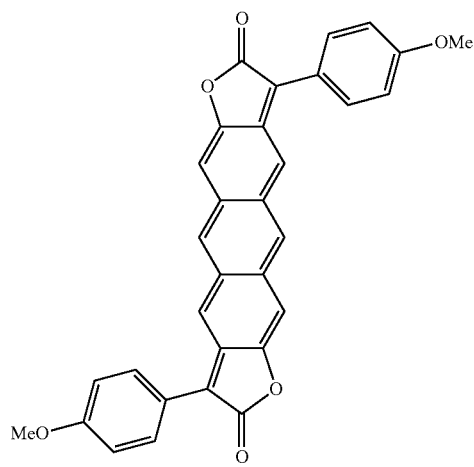
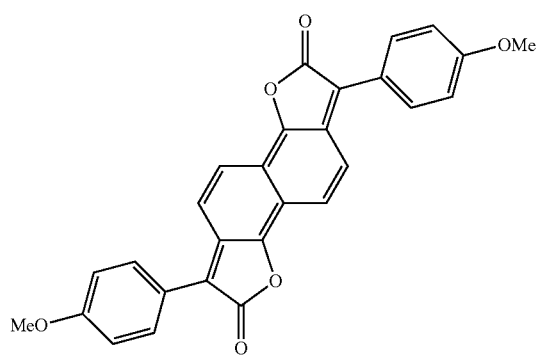
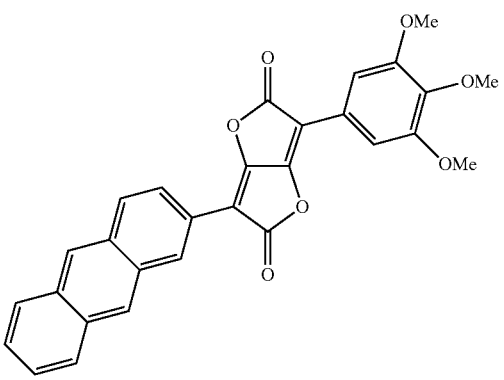
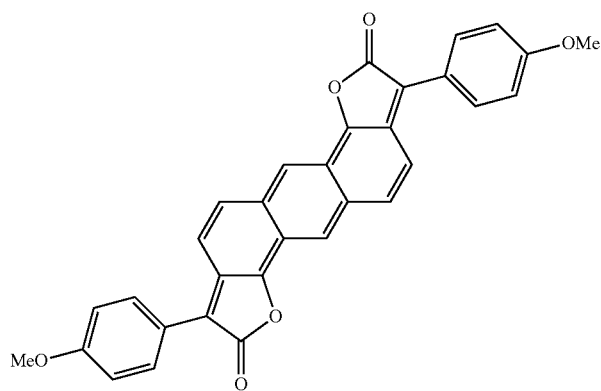
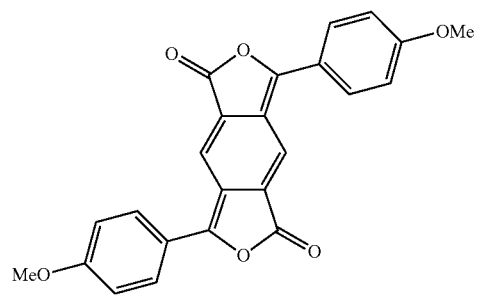

-continued
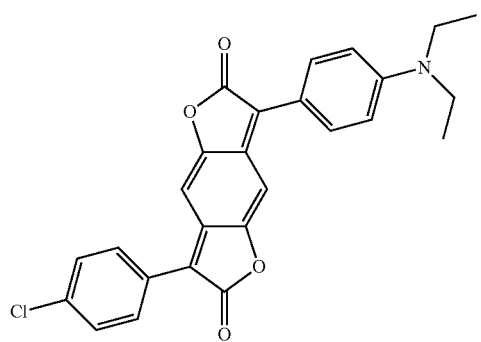
17
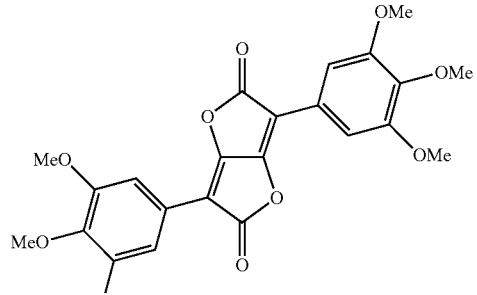
18
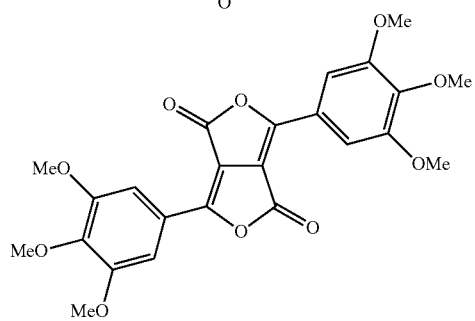
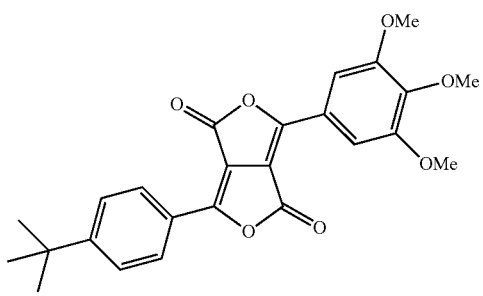
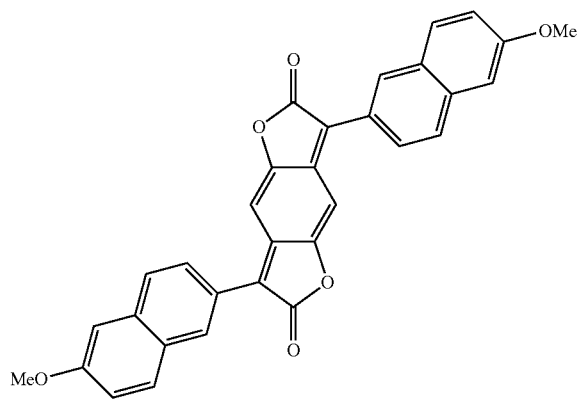
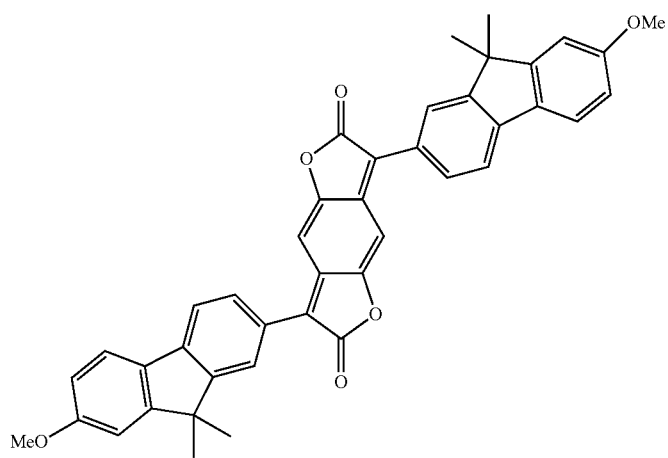
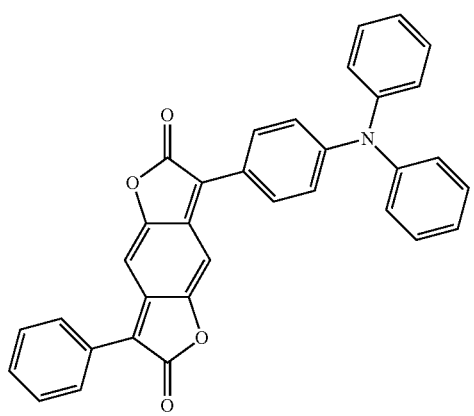

-continued
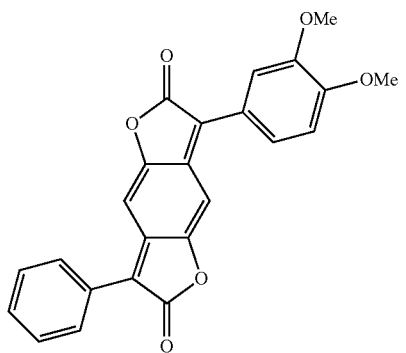
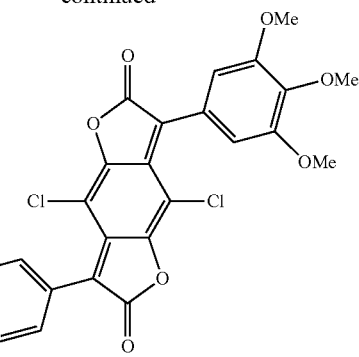
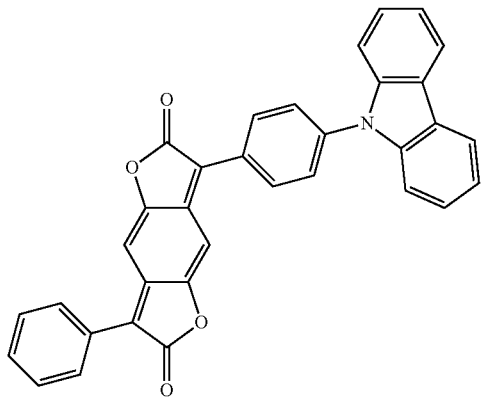
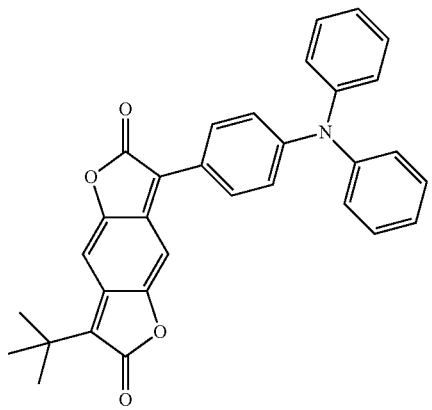
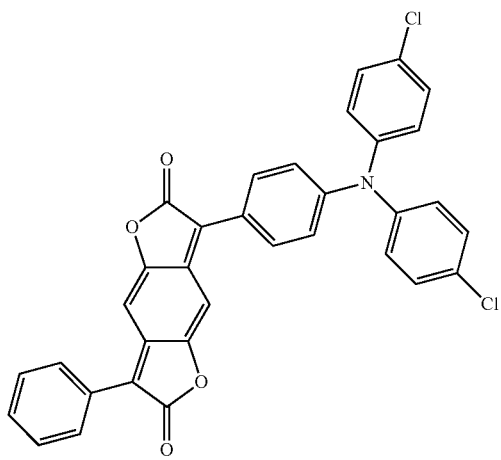
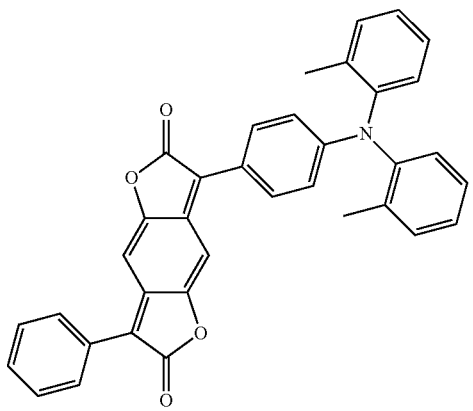
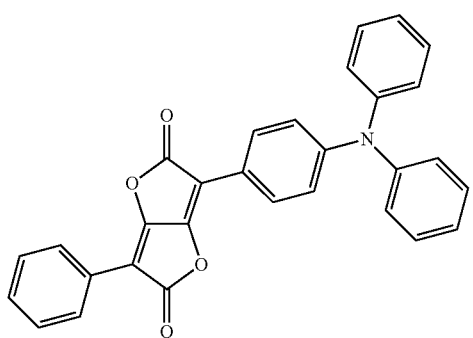
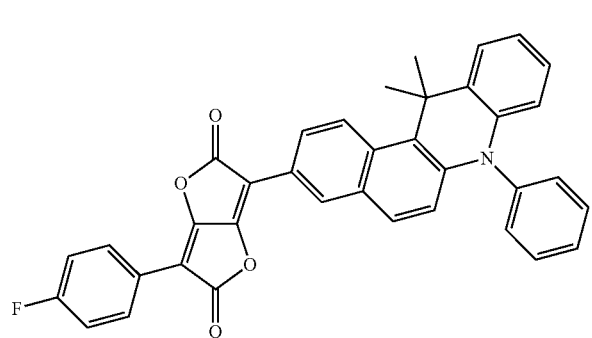

-continued
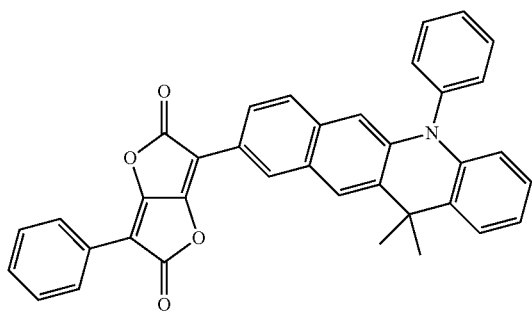
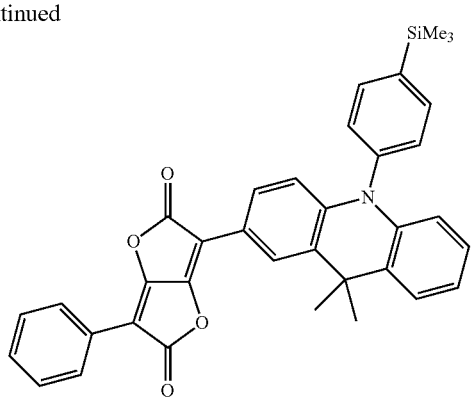
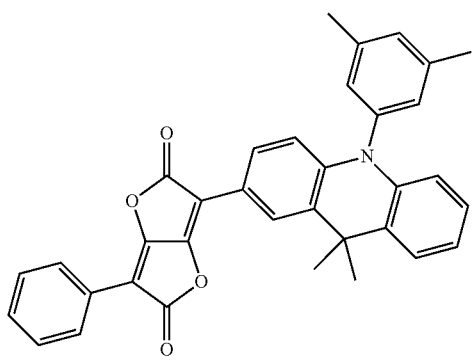
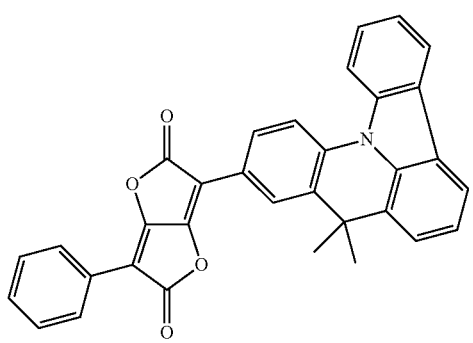
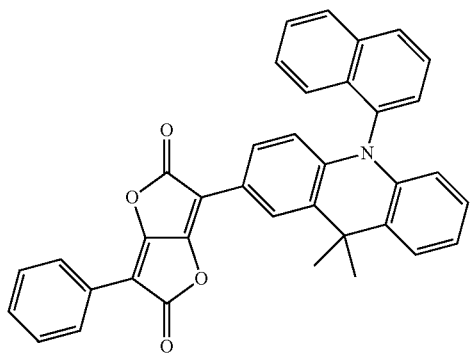
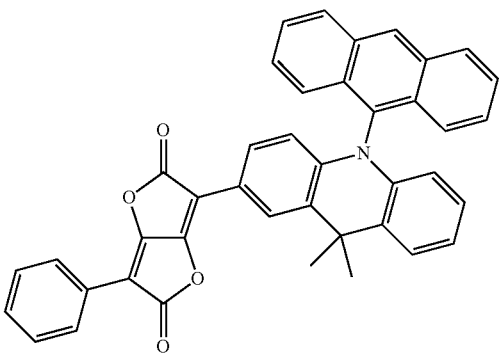
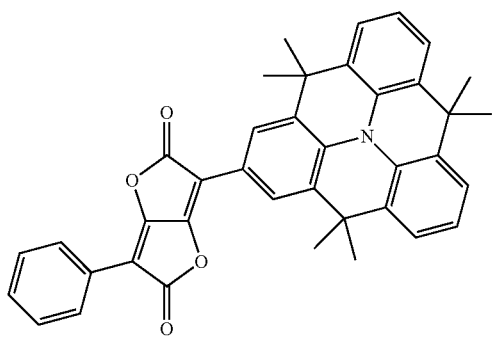
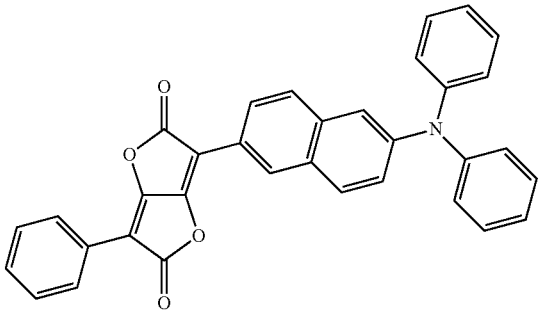

-continued
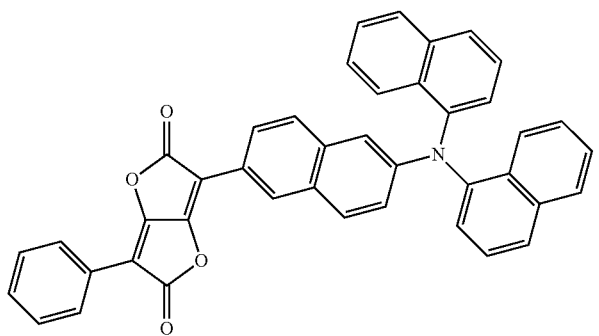
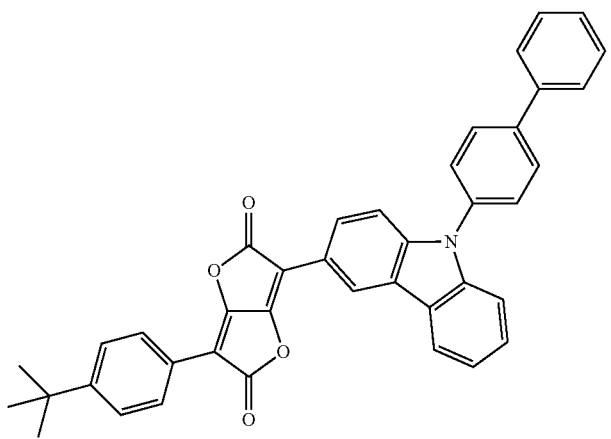
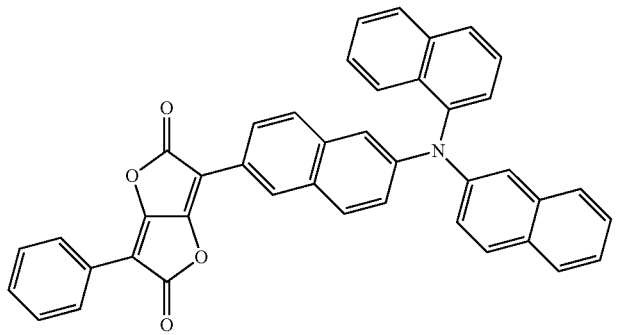
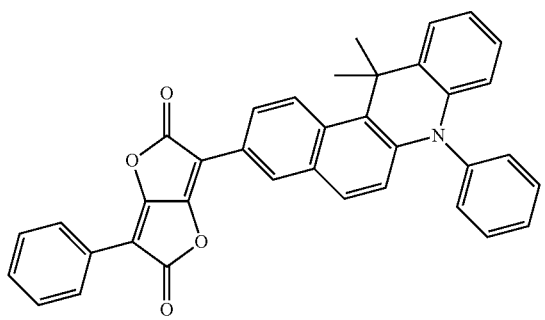
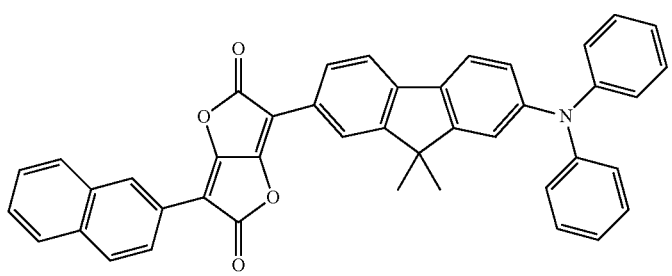

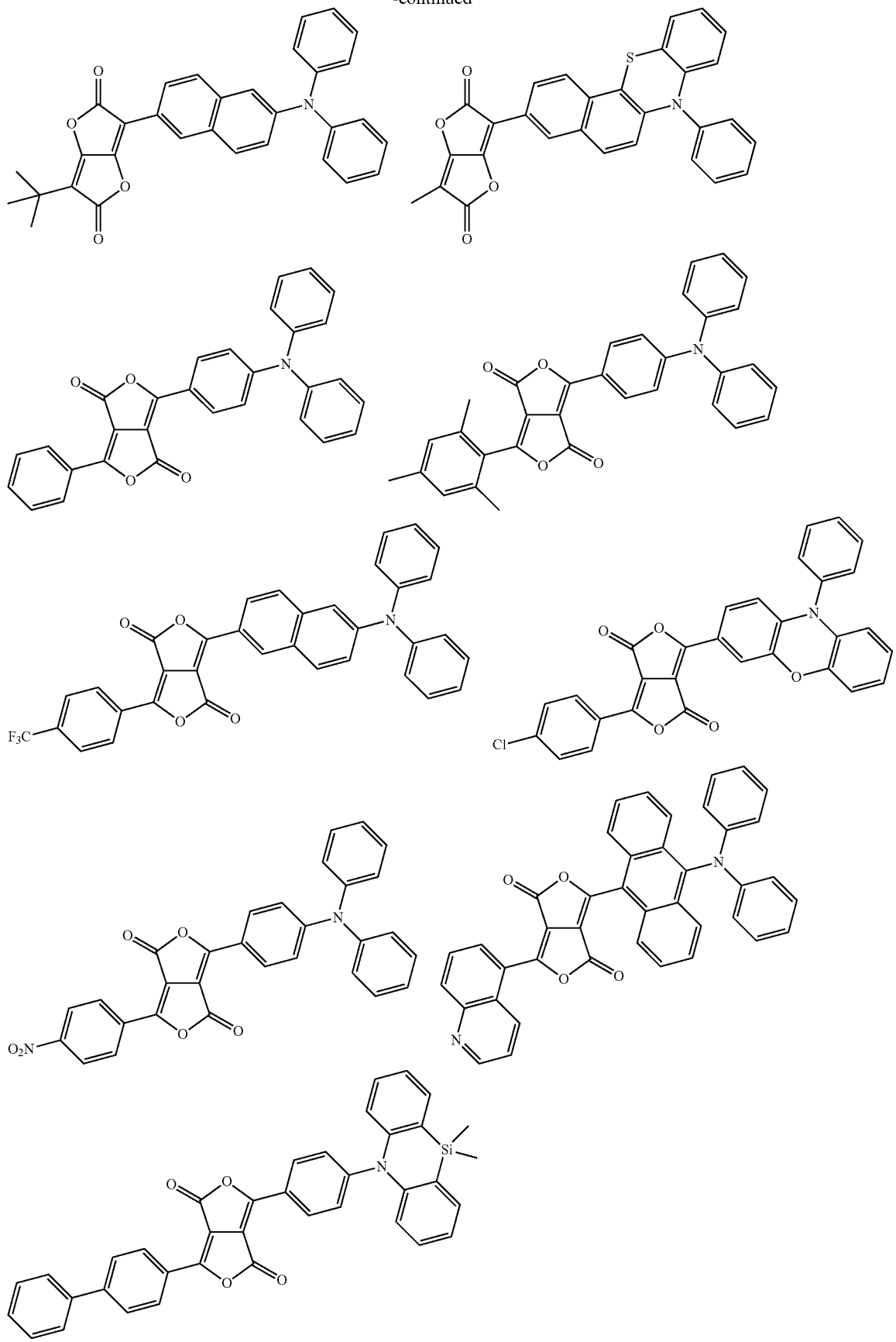

-continued
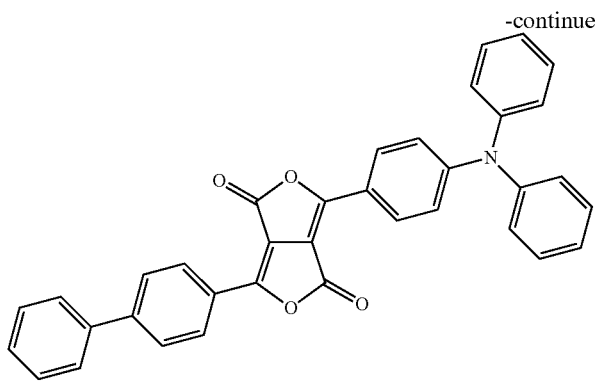
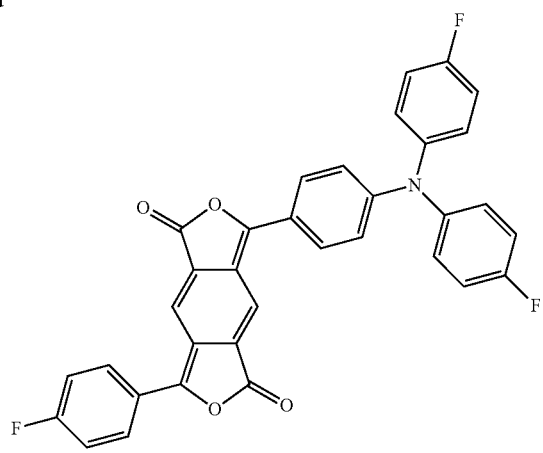
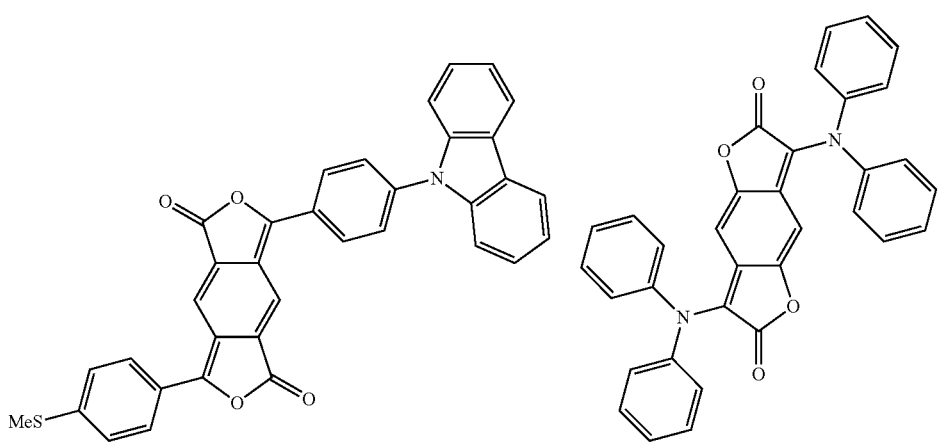
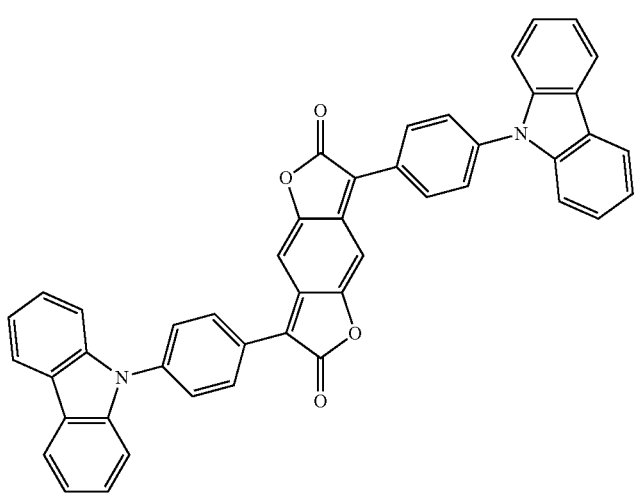

-continued
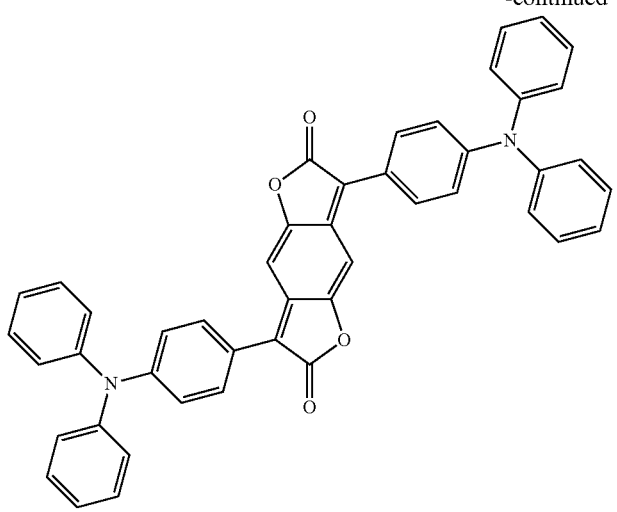
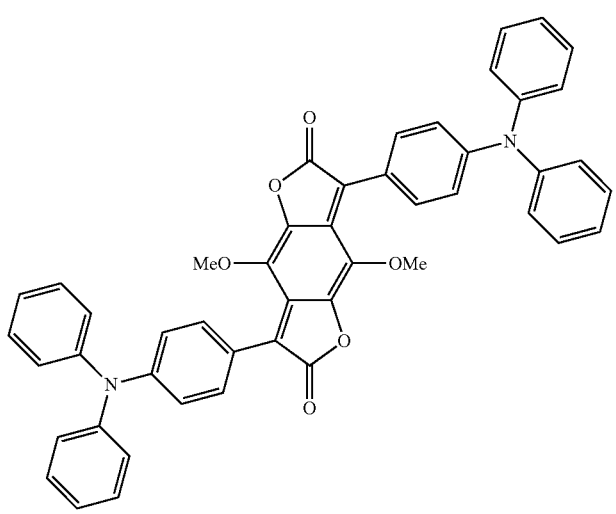
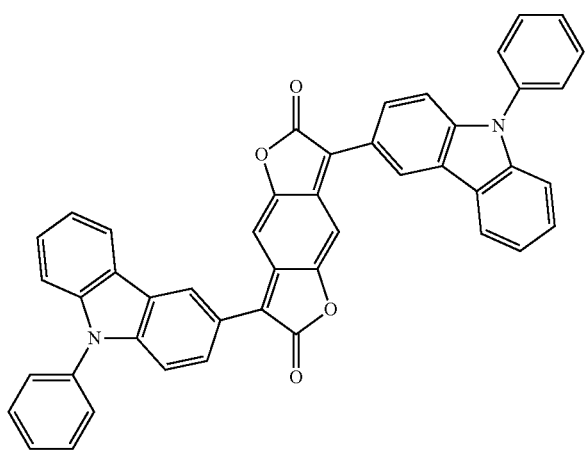

-continued
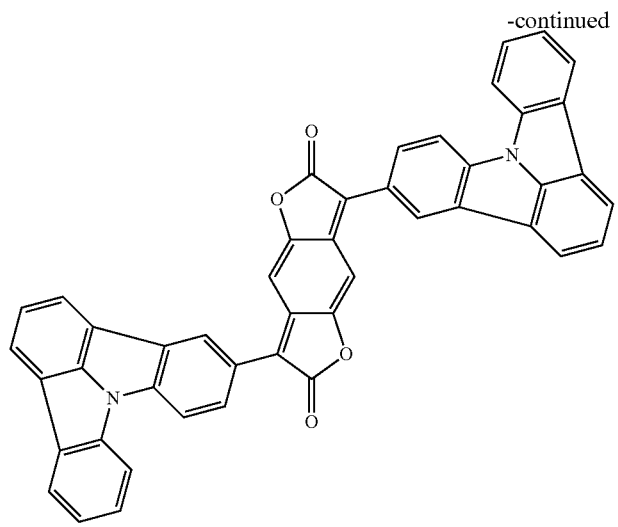
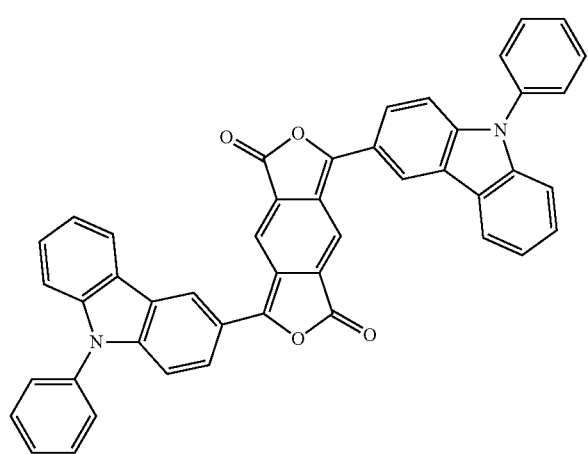
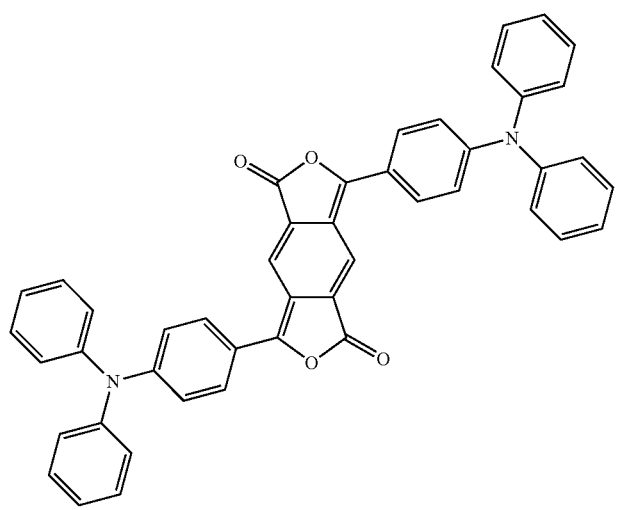

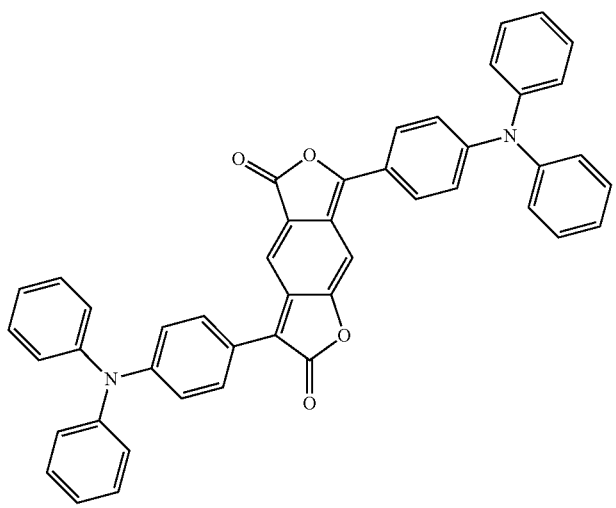
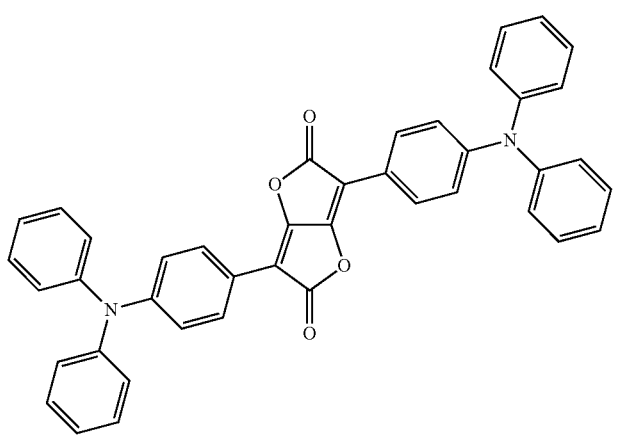
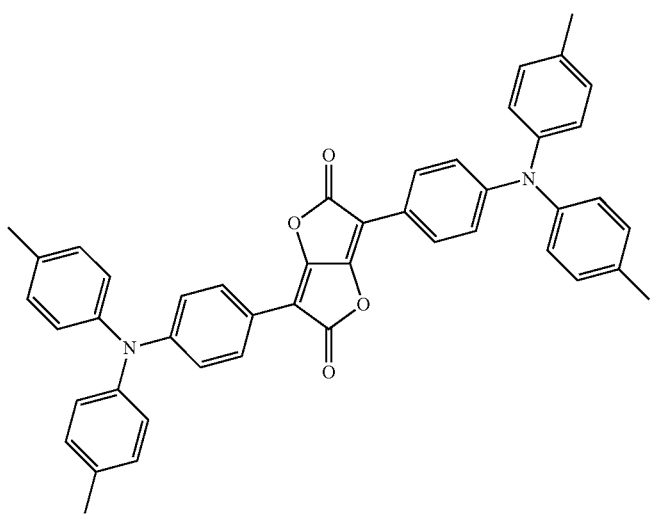

-continued
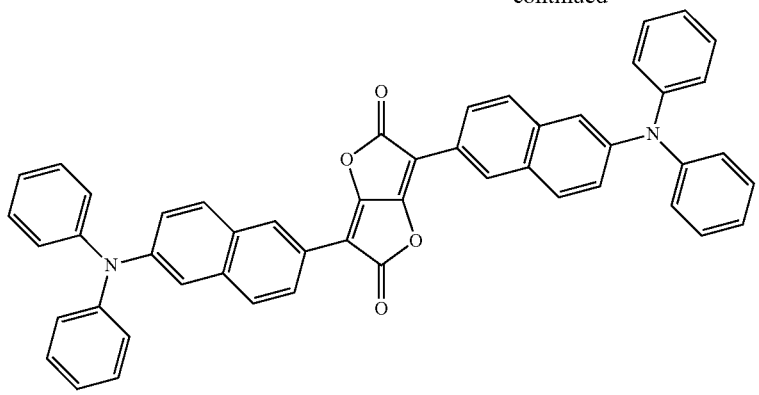
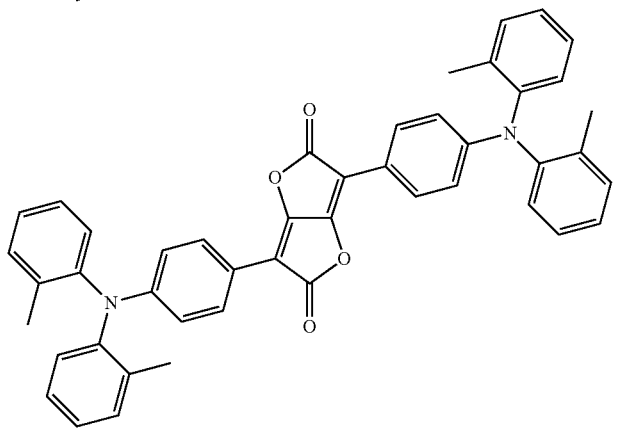
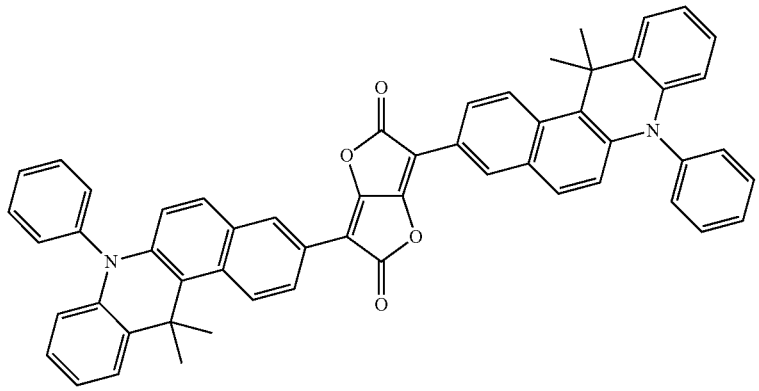
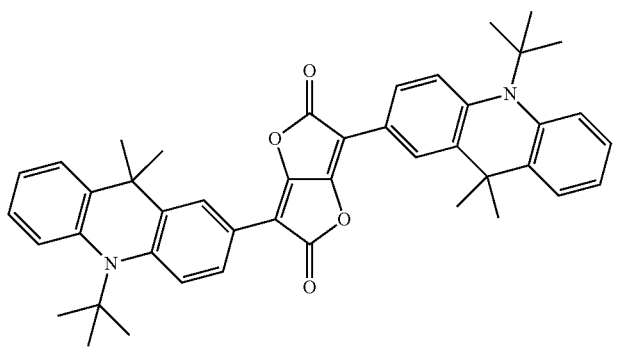

-continued
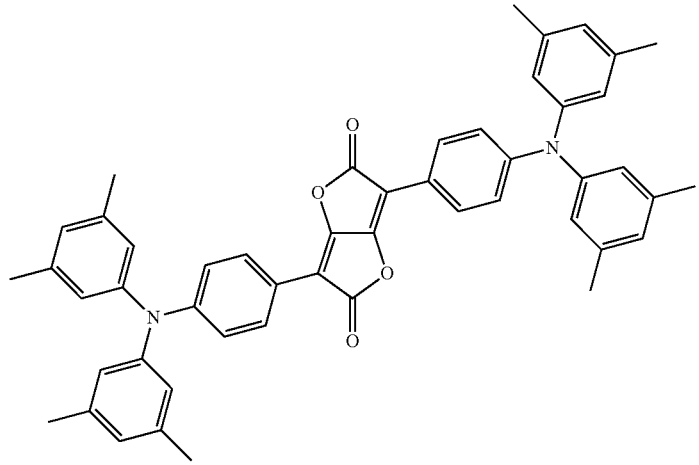
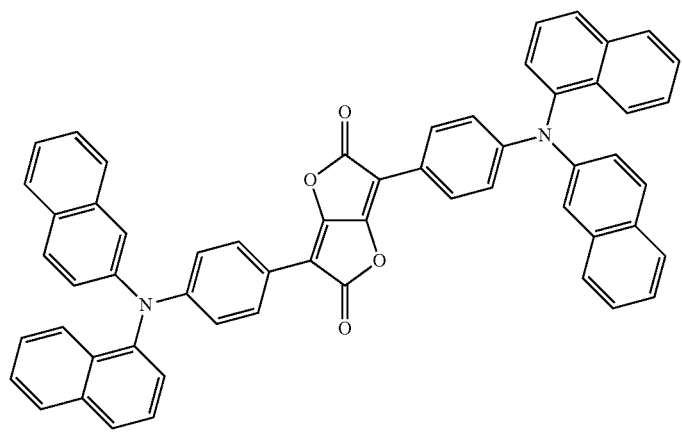
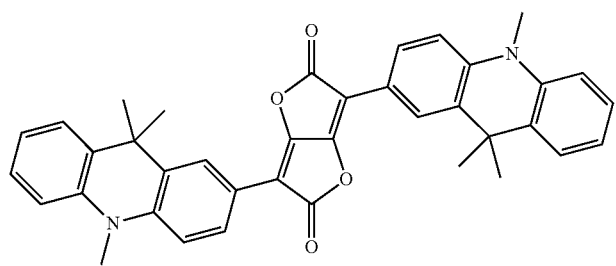
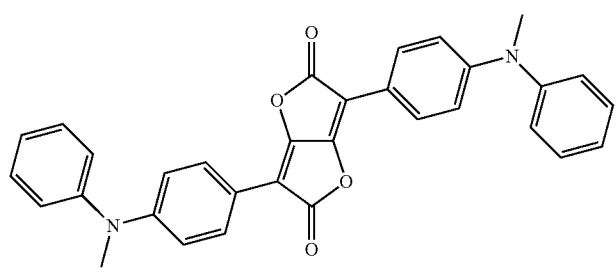

-continued
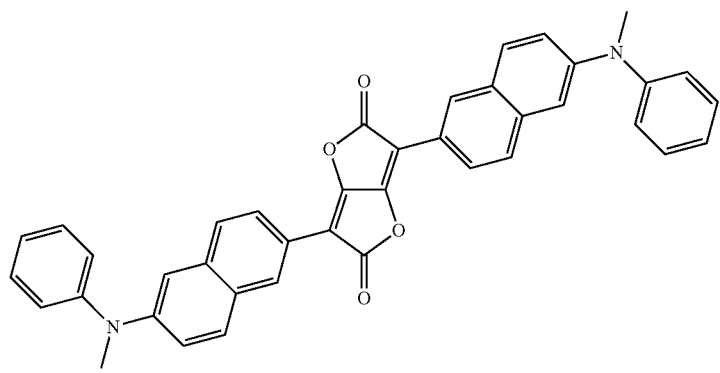
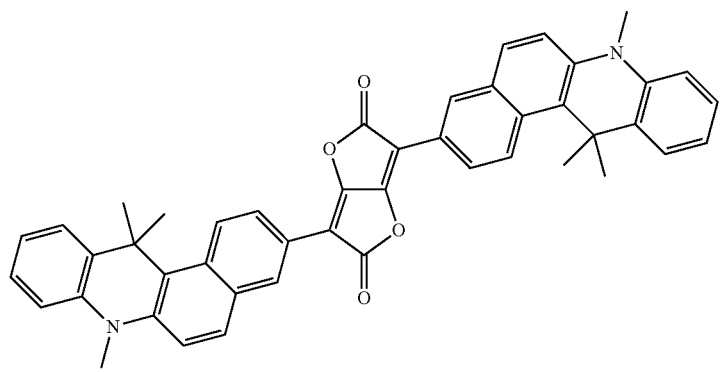
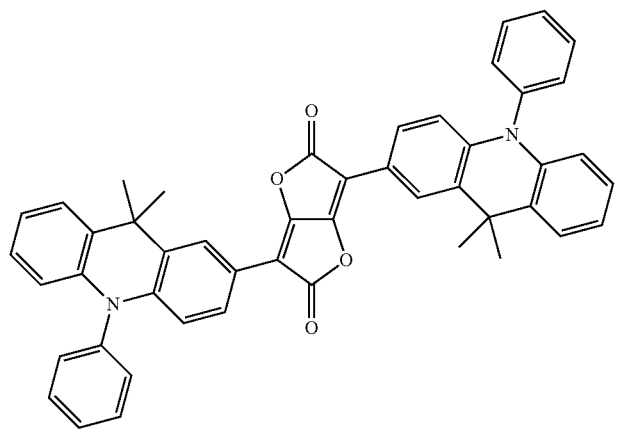
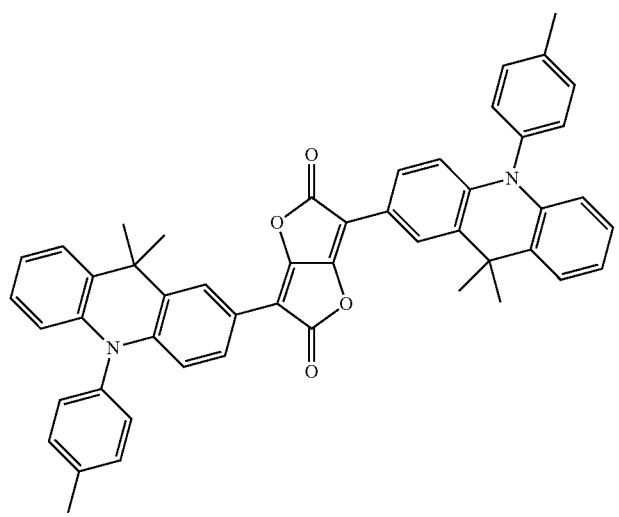

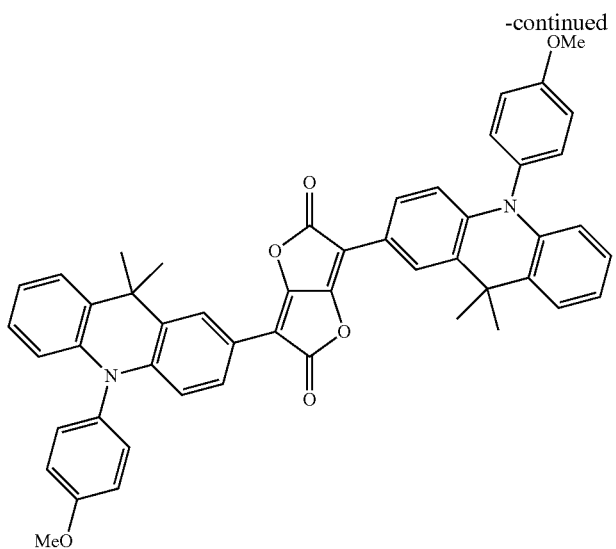
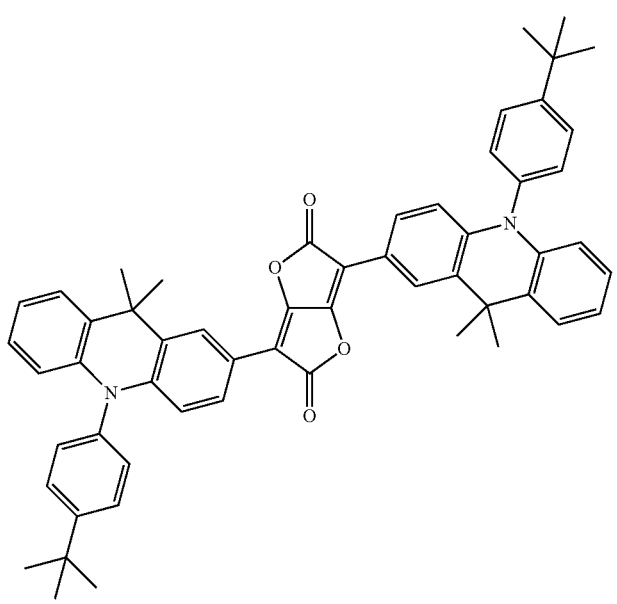
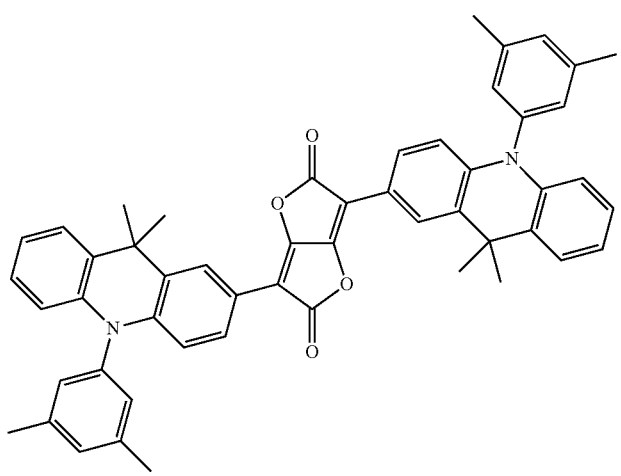

-continued
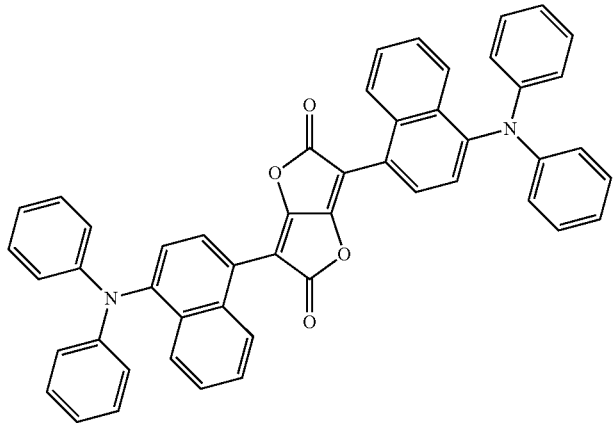
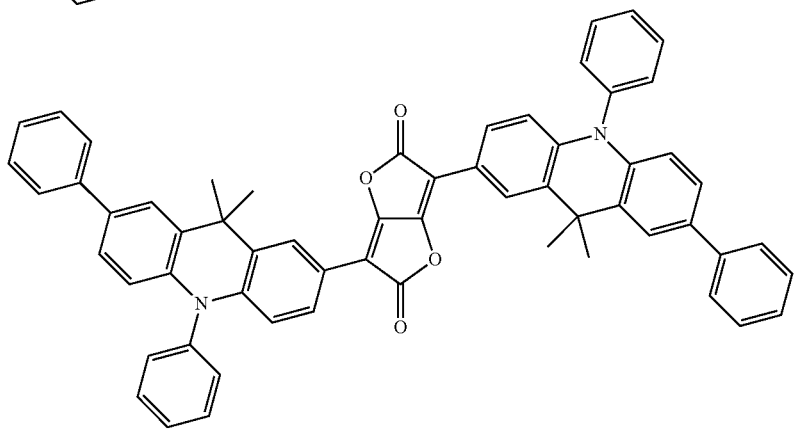
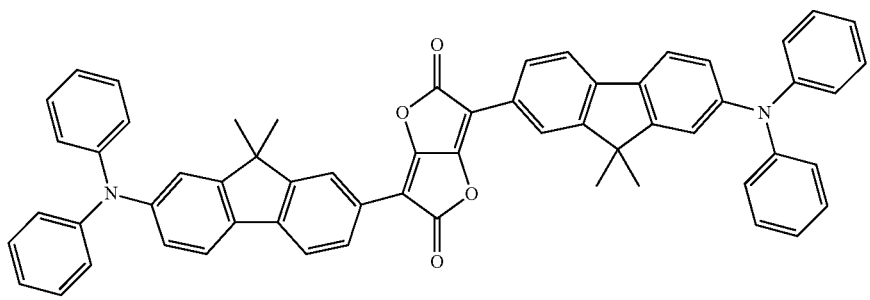
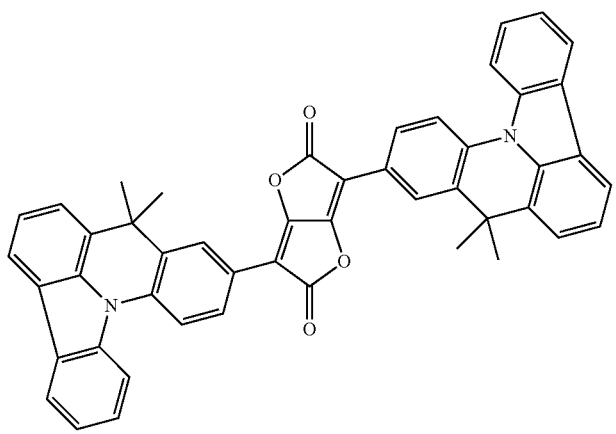

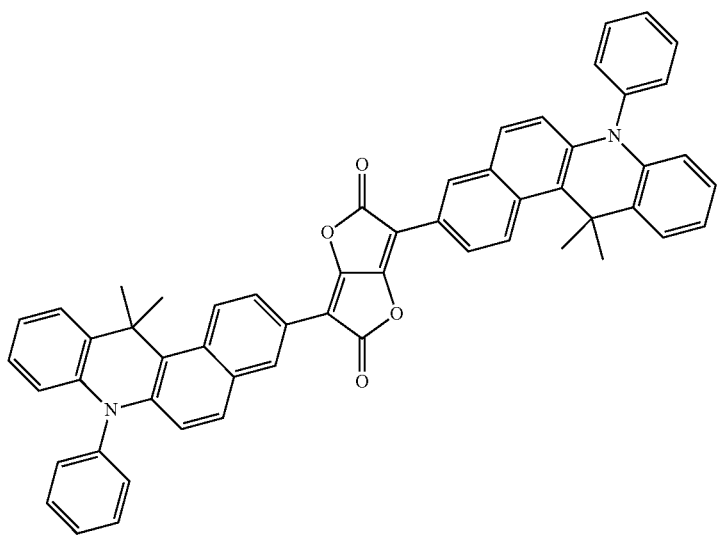
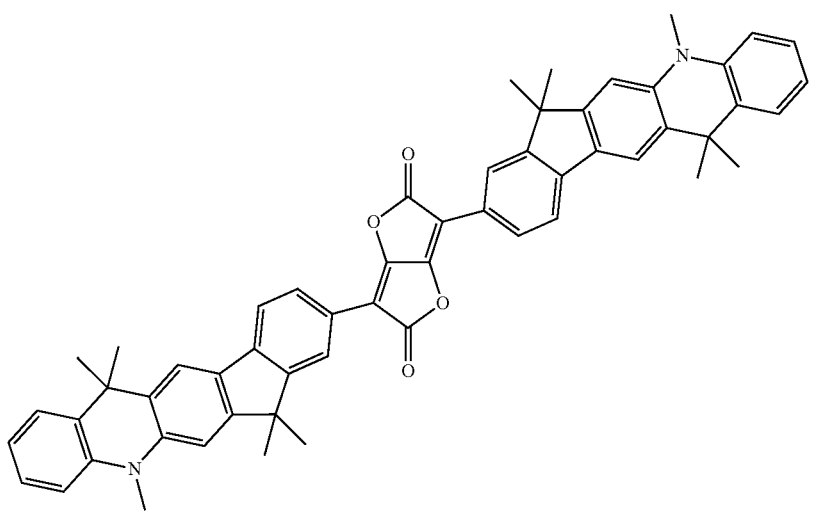
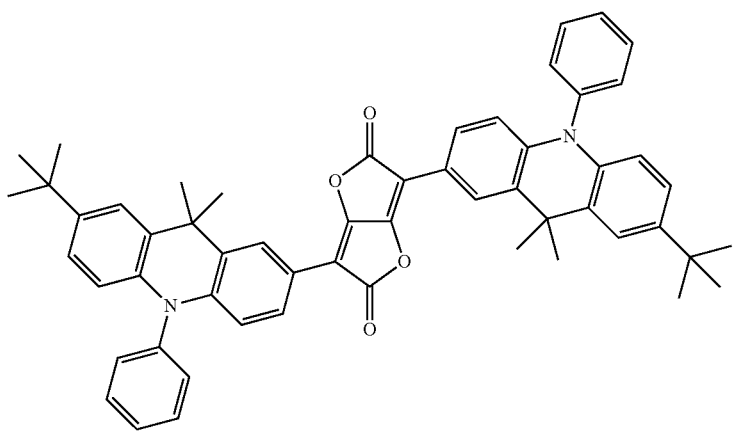

-continued
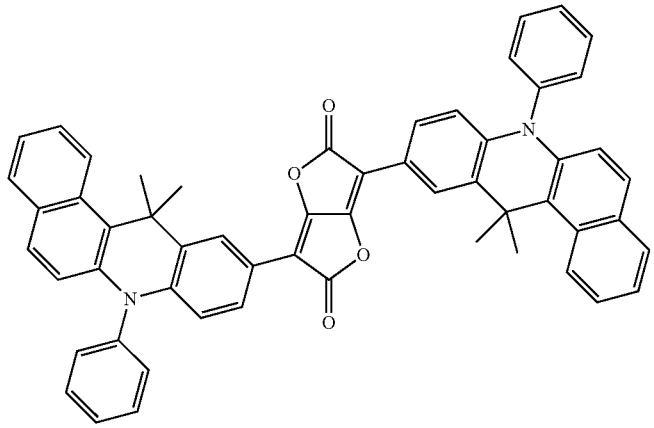
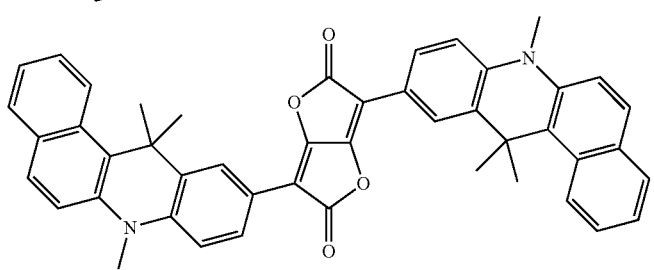
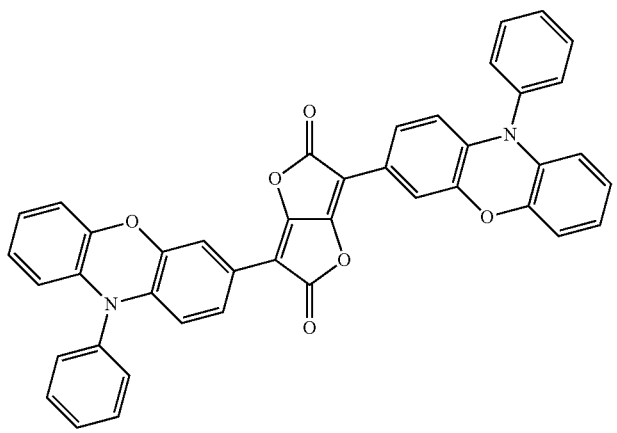
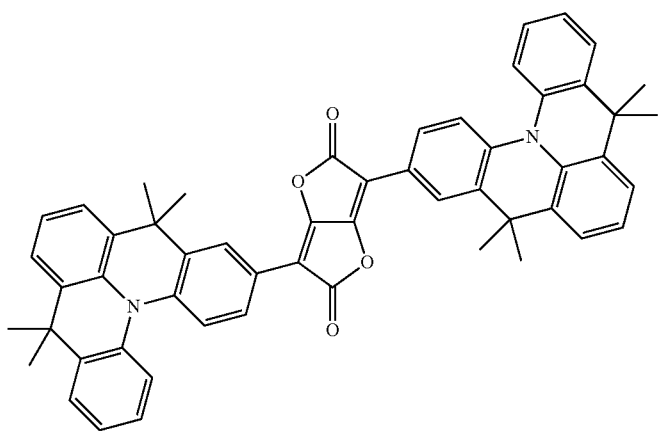

-continued
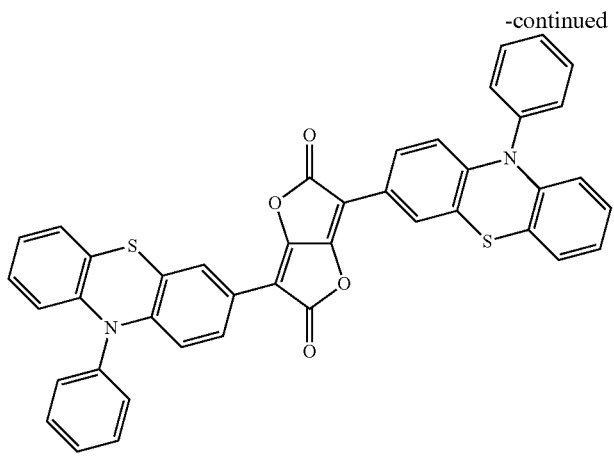
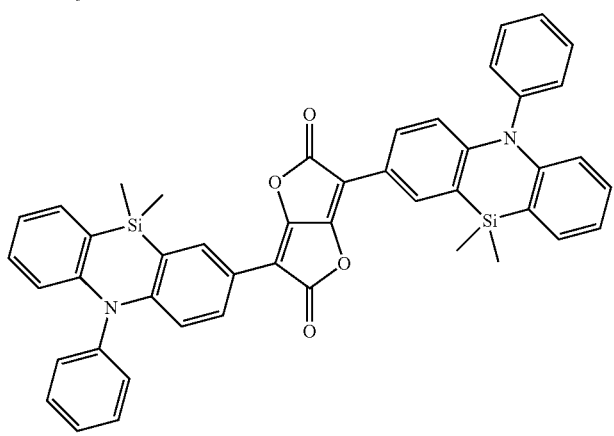
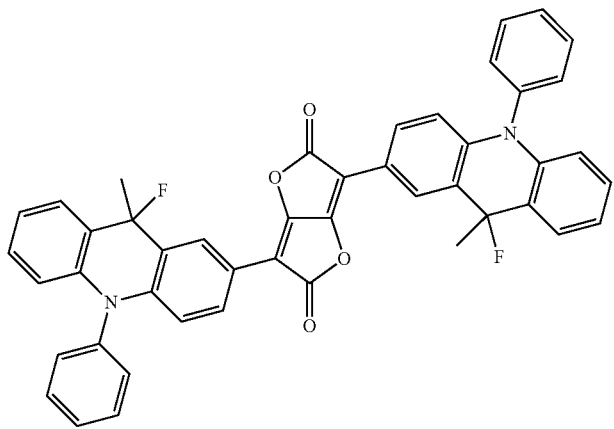
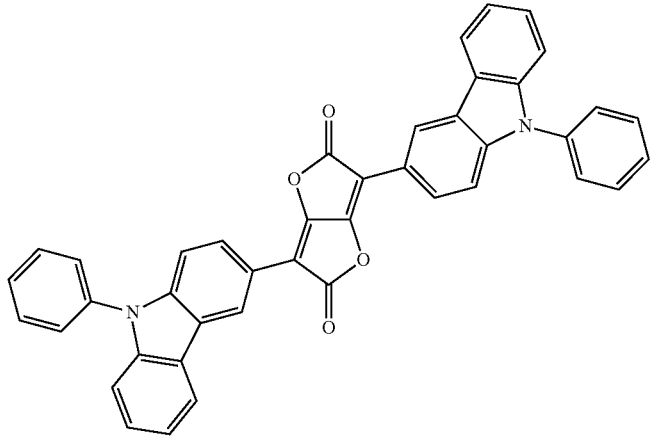

-continued
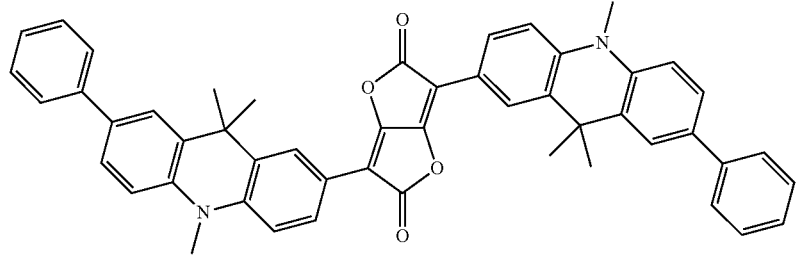
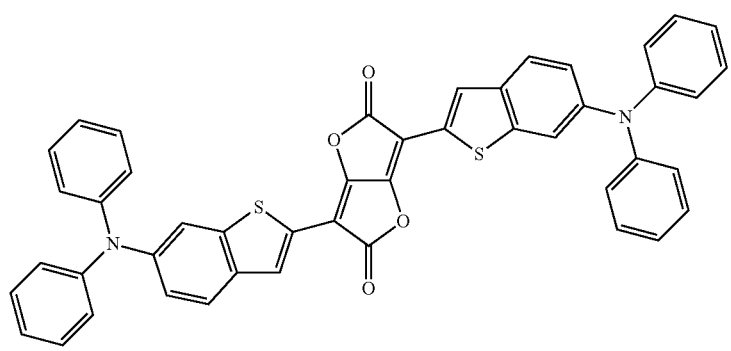
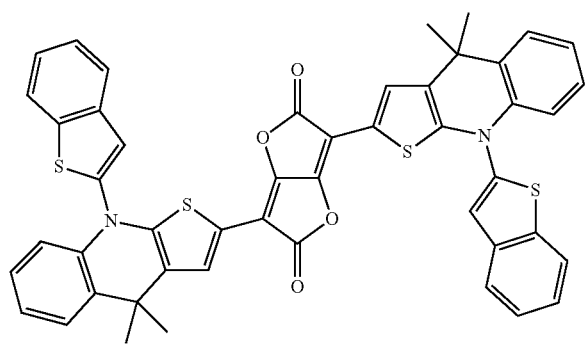
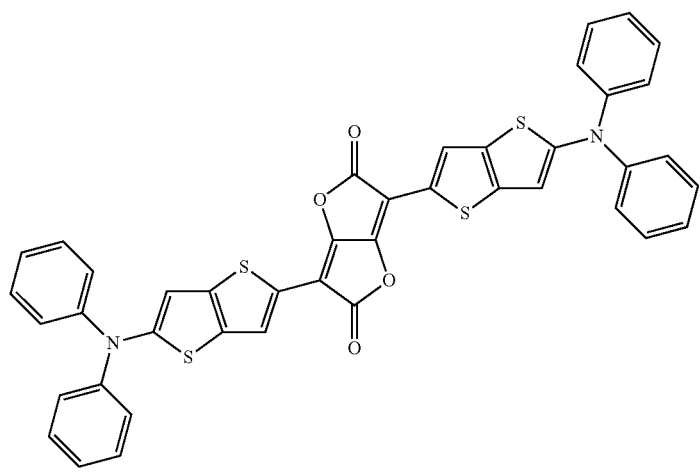

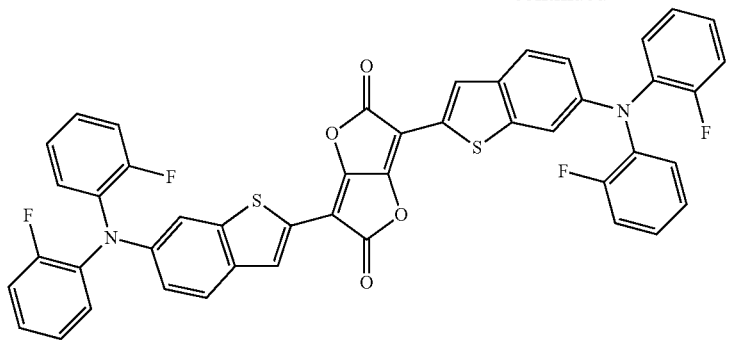
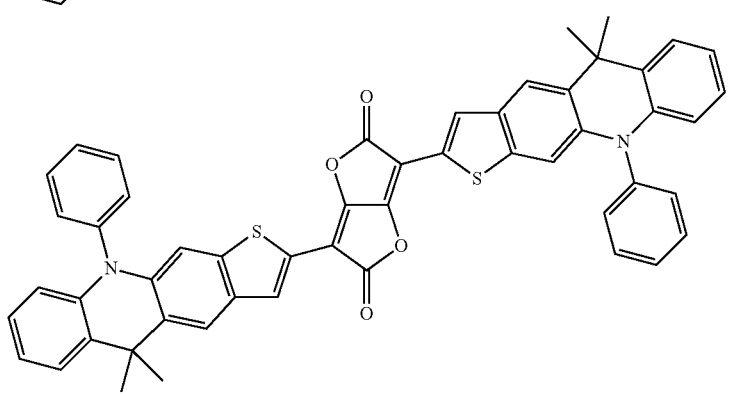
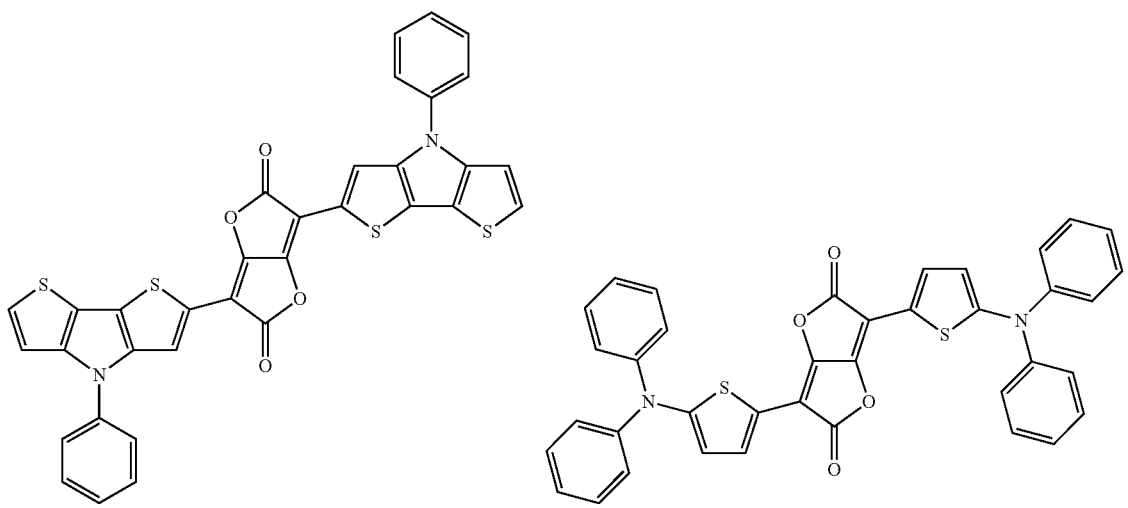
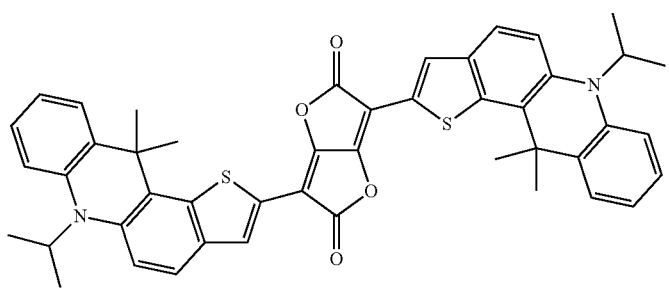

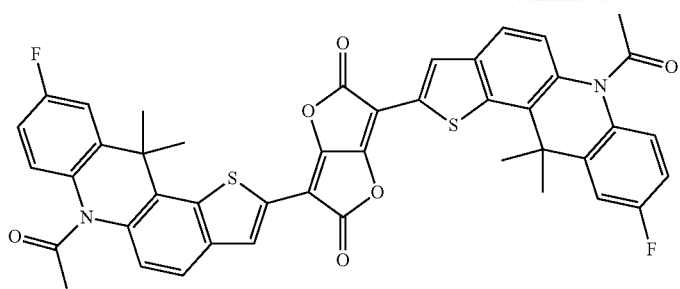
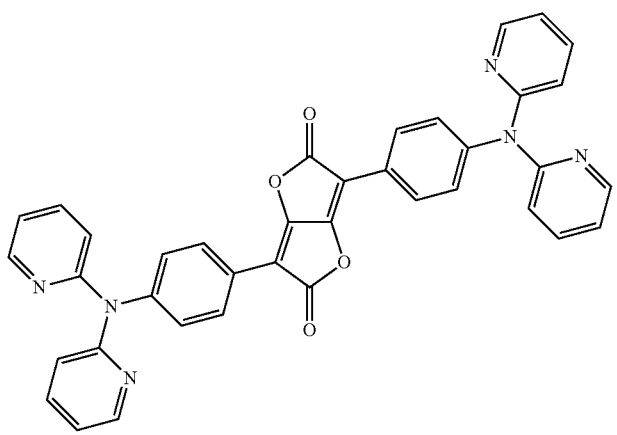
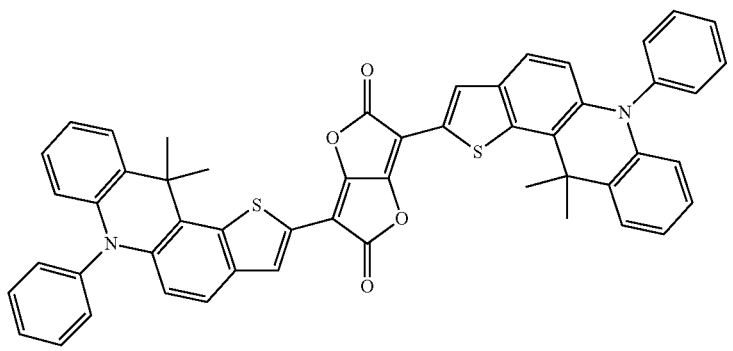
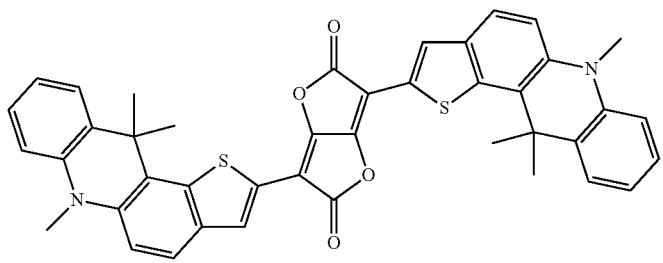

-continued
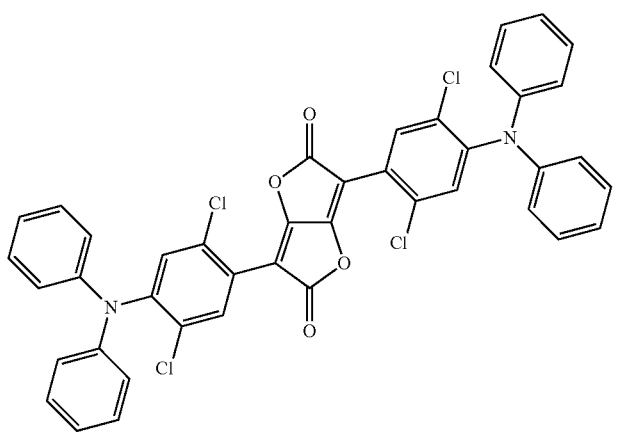
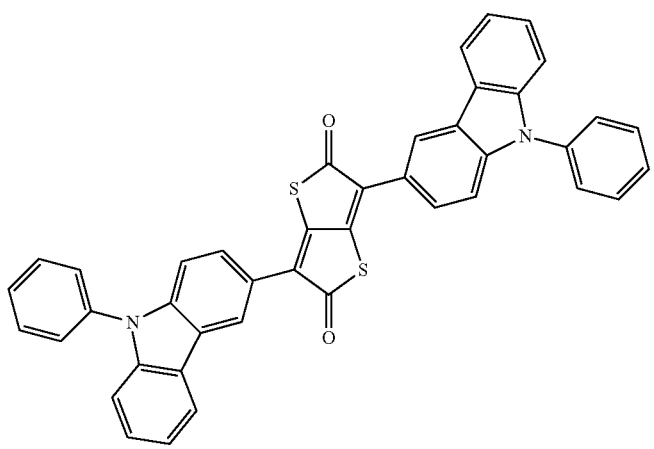
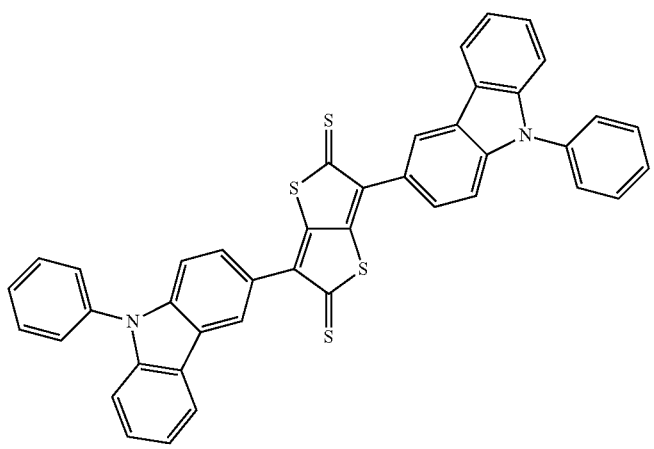

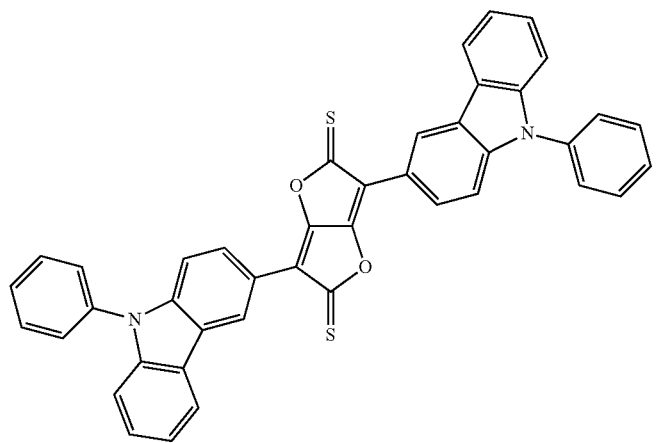
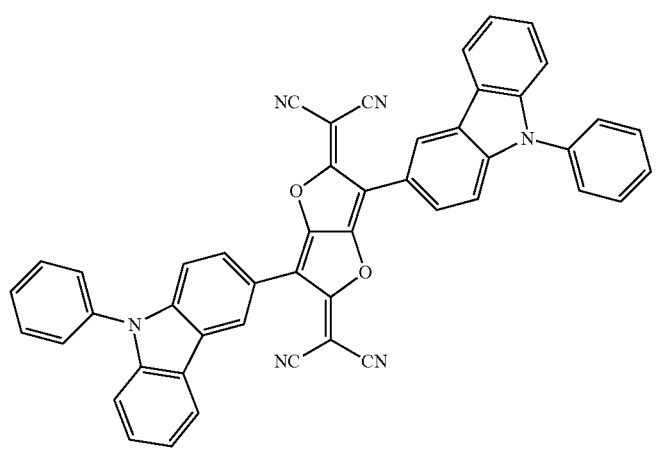
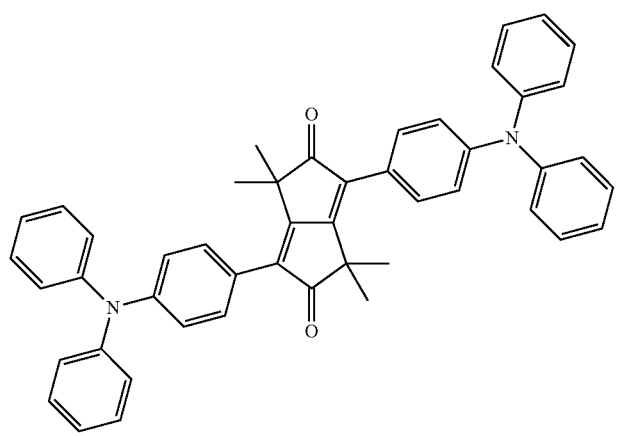

-continued
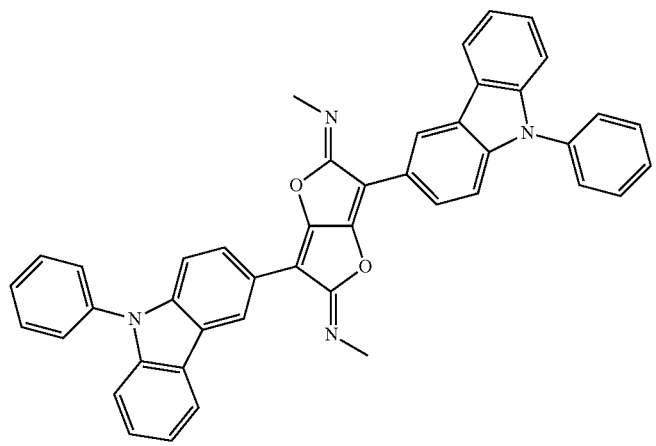
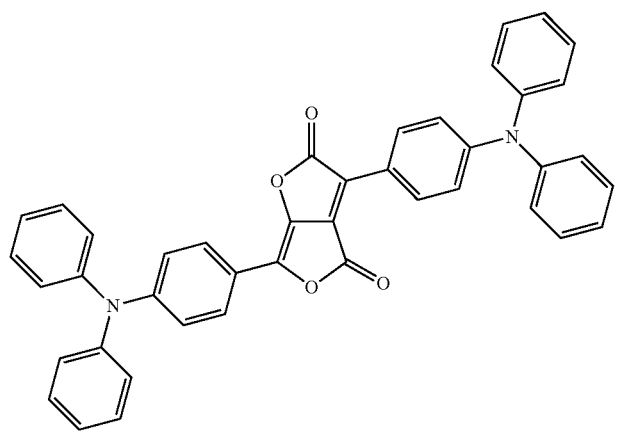
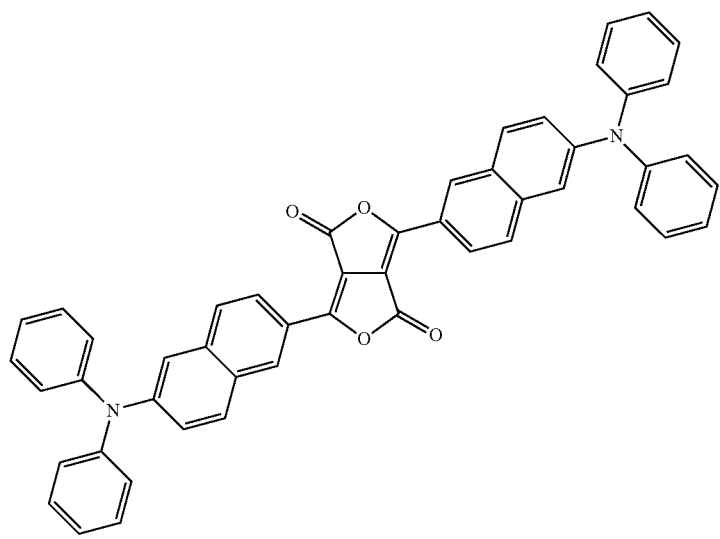

-continued
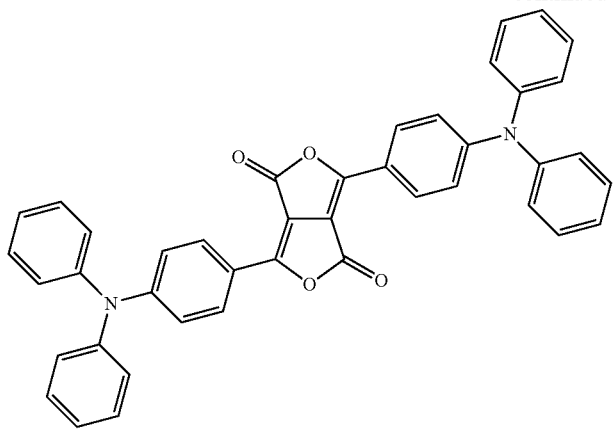
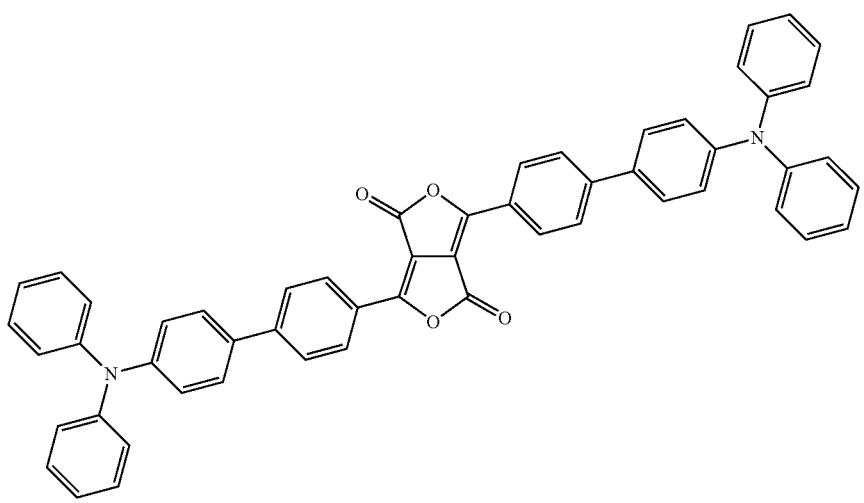
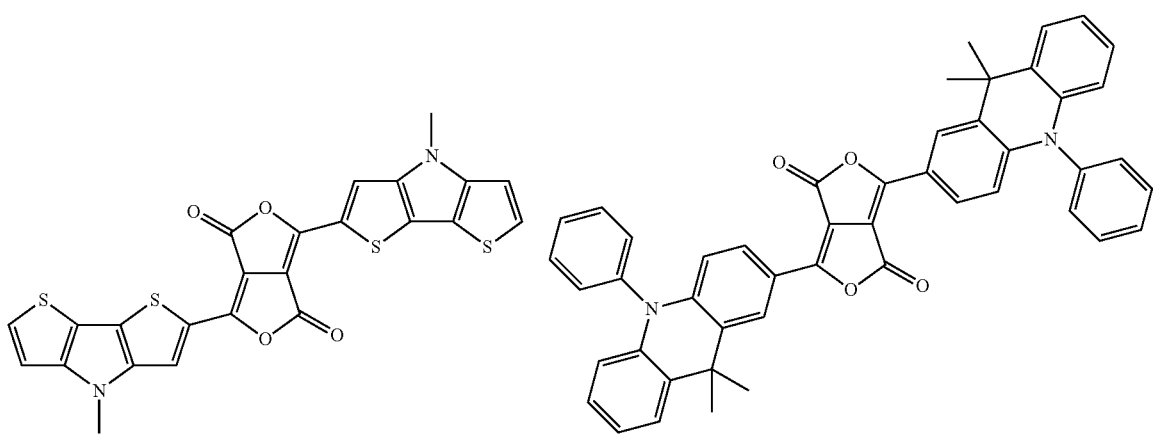

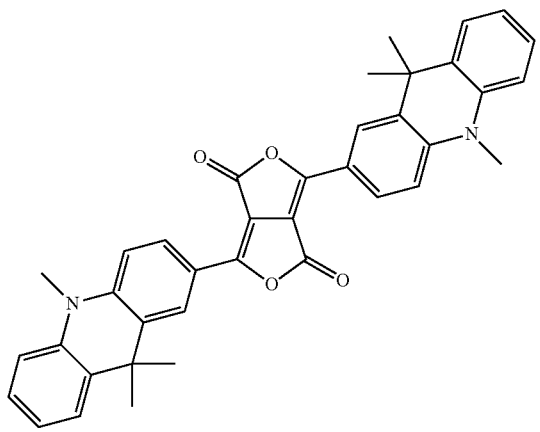
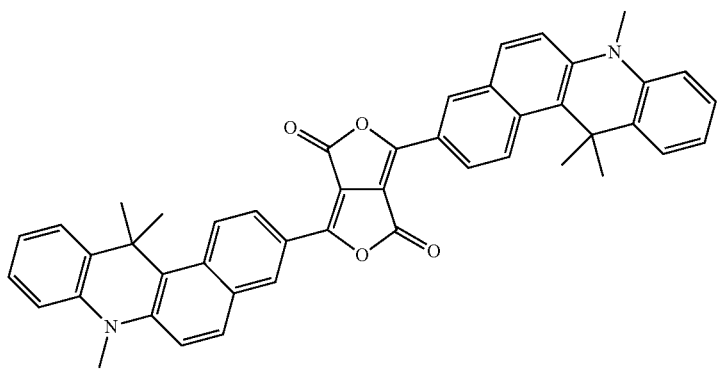
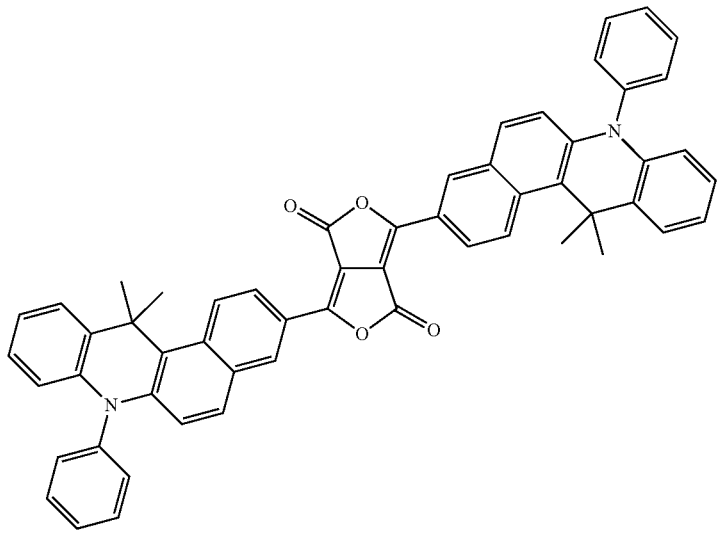
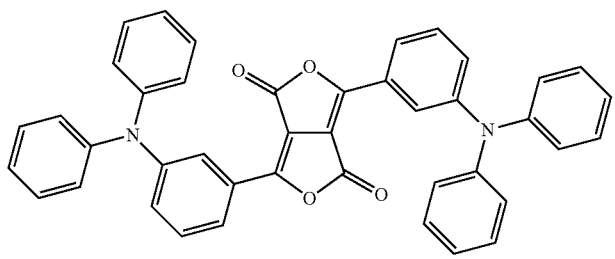

-continued
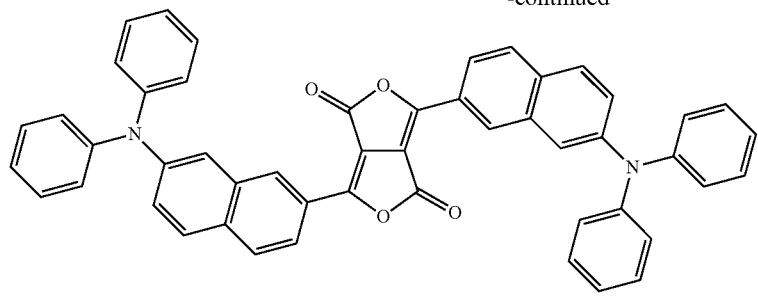
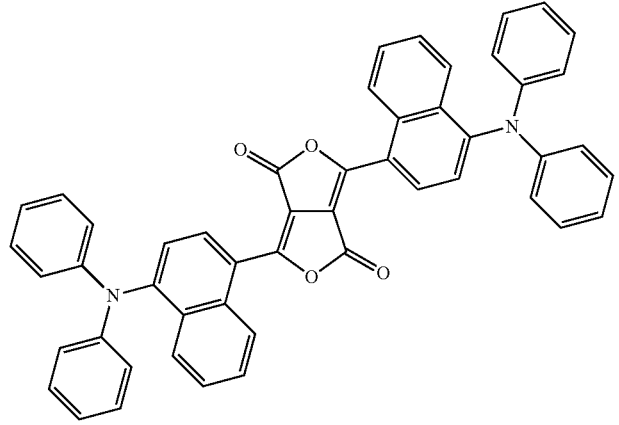
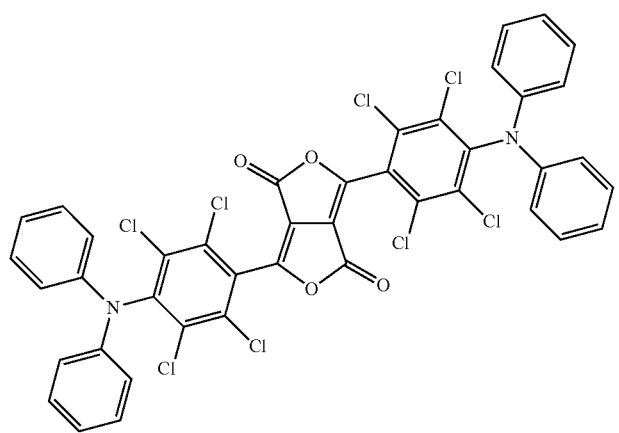
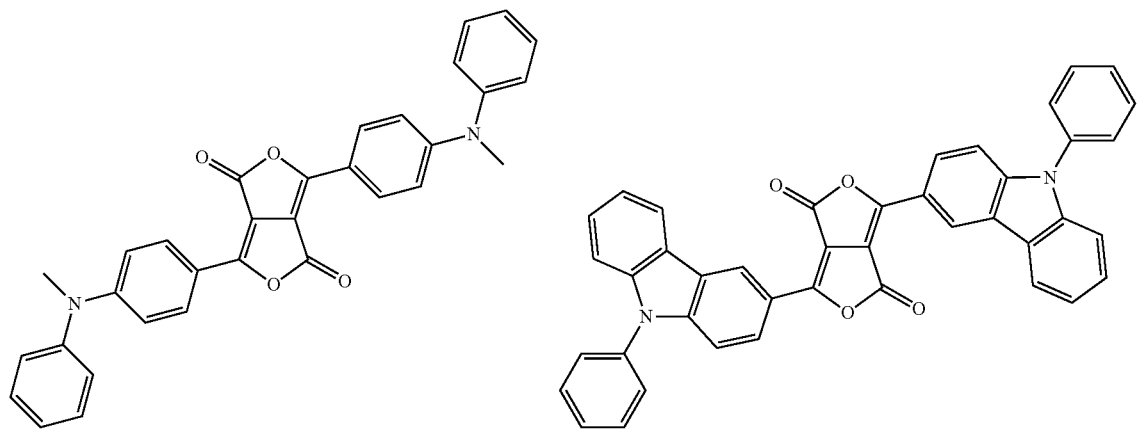

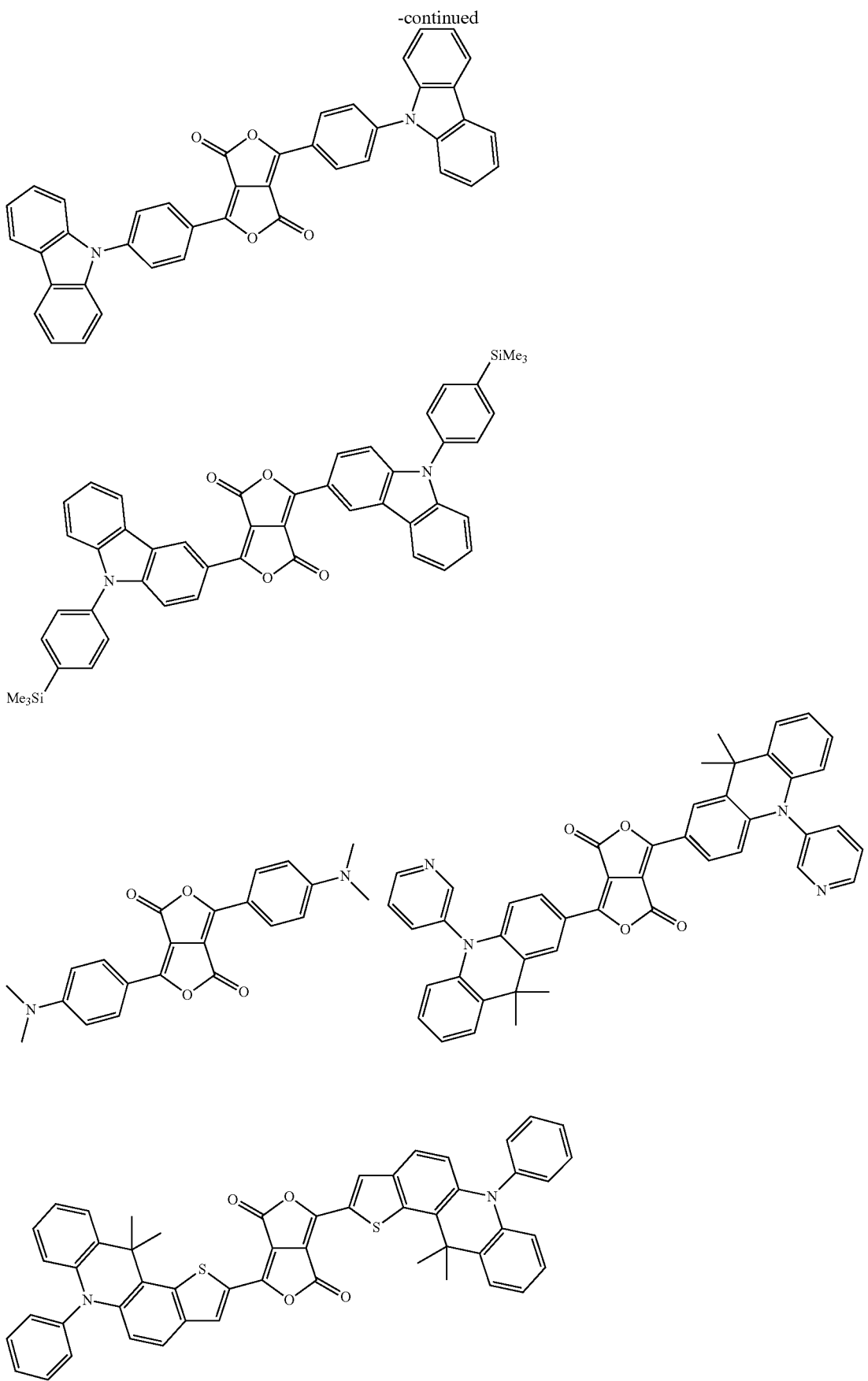

-continued
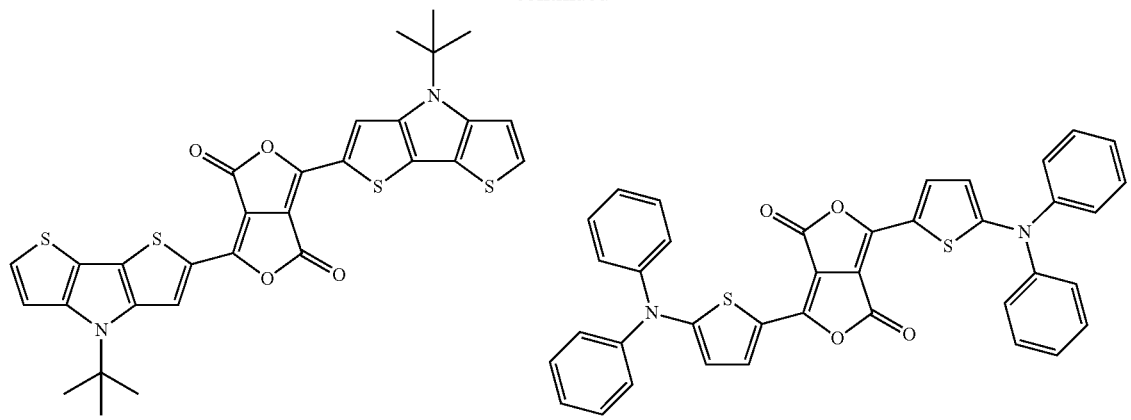
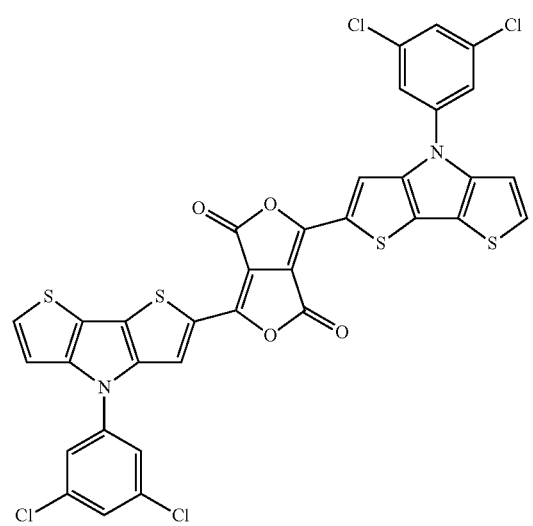
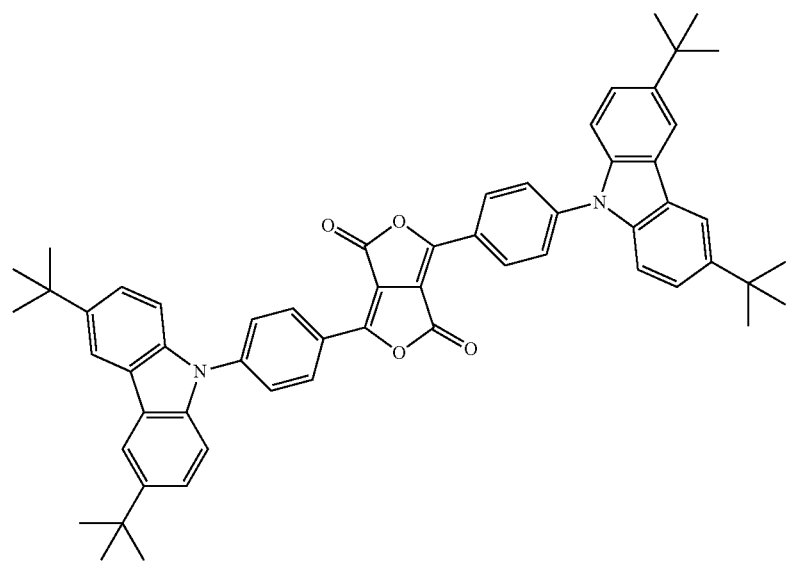

-continued
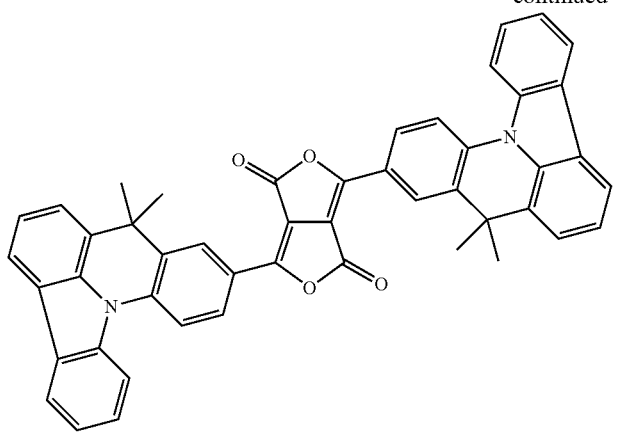
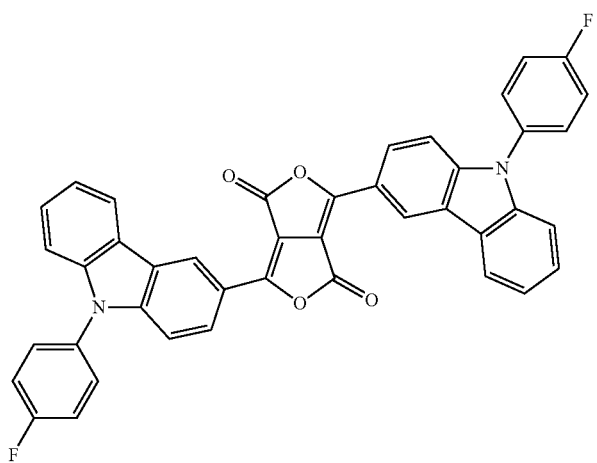
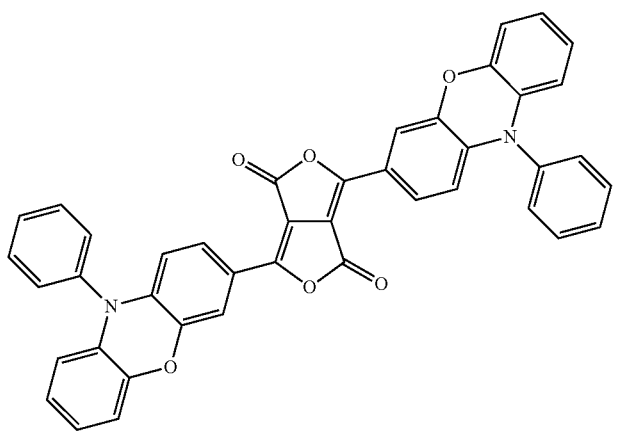

-continued
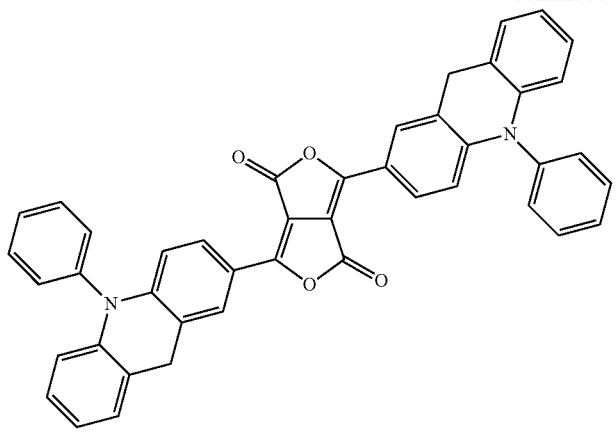
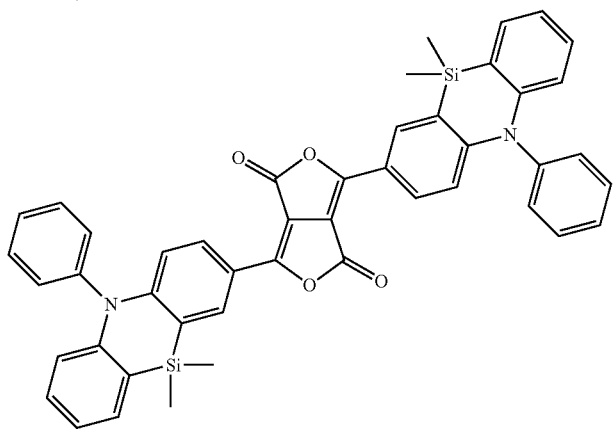
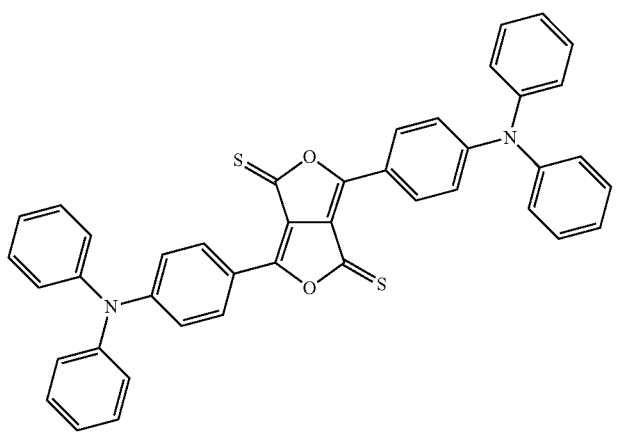
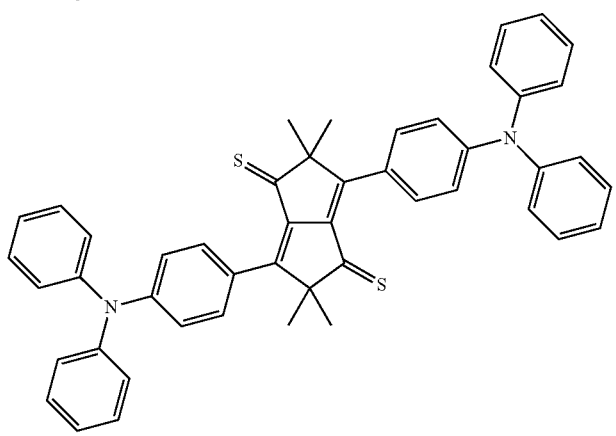

-continued
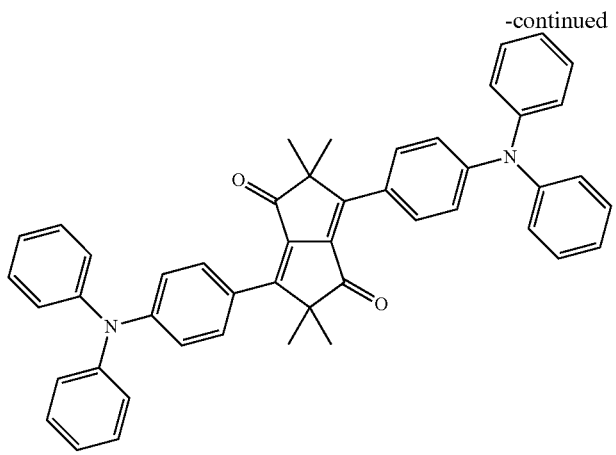
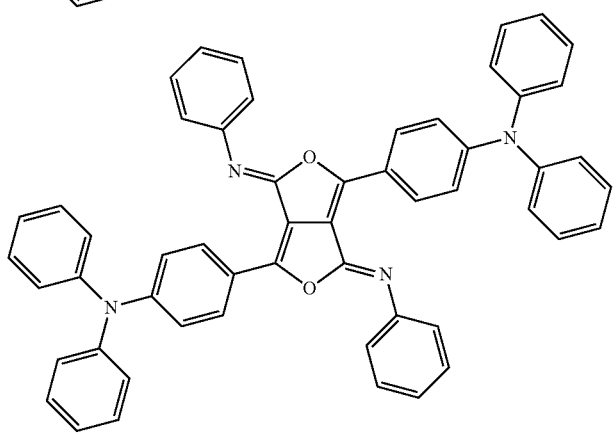
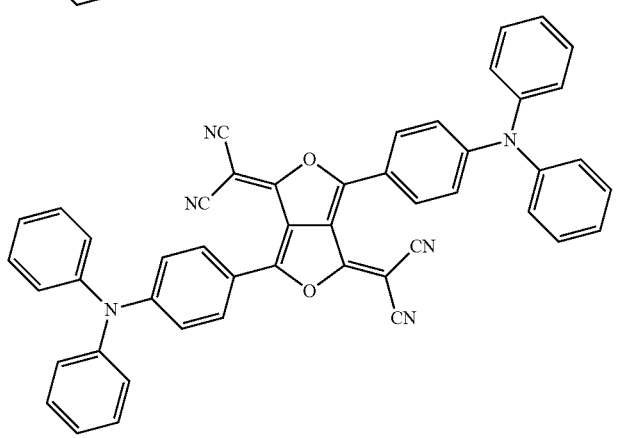
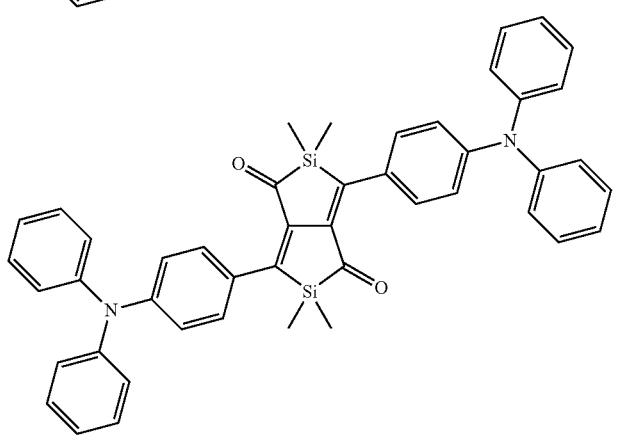

The compound represented by General formula (1), the compound represented by General formula (2), and the compound represented by General formula (3) (hereinafter, these compounds are collectively referred to as a compound X) preferably have an absorption maximum at a wavelength of 400 nm or more but less than 720 nm in an ultraviolet visible absorption spectrum. From the viewpoint of widely absorbing light in the visible region, a peak wavelength (absorption maximum wavelength) of the absorption spectrum is preferably 450 nm or more but 700 nm or less, more preferably 480 nm or more but 700 nm or less, and particularly preferably 510 nm or more but 680 nm or less.

The absorption maximum wavelength of the compound X can be measured using a chloroform solution of the compound X with UV-2550 manufactured by Shimadzu Corporation. The concentration of the chloroform solution is preferably $5\times10^{-5}$ mol/l to $1\times10^{-7}$ mol/l, more preferably $3\times10^{-5}$ mol/l to $2\times10^{-6}$ mol/l, and particularly preferably $2\times10^{-5}$ mol/l to $5\times10^{-6}$ mol/l.

It is preferable for the compound X to have an absorption maximum at a wavelength of 400 nm or more but less than 720 nm in an ultraviolet visible absorption spectrum, and a molar absorption coefficient of the absorption maximum wavelength is preferably equal to or greater than 10,000 $mol^{-1} \cdot l \cdot cm^{-1}$. In order to reduce the film thickness of the photoelectric conversion film and to obtain an element having high charge-collecting efficiency, high speed responsiveness and high sensitivity characteristics, materials having a large molar absorption coefficient are preferable. The molar absorption coefficient of the compound X is more preferably equal to or greater than 20,000 $mol^{-1} \cdot l \cdot cm^{-1}$, and even more preferably equal to or greater than 40,000 $mol^{-1} \cdot l \cdot cm^{-1}$. The molar absorption coefficient of the compound X is measured using the chloroform solution.

The greater the difference between a melting point of the compound X and a vapor deposition temperature thereof (melting point—vapor deposition temperature) is, the harder it is for the compound X to be decomposed at the time of vapor deposition and thus, it is possible to increase the vapor deposition speed with a high vapor deposition temperature. The difference between the melting point and the vapor deposition temperature (melting point—vapor deposition temperature) is preferably equal to or higher than 40° C., more preferably equal to or higher than 50° C., even more preferably equal to or higher than 60° C., and particularly preferably equal to or higher than 80° C.

The molecular weight of the compound X is preferably 300 to 1,500, more preferably 500 to 1,000, and particularly preferably 500 to 900. If the molecular weight of the compound X is equal to or smaller than 1,500, the vapor deposition temperature is not increased, and the compound X is not easily decomposed. If the molecular weight of the compound X is equal to or greater than 300, a glass transition point of a vapor-deposited film is not lowered, and heat resistance of the element does not easily deteriorate.

The glass transition point (Tg) of the compound X is preferably equal to or higher than 95° C., more preferably equal to or higher than 110° C., even more preferably equal to or higher than 135° C., particularly preferably equal to or higher than 150° C., and most preferably equal to or higher than 160° C. The higher the glass transition point, the better, since heat resistance of the element is improved.

The compound X is useful particularly as a material of a photoelectric conversion film used for an imaging device, an optical sensor, or a photoelectric cell. Generally, the compound X functions as a p-type organic compound in the photoelectric conversion film. Moreover, the compound can also be used as a coloring material, a liquid crystal material, a material of an organic semiconductor, a material of an organic light-emitting element, a charge-transporting material, a pharmaceutical material, a material of a fluorescent diagnostic agent, and the like.

(Other Materials)

The photoelectric conversion film may further contain a p-type organic compound or an n-type organic compound as a photoelectric conversion material.

The p-type organic compound (semiconductor) is a donor-type organic compound (semiconductor). This material is mainly represented by a hole transport organic compound and refers to an organic compound that easily donates electrons. More specifically, when two organic materials are brought into contact to each other for use, an organic compound having a smaller ionization potential is called the p-type organic semiconductor. Accordingly, as the donor-type organic compound, any organic compound can be used as long as it has electron-donating properties. For example, it is possible to use a triarylamine compound, a benzidine compound, a pyrazoline compound, a styrylamine compound, a hydrazone compound, a triphenylmethane compound, a carbazole compound, and the like.

The n-type organic compound (semiconductor) is an acceptor-type organic compound (semiconductor). This material is mainly represented by an electron-transporting organic compound and refers to an organic compound that easily accepts electrons. More specifically, when two organic compounds are brought into contact to each other for use, an organic compound showing a higher degree of electron affinity is called the n-type organic compound. Accordingly, as the acceptor-type organic compound, any organic compound can be used as long as it has electron-accepting properties. Preferable examples thereof include fullerenes or fullerene derivatives, fused aromatic carbon ring compounds (naphthalene derivatives, anthracene derivatives, phenanthrene derivatives, tetracene derivatives, pyrene derivatives, perylene derivatives, and fluoranthene derivatives), 5 to 7-membered heterocyclic compounds containing nitrogen atom, oxygen atom, and sulphur atom (for example, pyridine, pyrazine, pyrimidine, pyridazine, triazine, quinoline, quinoxaline, quinazoline, phthalazine, cinnoline, isoquinoline, pteridine, acridine, phenazine, phenanthroline, tetrazole, pyrazole, imidazole, thiazole, oxazole, indazole, benzimidazole, benzotriazole, benzoxazole, benzothiazole, carbazole, purine, triazolopyridazine, triazolopyrimidine, tetrazaindene, oxadiazole, imidazopyridine, pyrrolidine, pyrrolopyridine, thiadiazolopyridine, dibenzazepine, and tribenzazepine), a polyarylene compound, a fluorene compound, a cyclopentadiene compound, a silyl compound, metal complexes having nitrogen-containing heterocyclic compounds as ligands, and the like.

As the aforementioned n-type organic compound, fullerenes or fullerene derivatives are preferable. Fullerenes include fullerene $C_{60}$, fullerene $C_{70}$, fullerene $C_{76}$, fullerene $C_{78}$, fullerene $C_{80}$, fullerene $C_{82}$, fullerene $C_{84}$, fullerene $C_{90}$, fullerene $C_{96}$, fullerene $C_{240}$, fullerene $C_{540}$, and mixed fullerene, and fullerene derivatives refer to compounds obtained when a substituent is added to the fullerenes. As the substituent, alkyl groups, aryl groups, or heterocyclic groups are preferable. As fullerene derivatives, the compounds disclosed in JP 2007-123707 A are preferable.

It is preferable for the photoelectric conversion film to have a bulk-heterojunction structure which is formed in a state where the compound X is mixed with a fullerene or a fullerene derivative. The bulk-heterojunction structure is a layer in which a p-type organic compound (the compound X) and an n-type organic compound are mixed and dispersed. The bulk-heterojunction structure can be formed by either a wet method or a dry method, but it is preferable to form the structure by a co-deposition method. When a heterojunction structure is formed in the photoelectric conversion film, it is possible to make up for a defect of a short carrier diffusion length of the photoelectric conversion film and to improve the photoelectric conversion efficiency of the photoelectric conversion film. The bulk-heterojunction structure is described in detail in paragraphs [0013] and [0014] of JP 2005-303266 A and the like.

In the photoelectric conversion film, a molar ratio of the n-type organic compound to the compound X (n-type organic compound/the compound X) is preferably equal to or greater than 1.0, more preferably 1 or more but 10 or less, and even more preferably 2 or more but 8 or less.

In the photoelectric conversion film, a content ratio of a fullerene-based compound, which is selected from the group consisting of fullerenes and derivatives thereof, to a sum of the fullerene-based compound and the compound X (film thickness of the fullerene-based compound expressed in terms of a single layer/(film thickness of the compound X expressed in terms of a single layer+film thickness of the fullerene-based compound expressed in terms of a single layer)) is not particularly limited. Because the characteristics (photoelectric conversion efficiency, responsiveness and the like) of the photoelectric conversion element are further improved, the content ratio is preferably equal to or greater than 50% by volume, and more preferably 60% by volume to 90% by volume.

Herein, the film thickness of the compound X expressed in terms of a single layer means the film thickness of one or more of the compounds represented by General formulae (1) to (3) expressed in terms of a single layer. For example, when only the compound represented by General formula (1) is used, the film thickness means the film thickness of the compound represented by General formula (1) expressed in terms of a single layer. When the compounds represented by General formulae (1) to (3) are used, the film thickness means the total film thickness of the three compounds expressed in terms of a single layer.

The photoelectric conversion film containing the compound X of the present invention (an n-type organic compound may also be mixed into the film) is a non-luminescent film, and has characteristics different from those of an organic electroluminescent device (OLED). The non-luminescent film refers to a film having a luminescent quantum efficiency equal to or lower than 1%. The luminescent quantum efficiency is preferably equal to or lower than 0.5%, and more preferably equal to or lower than 0.1%.

(Film Forming Method)

The photoelectric conversion film 12 can be formed by a dry film formation method or a wet film formation method. Specific examples of the dry film formation method include physical vapor deposition methods such as a vacuum vapor deposition method, a sputtering method, an ion plating method, and an MBE method; and CVD methods such as plasma polymerization. As the wet film formation method, a casting method, a spin coating method, a dipping method, an LB method, and the like are used. Among these, dry film formation methods are preferable, and a vacuum vapor deposition method is more preferable. When the vacuum vapor deposition method is used for forming a film, production conditions including a degree of vacuum and a vapor deposition temperature can be set according to common methods.

At the time of manufacturing the photoelectric conversion film containing the compound X, it is preferable to manufacture the film by using a vapor deposition method.

Generally, it is preferable for the vapor deposition rate to be high because the productivity is further improved. However, when the vapor deposition rate is high, a thermal load applied to the compound increases. Consequently, if the vapor deposition rate is increased, the dark current characteristics of the manufactured photoelectric conversion element deteriorate in some cases.

In contrast, if the compound X is used, even when the vapor deposition rate is increased, the dark current characteristics of the manufactured photoelectric conversion element deteriorate less. In particular, in a case where a fused ring structure is contained in the compound X (for example, in a case where $R^{30}$ and $R^{31}$, $R^{30}$ and $R^{32}$, or $R^{31}$ and $R^{32}$ in General formula (14) form a ring by being directly bonded to each other or by being bonded to each other through a linking group), the deterioration of the dark current characteristics is further suppressed. The fact that the deterioration of the dark current characteristics is suppressed as above means that the compound has high heat resistance. Moreover, the fact that the vapor deposition rate can be increased means that the mass productivity can be further increased, and that the manufacture latitude is wide (the range of the applicable vapor deposition rate is wide), and accordingly, it can be said that the compound X is more suitable for industrial production.

The range of the vapor deposition rate is not particularly limited, and is preferably equal to or greater than 0.5 Å/sec, more preferably equal to or greater than 1 Å/sec, and even more preferably equal to or greater than 2 Å/sec.

The thickness of the photoelectric conversion film 12 is preferably 10 nm or more but 1,000 nm or less, more preferably 50 nm or more but 800 nm or less, and particularly preferably 100 nm or more but 600 nm or less. If the thickness of the photoelectric conversion film 12 is 10 nm or more, a preferable effect of suppressing dark currents is obtained, and if the thickness of the photoelectric conversion film 12 is 1,000 nm or less, preferable photoelectric conversion efficiency is obtained.

[Electrode]

The electrodes (the upper electrode (transparent conductive film) 15 and the lower electrode (conductive film) 11) are composed of a conductive material. As the conductive material, a metal, an alloy, a metal oxide, an electroconductive compound, a mixture of these, and the like can be used.

Since light enters the photoelectric conversion element from the upper electrode 15, the upper electrode 15 needs to be sufficiently transparent with respect to light to be detected. Specific examples of the material of the upper electrode 15 include conductive metal oxides such as tin oxide doped with antimony, fluorine, or the like (ATO or FTO), tin oxide, zinc oxide, indium oxide, indium tin oxide (ITO), and indium zinc oxide (IZO); thin films of metals such as gold, silver, chromium, and nickel; mixtures or laminates composed of the metals and conductive metal oxides described above; inorganic conductive substances such as copper iodide and copper sulphide; organic conductive materials such as polyaniline, polythiophene, and polypyrrole; laminates composed of these materials and ITO; and the like. Among these, in view of high conductivity, transparency, and the like, transparent conductive metal oxides are preferable.

Generally, when the thickness of the conductive film is decreased to be out of a certain range, a value of resistance rapidly increases. However, in a solid-state imaging device including the photoelectric conversion element according to the present embodiment, a sheet resistance may be preferably 100 Ω/square to 10,000 Ω/square, and the film thickness can be small within a range set with a high degree of freedom. In addition, the thinner the upper electrode (transparent conductive film) 15 is, the smaller the amount of absorbed light becomes, and a light transmittance is increased in general. The increase in light transmittance is extremely preferable since the amount of light absorbed at the photoelectric conversion film 12 is increased, and thus a photoelectric conversion ability is enhanced. Considering the suppression of leakage current, increase in a value of resistance of the thin film, and increase in the transmittance that result from reduction of film thickness, the film thickness of the upper electrode 15 is preferably 5 nm to 100 nm, and more preferably 5 nm to 20 nm.

Depending on the intended use, in some cases transparency is provided to the lower electrode 11, whereas in some cases a light-reflecting material is used for the lower electrode 11 instead of providing transparency thereto. Specific examples of the material of the lower electrode 11 include conductive metal oxides such as tin oxide doped with antimony, fluorine, or the like (ATO or FTO), tin oxide, zinc oxide, indium oxide, indium tin oxide (ITO), and indium zinc oxide (IZO); metals such as gold, silver, chromium, nickel, titanium, tungsten, and aluminium; conductive compounds such as oxides or nitrides of the aforementioned metals (for example, titanium nitride (TiN)); mixtures or laminates composed of the aforementioned metals and conductive metal oxides; inorganic conductive substances such as copper iodide and copper sulphide; organic conductive materials such as polyaniline, polythiophene, and polypyrrole; laminates composed of these materials and ITO or titanium nitride; and the like.

A method for forming the electrodes is not particularly limited, and can be appropriately selected according to the electrode material. Specifically, the electrodes can be formed by a wet method such as a printing method or a coating method, a physical method such as a vacuum vapor deposition method, a sputtering method, and an ion plating method, a chemical method such as CVD or a plasma CVD method, and the like.

When ITO is used as the electrode material, the electrodes can be formed by methods such as an electron beam method, a sputtering method, a resistance heating type vapor deposition method, a chemical reaction method (a sol-gel method or the like), and application of a dispersion of indium tin oxide. Moreover, UV-ozone processing, plasma processing, or the like can be performed on the film prepared using ITO. When TiN is used as the electrode material, various methods including a reactive sputtering method are used, and UV-ozone processing, plasma processing, or the like can be further performed.

[Charge Blocking Film: Electron Blocking Film, Hole Blocking Film]

The photoelectric conversion element of the present invention may have a charge blocking film. If the photoelectric conversion element has such a film, the characteristics (photoelectric conversion efficiency, responsiveness, and the like) of the obtained photoelectric conversion element are further improved. Examples of the charge blocking film include an electron blocking film and a hole blocking film. Hereinafter, each of the films will be described in detail.

(Electron Blocking Film)

Electron-donating organic materials can be used for the electron blocking film. Specifically, as low-molecular weight materials, it is possible to use aromatic diamine compounds such as N,N'-bis(3-methylphenyl)-(1,1'-biphenyl)-4,4'-diamine (TPD) and 4,4'-bis[N-(naphthyl)-N-phenyl-amino]biphenyl (α-NPD), oxazole, oxadiazole, triazole, imidazole, imidazolone, stilbene derivatives, pyrazoline derivatives, tetrahydroimidazole, polyarylalkane, butadiene, 4,4',4''-tris(N-(3-methylphenyl)-N-phenylamino)triphenylamine (m-MTDATA), porphyrin compounds such as porphine, tetraphenylporphyrin copper, phthalocyanine, copper phthalocyanine, and titanium phthalocyanine oxide, triazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, oxazole derivatives, styrylanthracene derivatives, fluorenone derivatives, hydrazone derivatives, silazane derivatives, and the like. As high-molecular weight materials, it is possible to use polymers such as phenylene vinylene, fluorene, carbazole, indole, pyrene, pyrrole, picoline, thiophene, acetylene, and diacetylene and derivatives of these. The compounds that are not electron-donating compounds can also be used as long as they have sufficient hole transport properties. Specifically, the compounds are preferable which are described in paragraphs [0083] to [0089] of JP 2008-72090 Å, paragraphs [0043] to [0063] of JP 2011-176259 Å, paragraphs [0121] to [0148] of JP 2011-228614 Å, and paragraphs [0108] to [0156] of JP 2011-228615 Å.

Furthermore, in particular, the electron blocking film preferably contains the compound represented by General formula (F-1) described in paragraphs [0068] to [0094] of JP 2013-012535 A or the compound represented by General formula (i) described in paragraphs [0043] to [0063] of JP 2011-176259 Å. The contents of the aforementioned documents are incorporated in the present specification by reference.

The electron blocking film may be composed of plural films.

As the electron blocking film, inorganic materials can also be used. Generally, inorganic materials have a higher dielectric constant compared to organic materials. Accordingly, when an inorganic material is used for the electron blocking film, higher voltage is applied to the photoelectric conversion film, and hence the photoelectric conversion efficiency can be improved. Examples of materials that can form the electron blocking film include calcium oxide, chromium oxide, copper-chromium oxide, manganese oxide, cobalt oxide, nickel oxide, copper oxide, copper-gallium oxide, copper-strontium oxide, niobium oxide, molybdenum oxide, copper-indium oxide, silver-indium oxide, iridium oxide, and the like. When the electron blocking film is constituted of a single layer, the layer can be formed of an inorganic material, or when the electron blocking film is constituted of plural layers, one layer or two or more layers can be formed of an inorganic material.

(Hole Blocking Film)

For the hole blocking film, an electron-accepting organic material can be used.

As the electron-accepting material, it is possible to use oxadiazole derivatives such as 1,3-bis(4-tert-butylphenyl-1,3,4-oxadiazolyl)phenylene (OXD-7), anthraquinodimethane derivatives, diphenylquinone derivatives, bathocuproin, bathophenanthroline, derivatives of these, a triazole compound, a tris(8-hydroxyquinolinato)aluminum complex, a bis(4-methyl-8-quinolinato)aluminum complex, distyrylarylene derivatives, a silole compound, and the like. Moreover, materials other than the electron-accepting organic materials can also be used as long as the materials exhibit sufficient electron transporting properties. For example, a porphyrin-based compound, a styryl-based compound such as DCM (4-dicyanomethylene-2-methyl-6-(4-(dimethylaminostyryl))-4H pyran), a 4H pyran-based compound can be used. Specifically, the compounds described in paragraphs [0073] to [0078] of JP 2008-72090 A are preferable.

A method for producing the charge blocking film is not particularly limited, and the charge blocking film can be formed by a dry film formation method or a wet film formation method. As the dry film formation method, it is possible to use a vapor deposition method, a sputtering method, and the like. The vapor deposition may be physical vapor deposition (PVD) or chemical vapor deposition (CVD), but among these, physical vapor deposition such as vacuum vapor deposition is preferable. As the wet film formation method, it is possible to use an inkjet method, a spraying method, a nozzle printing method, a spin coating method, a dip coating method, a casting method, a die coating method, a roll coating method, a bar coating method, a gravuer coating method, and the like. Among these, from the viewpoint of high-accuracy patterning, an inkjet method is preferable.

A thickness of each of the charge blocking films (the electron blocking film and the hole blocking film) is preferably 10 nm to 200 nm, more preferably 20 nm to 150 nm, and particularly preferably 30 nm to 100 nm. This is because if the thickness is too small, the dark current suppressing effect is diminished, and if it is too large, the photoelectric conversion efficiency decreases.

[Substrate]

The photoelectric conversion element may further include a substrate. The type of the substrate to be used is not particularly limited, and it is possible to use a semiconductor substrate, a glass substrate, or a plastic substrate.

The position of the substrate is not particularly limited. Generally, on the substrate, a conductive film, a photoelectric conversion film, and a transparent conductive film are laminated on one another in this order.

[Sealing Layer]

The photoelectric conversion element may further include a sealing layer. Due to the presence of water molecules or the like that cause deterioration of the photoelectric conversion material, performance of the material markedly deteriorates in some cases. When the entire photoelectric conversion film is covered and sealed with a dense sealing layer composed of a ceramic such as metal oxide, metal nitride or metal nitride oxide, or diamond-like carbon (DLC), which does not allow water molecules to permeate the film, the deterioration described above can be prevented.

The selection of the material of the sealing layer and production of the sealing layer may be performed according to the description in paragraphs [0210] to [0215] of JP 2011-082508 Å.

[Optical Sensor]

The photoelectric conversion element of the present invention can be used as, for example, a photoelectric cell and an optical sensor. It is preferable for the photoelectric conversion element of the present invention to be used as an optical sensor. The optical sensor may use only a single photoelectric conversion element. Alternatively, the optical sensor may be preferably in the form of a line sensor in which the photoelectric conversion elements are arranged in a straight line, or in the form of a two-dimensional sensor in which the photoelectric conversion elements are arranged on a plane. In a line sensor, the photoelectric conversion element of the present invention functions as an imaging device by converting optical image information into electric signals by using an optical system and a driving portion like a scanner or the like. In a two-dimensional sensor, the photoelectric conversion element of the present invention functions as an imaging device by converting optical image information into electric signal by forming an image on the sensor by using an optical system like an imaging module.

A photoelectric cell is a power-generating apparatus. Accordingly, efficiency in converting light energy into electric energy is regarded as important performance, but dark currents which are electric currents generated in a dark place do not cause a problem in the performance thereof. Moreover, the photoelectric cell does not require a heating process at the late stage such as installation of a color filter. For the optical sensor, conversion of brightness signals into electric signals with a high accuracy is regarded as important performance, and consequentially, efficiency in converting the amount of light into electric current is also important performance. However, when being output in a dark place, the signals become noise, and accordingly, dark currents at a low level are required. Furthermore, the resistance to the process of a late stage is also important.

[Imaging Device]

Next, an example of a configuration of an imaging device having the photoelectric conversion element 10a will be described.

In the example of a configuration described below, members and the like having the same configuration and function as the members and the like which have already been described are marked with the same signs or corresponding signs in the drawing, and description thereof is simplified or skipped.

An imaging device is a device that converts optical information of an image into electric signals. In this device, plural photoelectric conversion elements are arranged in a matrix form in the same plane. An optical signal is converted into an electric signal in each of the photoelectric conversion elements (pixels), and the electric signals are sequentially output outside the imaging device for each pixel. Accordingly, each pixel is constituted of one photoelectric conversion element and one or more transistors.

Figure 2:
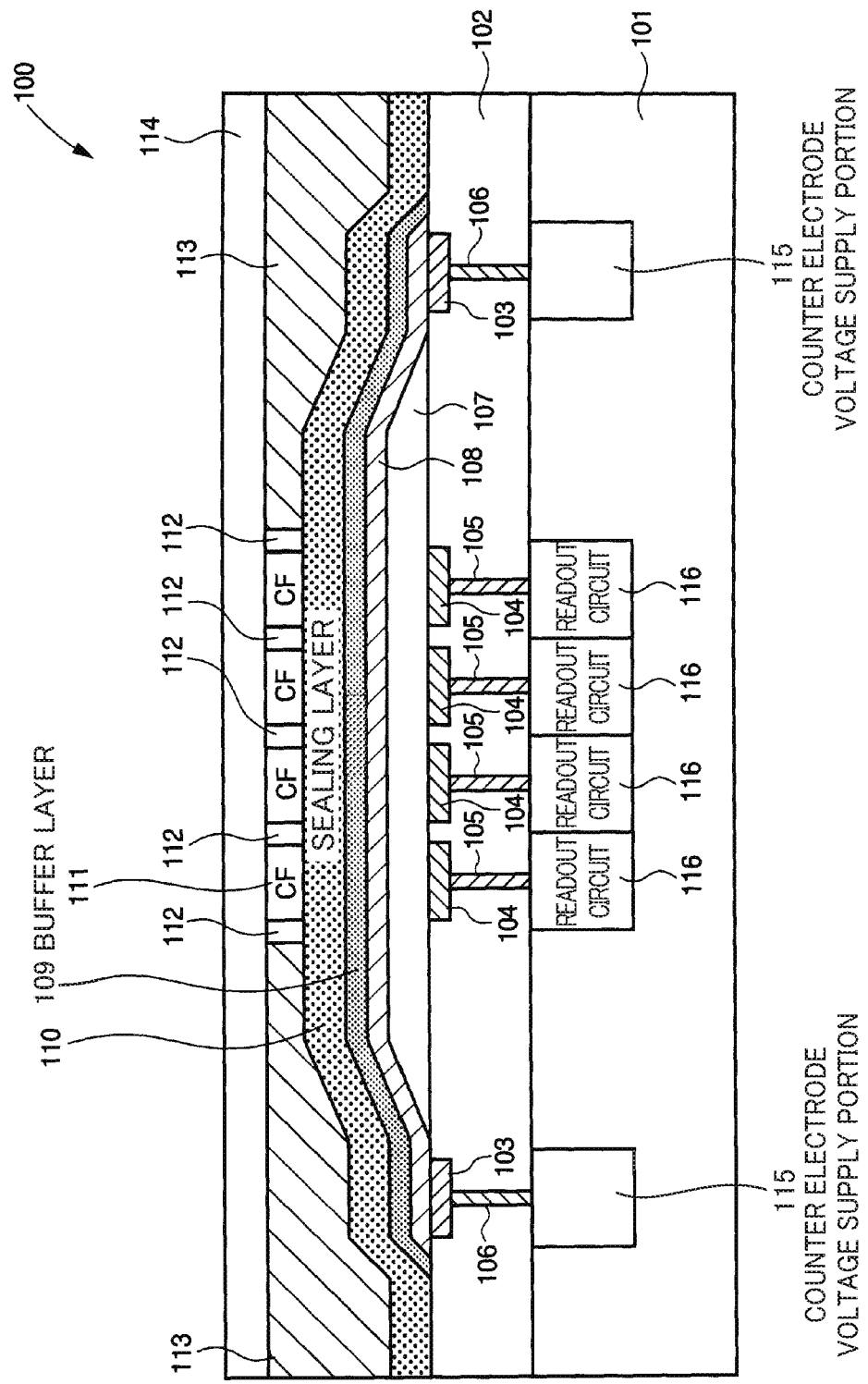
FIG. 2 is a schematic cross-sectional view of one pixel of an imaging device.

FIG. 2 is a cross-sectional view showing a schematic configuration of an imaging device for describing an embodiment of the present invention. The imaging device is mounted on an imaging apparatus such as a digital camera or a digital video camera, an electronic endoscope, an imaging module of a cellular phone, and the like for use.

The imaging device has plural photoelectric conversion elements configured as shown in FIG. 1, and a circuit board on which readout circuits that read out signals corresponding to the charge generated at the photoelectric conversion film of each photoelectric conversion element are formed. The imaging device has a configuration in which plural photoelectric conversion elements are arranged one-dimensionally or two-dimensionally on the same plane positioned above the circuit board.

An imaging device 100 shown in FIG. 2 has a substrate 101, an insulating layer 102, connection electrodes 103, pixel electrodes (lower electrodes) 104, connection portions 105, connection portions 106, a photoelectric conversion film 107, a counter electrode (upper electrode) 108, a buffer layer 109, a sealing layer 110, color filters (CFs) 111, partitions 112, a light-shielding layer 113, a protective layer 114, counter electrode voltage supply portions 115, and readout circuits 116.

The pixel electrodes 104 have the same function as the lower electrode 11 of the photoelectric conversion element 10a shown in FIG. 1. The counter electrode 108 has the same function as the upper electrode 15 of the photoelectric conversion element 10a shown in FIG. 1. The photoelectric conversion film 107 has the same configuration as the film disposed between the lower electrode 11 and the upper electrode 15 in the photoelectric conversion element 10a shown in FIG. 1.

The substrate 101 is a glass substrate or a semiconductor substrate formed of, for example, Si. The insulating layer 102 is formed on the substrate 101. At the surface of the insulating layer 102, the plural pixel electrodes 104 and the plural connection electrodes 103 are formed.

The photoelectric conversion film 107 is a film that is disposed on the plural pixel electrodes 104 to cover the electrodes and shared by all of the photoelectric conversion elements.

The counter electrode 108 is one electrode that is disposed on the photoelectric conversion film 107 and shared by all of the photoelectric conversion elements. The counter electrode 108 is formed such that it reaches the top of each connection electrode 103 disposed outside the photoelectric conversion film 107, and is electrically connected to the connection electrode 103.

The connection portions 106 are embedded in the insulating layer 102, and are each a plug or the like for electrically connecting the connection electrode 103 to the counter electrode voltage supply portion 115. The voltage supply portions 115 are formed in the substrate 101, and each apply predetermined voltage to the counter electrode 108 through the connection portion 106 and the connection electrode 103. When the voltage that should be applied to the counter electrode 108 is higher than the power supply voltage of the imaging device, the voltage supply portion 115 supplies the predetermined voltage by increasing the power supply voltage by using a boosting circuit such as a charge pump.

The readout circuits 116 are disposed in the substrate 101 to correspond to the respective plural pixel electrodes 104, and each read out the signal corresponding to the charge collected by the corresponding pixel electrode 104. The readout circuit 116 is constituted of, for example, a CCD, a CMOS circuit, or a TFT circuit, and is shielded from light by a light-shielding layer (not shown in the drawing) disposed inside the insulating layer 102. The readout circuit 116 is electrically connected to the pixel electrode 104 corresponding thereto through the connection portion 105.

The buffer layer 109 is formed on the counter electrode 108 while covering the counter electrode 108. The sealing layer 110 is formed on the buffer layer 109 while covering the buffer layer 109. The color filters 111 are formed on the sealing layer 110 in positions facing the respective pixel electrodes 104. The partitions 112 are each disposed between color filters 111 and provided for increasing light transmitting efficiency of the color filter 111.

The light-shielding layer 113 is formed on the sealing layer 110 to cover the regions other than the regions where the color filters 111 and the partitions 112 are disposed. The light-shielding layer 113 prevents light from entering the photoelectric conversion film 107 formed in the regions other than the effective pixel regions. The protective layer 114 is formed on the color filters 111, the partitions 112, and the light-shielding layer 113 and protects the entire imaging device 100.

When light enters the imaging device 100 configured as above, the light enters the photoelectric conversion film 107 to generate charges. Among the generated charges, holes are collected by the pixel electrodes 104, and voltage signals corresponding to the amount of the holes are output outside the imaging device 100 by the readout circuits 116.

A method for producing the imaging device 100 is as follows.

On the circuit board in which the counter electrode voltage supply portions 115 and the readout circuits 116 are formed, the connection portions 105 and 106, the plural connection electrodes 103, the plural pixel electrodes 104, and the insulating layer 102 are formed. The plural pixel electrodes 104 are arranged on the surface of the insulating layer 102 in the form of, for example, a square lattice.

Thereafter, on the plural pixel electrodes 104, the photoelectric conversion film 107 is formed by, for example, a vacuum heating vapor deposition method. Then, on the photoelectric conversion film 107, the counter electrode 108 is formed by, for example, a sputtering method in a vacuum. Subsequently, on the counter electrode 108, the buffer layer 109 and the sealing layer 110 are formed in this order by, for example, a vacuum heating vapor deposition method. Thereafter, the color filters 111, the partitions 112, and the light-shielding layer 113 are formed, and then the protective layer 114 is formed, whereby the imaging device 100 is completed.

In the method for producing the imaging device 100, it is also possible to prevent performance deterioration of the plural photoelectric conversion elements by adding a process of placing the imaging device 100 under manufacture into a non-vacuum environment between the process of forming the photoelectric conversion film 107 and the process of forming the sealing layer 110. By adding this process, it is possible to reduce the production cost while preventing performance deterioration of the imaging device 100.

EXAMPLES

Examples will be described below, but the present invention is not limited thereto.

Synthesis Example 1: Synthesis of Compound 1

A compound 1 was synthesized according to the following scheme (1). By performing $^1$H NMR spectrum analysis on the obtained compound 1, the compound was identified. $^1$H NMR (400 MHz, CDCl$_3$): δ=3.89 (s, 3H), 6.90 (s, 2H), 7.05 (d, 2H), 7.80 (d, 2H)

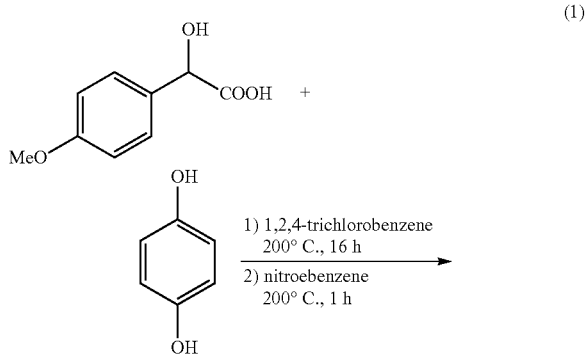

-continued

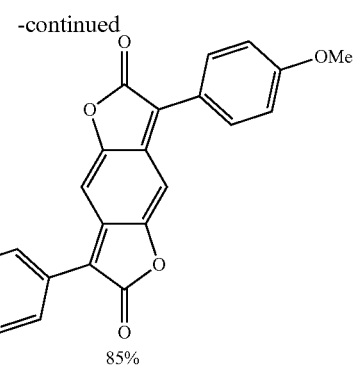

85%

A compound 2, a compound 5, and a compound 12 were also synthesized under the same synthesis conditions as the synthesis conditions used for synthesizing the compound 1.

Synthesis Example 2: Synthesis of Compound 3

A compound 3 was synthesized according to the following scheme (2).

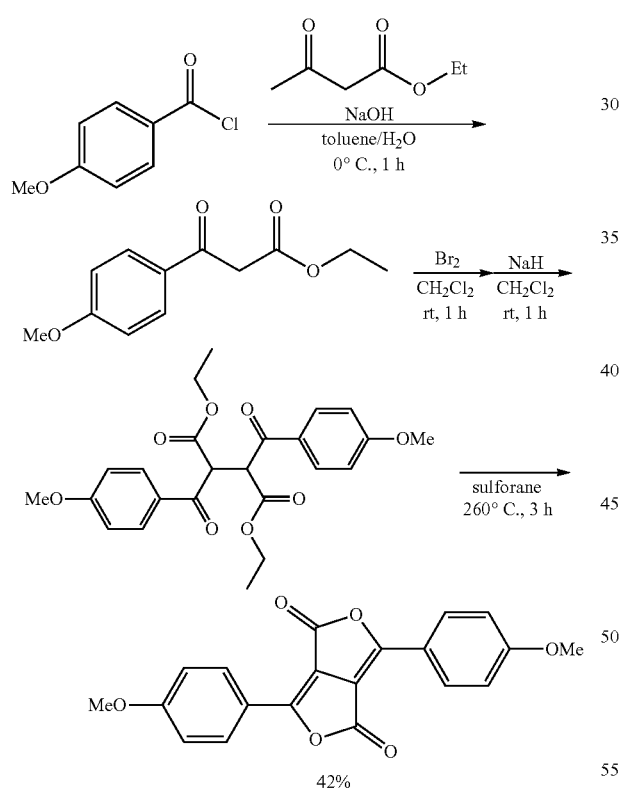

42%

Synthesis Example 3: Synthesis of Compound 4

Under the same synthesis conditions as the synthesis conditions used in the method described in Macromolecules 2011, 44, 4596-4599, a compound 4 was synthesized.

A compound 6 and a compound 7 were also synthesized by using the corresponding starting materials, under the same synthesis conditions as described above.

Synthesis Example 4: Synthesis of Compound 10

A compound 10 was synthesized according to the following scheme (3).

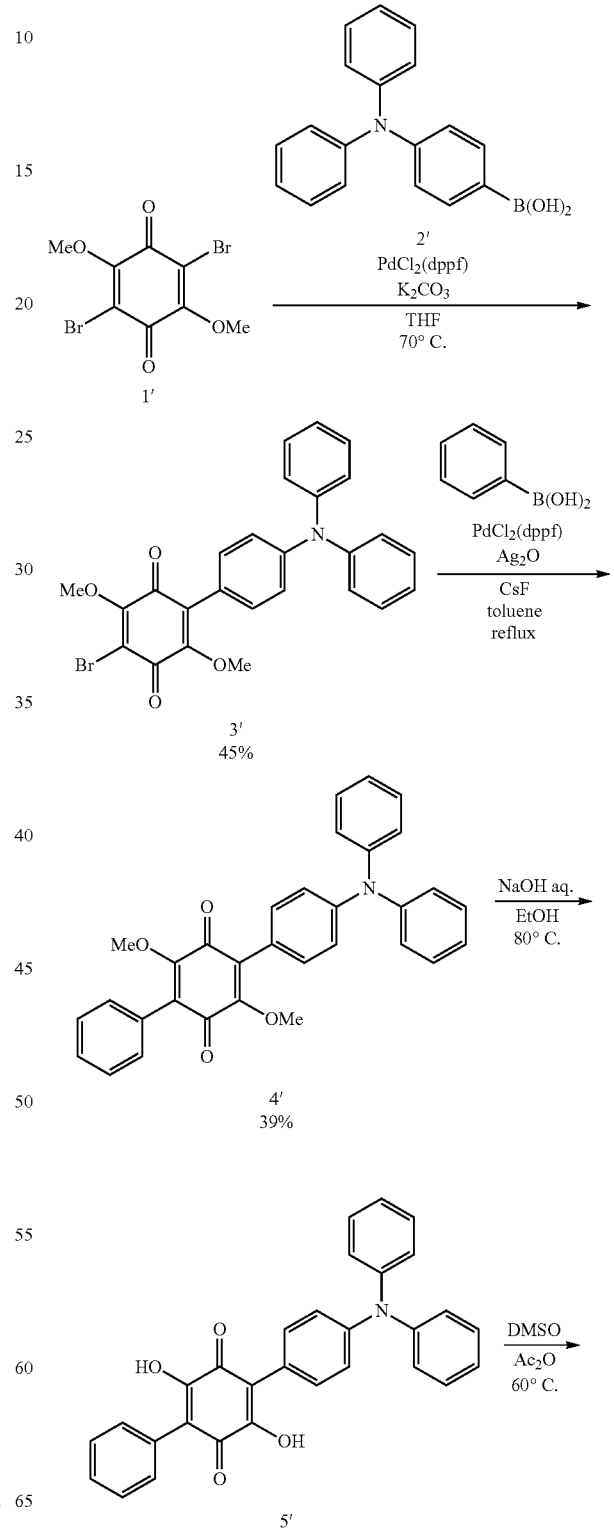

(3)

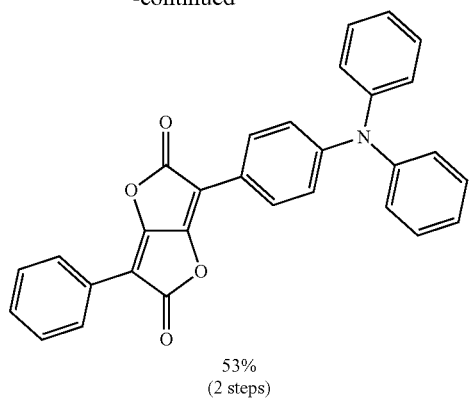

53%
(2 steps)

A compound 1' (3.26 g, 10.0 mmol), a compound 2' (2.89 g, 10.0 mmol), [dichloro(diphenylphosphinoferrocene)palladium]dichloromethane complex (408 mg, 0.500 mmol), and potassium carbonate (4.15 g, 30.0 mmol) were added to THF (100 mL), and the resultant was reacted for a day under reflux under a nitrogen gas stream. After being returned to room temperature, the resultant was filtered to remove insoluble matter and then concentrated. Thereafter, the resultant was purified by using a silica gel column (developing solvent: 10% ethyl acetate/hexane), thereby obtaining a compound 3' (2.19 g, yield: 45%).

The compound 3' (2.19 g, 4.47 mmol), phenylboronic acid (1.64 g, 13.4 mmol), [dichloro(diphenylphosphinoferrocene) palladium]dichloromethane complex (182 mg, 0.223 mmol), cesium fluoride (3.40 g, 22.4 mmol), and silver(I) oxide (2.59 g, 11.2 mmol) were added to toluene (22 mL), and the resultant was reacted for 19 hours under reflux under a nitrogen gas stream. After being returned to room temperature, the resultant was filtered to remove insoluble matter and then concentrated. Thereafter, the resultant was purified by gel permeation chromatography (developing solvent: tetrahydrofuran), and the obtained solid was recrystallized from acetonitrile, thereby obtaining a compound 4' (860 mg, yield: 39%).

The compound 4' (860 mg, 1.76 mmol) was dispersed in a liquid mixture of an aqueous solution of 1 M sodium hydroxide (86 mL) and ethanol (86 mL), and the resultant was reacted for 1.5 hours at 70° C. After the resultant was returned to room temperature, 1 M hydrochloric acid (200 mL) was added thereto, and extraction was performed on the resultant by using ethyl acetate. After an oil layer was washed with saturated saline, the resultant was dried over magnesium sulfate, filtered, and concentrated, thereby obtaining a compound 5'. The compound 5' was dissolved in acetic anhydride (10 mL) and dimethylsulfoxide (20 mL), and the resultant was reacted for 3 hours at 80° C. After the resultant was returned to room temperature, the precipitate was filtered, and the obtained solid was recrystallized from acetonitrile, thereby obtaining the compound 10 (430 mg, yield: 53%).

By performing $^1$H NMR spectrum analysis on the obtained compound 10, the compound was identified. $^1$H-NMR (400 MHz, CDCl$_3$): δ=7.06-7.17 (m, 8H), 7.32 (t, 4H), 7.42 (t, 1H), 7.49 (t, 2H), 7.87 (d, 2H), 8.03 (d, 2H)

Synthesis Example 5: Synthesis of Compound 8

By using a compound 11', which will be described later, instead of the compound 2' in the scheme (3), a compound 8 was synthesized under the same synthesis conditions. By performing MS spectrum analysis on the obtained compound, the compound was identified. MS (ESI$^+$) m/z: 508.2 ([M+H]$^+$)

Synthesis Example 6: Synthesis of Compound 9

By using a compound 17', which will be described later, instead of the compound 2' in the scheme (3), a compound 9 was synthesized under the same synthesis conditions. By performing MS spectrum analysis on the obtained compound, the compound was identified. MS (ESI$^+$) m/z: 498.2 ([M+H]$^+$)

Synthesis Example 7: Synthesis of Compound 11

By using p-fluorophenylboronic acid instead of phenylboronic acid in the scheme (3), a compound 11 was synthesized under the same synthesis conditions. By performing MS spectrum analysis on the obtained compound, the compound was identified. MS (ESI$^+$) m/z: 476.1 ([M+H]$^+$)

Synthesis Example 8: Synthesis of Compound 13

A compound 13 was synthesized according to the following scheme (4).

(4)

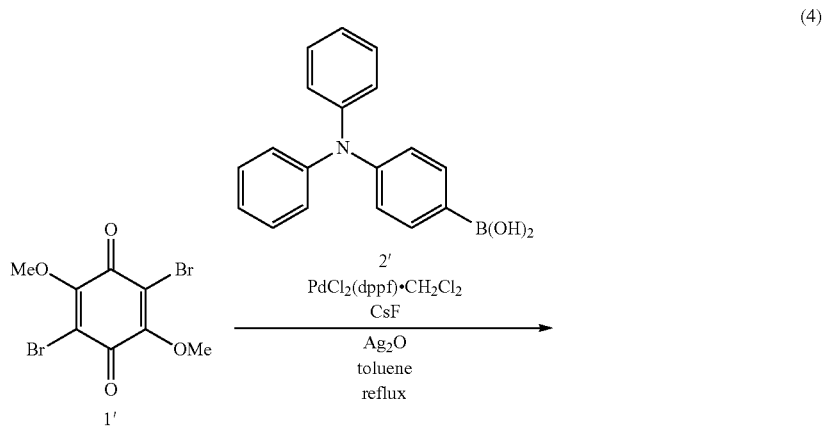

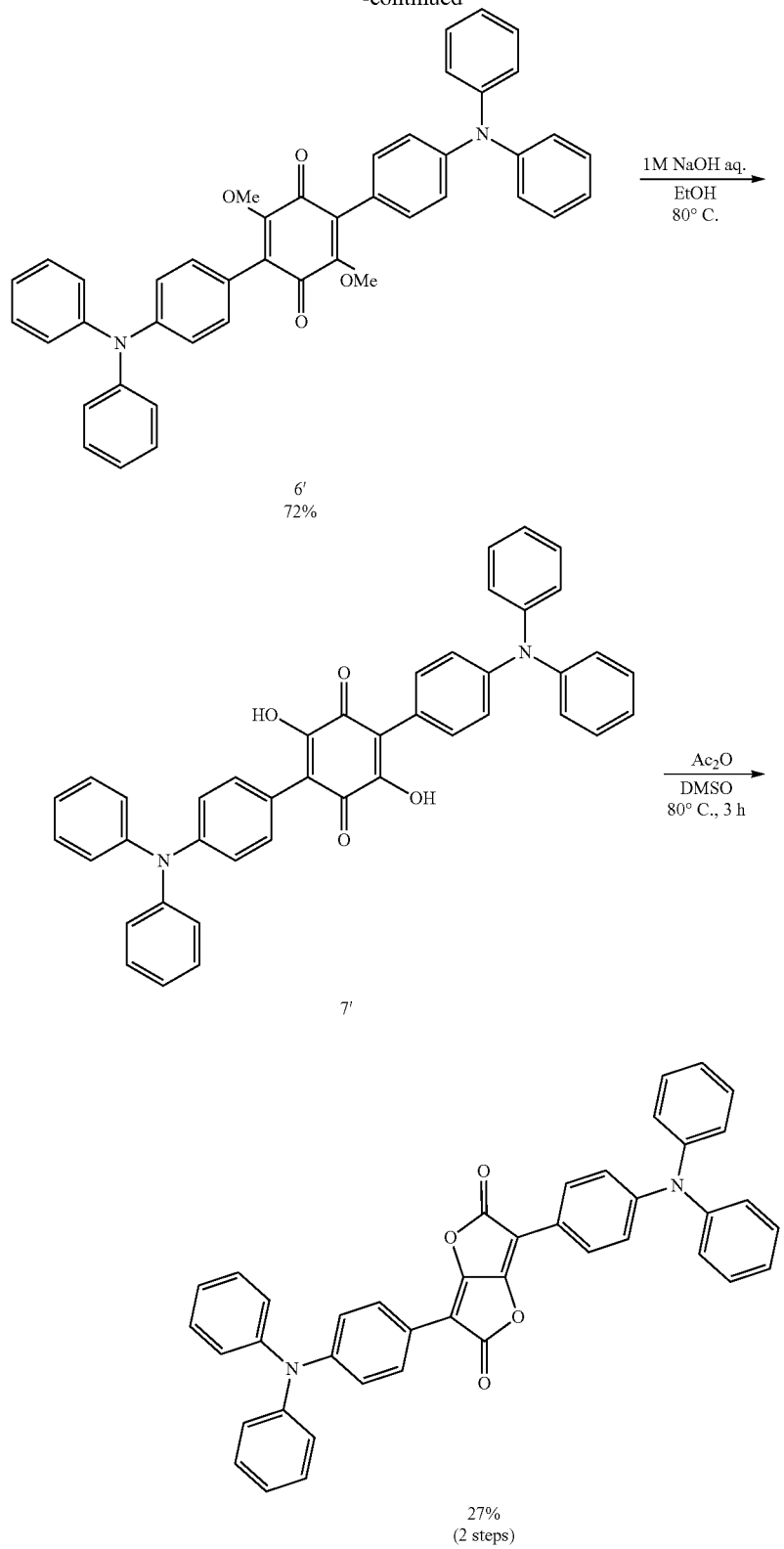

Toluene (50 mL) was added to a mixture of the compound 1' (1.63 g, 5.00 mmol), the compound 2' (3.61 g, 12.5 mmol), a [dichloro(diphenylphosphinoferrocene)palladium]dichloromethane complex (82 mg, 0.10 mmol), cesium fluoride (3.80 g, 25.0 mmol), and silver(I) oxide (2.90 g, 12.5 mmol), and the resultant was reacted for two days under reflux under a nitrogen gas stream. After being returned to room temperature, the resultant was filtered to remove insoluble matter and concentrated. Thereafter, the resultant was recrystallized from toluene, thereby obtaining a compound 6' (2.35 g, yield: 72%).

The compound 6' (2.00 g, 3.05 mmol) was dispersed in a liquid mixture of an aqueous solution of 1 M sodium hydroxide (100 mL) and ethanol (200 mL), and the resultant was reacted for 3 hours at 80° C. After the resultant was returned to room temperature, 1 M hydrochloric acid (200 mL) was added thereto, and extraction was performed on the resultant by using ethyl acetate. After an oil layer was washed with saturated saline, the resultant was dried over magnesium sulfate, filtered, and concentrated, thereby obtaining a compound 7'. The compound 7' was dissolved in acetic anhydride (60 mL) and dimethylsulfoxide (120 mL), and the resultant was reacted for 3 hours at 80° C. After the resultant was returned to room temperature, the precipitate was filtered, and the obtained solid was purified by using a silica gel column (developing solvent: chloroform). Subsequently, the resultant was recrystallized from acetonitrile, thereby obtaining the compound 13 (530 mg, yield: 27%).

By performing $^1$H NMR spectrum analysis on the obtained compound 13, the compound was identified. $^1$H NMR (400 MHz, CDCl$_3$): δ=7.07-7.16 (m, 16H), 7.28-7.34 (m, 8H), 7.86 (d, 4H)

Synthesis Example 9: Synthesis of Compound 15

By using the compound 11' instead of the compound 2' in the scheme (4), a compound 15 was synthesized under the same synthesis conditions. By performing $^1$H NMR spectrum analysis on the obtained compound 15, the compound was identified. $^1$H NMR (400 MHz, CDCl$_3$): δ=7.10 (t, 4H), 7.18 (d, 8H), 7.29-7.34 (m, 12H), 7.63 (d, 2H), 7.79 (d, 2H), 7.94 (d, 2H), 8.55 (s, 2H)

The compound 11' was synthesized according to the following scheme (5).

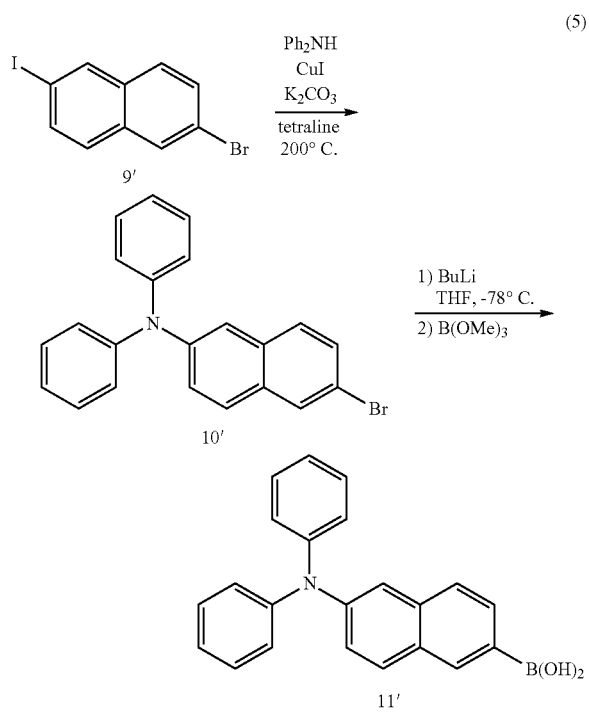

A mixture of 2-bromo-7-iodonaphthalene (12.0 g, 36.0 mmol), diphenylamine (6.08 g, 35.9 mmol), copper iodide (688 mg, 3.61 mmol), potassium carbonate (10.0 g, 72.1 mmol), and tetralin (8.0 mL) was reacted for 21 hours at 200° C. After the resultant was returned to room temperature, toluene (50 mL) was added thereto, insoluble matter was filtered, and the resultant was concentrated. The obtained oily substance was purified by using a silica gel column (toluene/hexane), thereby obtaining a compound 10' (4.52 g, yield: 33%).

The compound 10' (3.93 g, 10.5 mmol) was dissolved in tetrahydrofuran (105 mL), the resultant was cooled to −78° C., and butyllithium (1.6 M hexane solution, 7.25 mL, 11.6 mmol) was added dropwise thereto over 15 minutes. The resultant was stirred for 15 minutes, and then trimethoxyborane (2.18 g, 21.0 mmol) was added dropwise thereto over 15 minutes. After being reacted for 30 minutes, the resultant was returned to room temperature, 1 M hydrochloric acid (150 mL) was added thereto, and extraction was performed on the resultant by using ethyl acetate. An oil layer was washed with saturated saline, and the resultant was dried over magnesium sulfate, filtered, and concentrated, thereby obtaining the compound 11' (2.43 g, yield: 68%).

Synthesis Example 10: Synthesis of Compound 18

By using 4-[N,N'-di(p-tolyl)amino]phenyl borate instead of 4-(N,N'-diphenylamino)phenyl borate (compound 2') in the scheme (4), a compound 18 was synthesized under the same synthesis conditions. By performing $^1$H NMR spectrum analysis on the obtained compound 18, the compound was identified. $^1$H NMR (400 MHz, CDCl$_3$): δ=2.34 (s, 12H), 7.00-7.05 (m, 12H), 7.11 (d, 8H), 7.82 (d, 4H)

Synthesis Example 11: Synthesis of Compound 22

By using the compound 17' instead of the compound 2' in the scheme (4), a compound 22 was synthesized under the same synthesis conditions. By performing $^1$H NMR spectrum analysis on the obtained compound 22, the compound was identified. $^1$H NMR (400 MHz, CDCl$_3$): δ=1.73 (s, 12H), 6.26-6.29 (m, 2H), 6.33 (d, 2H), 6.96-7.02 (m, 4H), 7.33 (d, 4H), 7.48-7.56 (m, 4H), 7.63-7.68 (m, 6H), 8.13 (s, 2H)

The compound 17' was synthesized according to the following scheme (6).

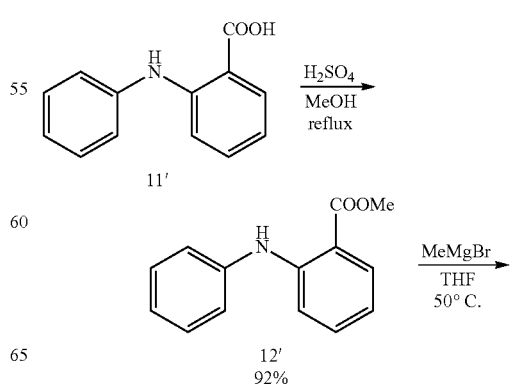

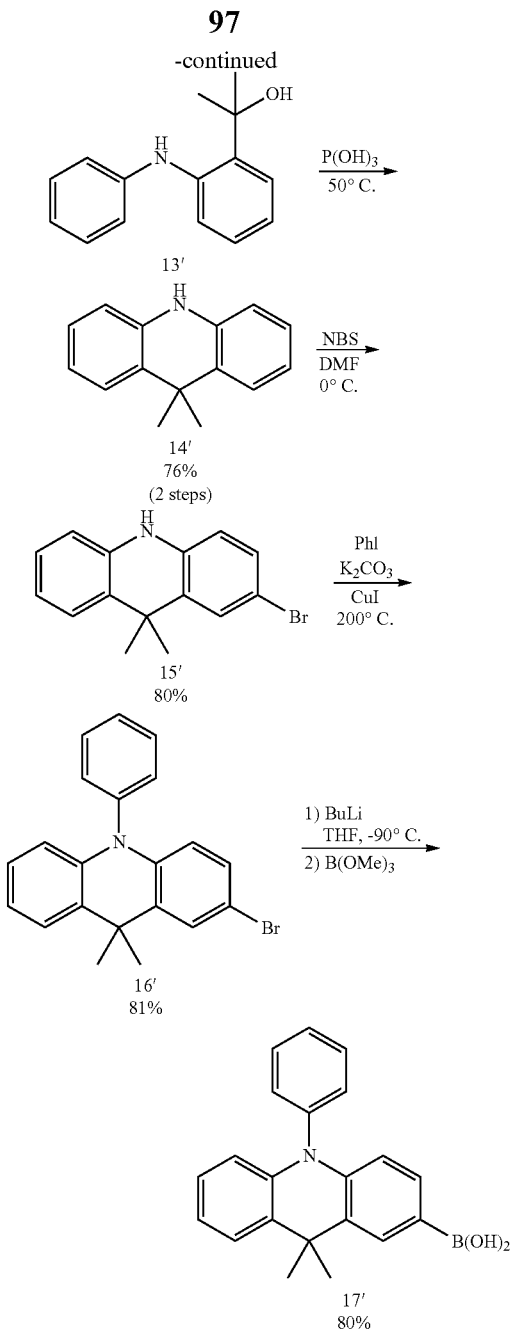

The compound 11' (100 g, 469 mmol) was added to methanol (1,000 mL), and sulfuric acid (100 mL) was added dropwise thereto at room temperature. After the resultant was reacted for a day under reflux, methanol was distilled away, and extraction was performed on the resultant by adding water (1,000 mL) and ethyl acetate (1,000 mL) thereto. After the resultant was washed with saturated aqueous sodium bicarbonate solution, water, and saturated saline, an oil layer was dried over sodium sulfate, and the resultant was filtered and concentrated. Subsequently, the resultant was recrystallized from methanol, thereby obtaining a compound 12' (97.8 g, yield: 92%).

The compound 12' (95.0 g, 418 mmol) was dissolved in tetrahydrofuran (THF) (1,500 mL), and methylmagnesium bromide (3 M ether solution, 488 mL, 1.46 mol) was added dropwise thereto at room temperature. After the resultant was reacted for an hour at 50° C., water (500 mL) and 1 M hydrochloric acid (1,000 mL) were added thereto, and extraction was performed on the resultant by using ethyl acetate. An oil layer was washed with water and saturated saline, and then the resultant was dried over sodium sulfate, filtered, and concentrated, thereby obtaining a compound 13'. The obtained compound 13' was dissolved in phosphoric acid (950 mL), and the resultant was reacted for 2.5 hours at 50° C. After the resultant was returned to room temperature, water (1,000 mL) was added thereto, and the resultant was recrystallized from ethanol/hexane, thereby obtaining a compound 14' (66.4 g, yield: 76%).

The compound 14' (12.0 g, 57.3 mmol) was dissolved in dimethylformamide (DMF) (400 mL), and the resultant was cooled to 0° C. To the resultant, a solution, which was obtained by dissolving N-bromosuccinimide (10.2 g, 57.4 mmol) in DMF (100 mL), was added. After being reacted for 30 minutes, the resultant was returned to room temperature, and extraction was performed on the resultant by adding water and ethyl acetate thereto. An oil layer was washed with water and saturated saline, and then the resultant was dried over sodium sulfate, filtered, and concentrated. The obtained oily substance was purified by using a silica gel column (50% ethyl acetate/hexane), thereby obtaining a compound 15' (14.4 g, yield: 80%).

A mixture of the compound 15' (3.40 g, 11.8 mmol), iodobenzene (24.1 g, 118 mmol), potassium carbonate (3.26 g, 23.6 mmol), and copper iodide (112 mg, 0.59 mmol) was reacted for 6 hours at 200° C. After the resultant was returned to room temperature, toluene (250 mL) was added thereto, insoluble matter was filtered, and the resultant was concentrated. The obtained oily substance was purified by using a silica gel column, thereby obtaining a compound 16' (3.49 g, yield: 81%).

The compound 16' (6.00 g, 16.5 mmol) was dissolved in THF (165 mL), the resultant was cooled to −90° C., and then butyllithium (1.6 M hexane solution, 10.3 mL, 16.5 mmol) was added dropwise thereto. After the resultant was stirred for 30 minutes, trimethoxyborane (3.42 g, 32.9 mmol) was added dropwise thereto. After being reacted for 2 hours, the resultant was heated to 0° C., 1 M hydrochloric acid (300 mL) was added thereto, and the resultant was stirred for 30 minutes. Extraction was performed on the resultant by using ethyl acetate, an oil layer was washed with water and saturated saline, and then the resultant was dried over sodium sulfate, filtered, and concentrated. The obtained solid was recrystallized from octane, thereby obtaining the compound 17' (5.35 g, yield: 80%).

Synthesis Example 12: Synthesis of Compound 23

By using a compound 18' instead of the compound 2' in the scheme (4), a compound 23 was synthesized under the same synthesis conditions. By performing $^1$H NMR spectrum analysis on the obtained compound 23, the compound was identified. $^1$H NMR (400 MHz, CDCl$_3$): δ=1.71 (s, 12H), 3.93 (s, 6H), 6.33 (d, 2H), 6.37 (d, 2H), 6.95-7.02 (m, 4H), 7.13-7.17 (m, 4H), 7.21-7.29 (m, 4H), 7.48 (d, 2H), 7.67 (d, 2H), 8.13 (s, 2H)

The compound 18' was synthesized by using p-methoxy-iodobenzene instead of iodobenzene in the scheme (6).

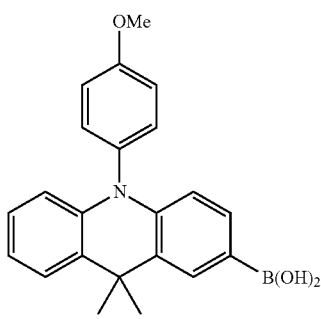

18'

Synthesis Example 13: Synthesis of Compound 24

By using a compound 20' instead of the compound 2' in the scheme (4), a compound 24 was synthesized under the same synthesis conditions. By performing $^1$H NMR spectrum analysis on the obtained compound 24, the compound was identified. $^1$H NMR (400 MHz, CDCl$_3$): δ=1.60 (s, 12H), 3.69 (s, 6H), 6.99-7.08 (m, 6H), 7.21-7.28 (m, 2H), 7.46 (d, 2H), 7.97 (d, 2H), 8.09 (s, 2H)

The compound 20' was synthesized according to the following scheme (7).

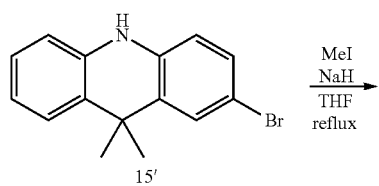

(7)

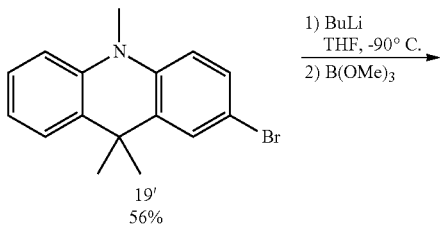

19'
56%

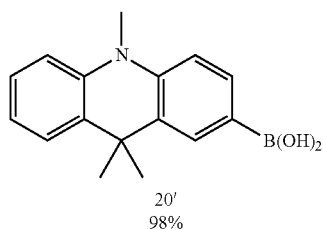

20'
98%

Synthesis Example 14: Synthesis of Compound 16

A compound 16 was synthesized according to the following scheme (8). A compound 21' was synthesized under the same conditions as the synthesis conditions for synthesizing the compound 3.

(8)

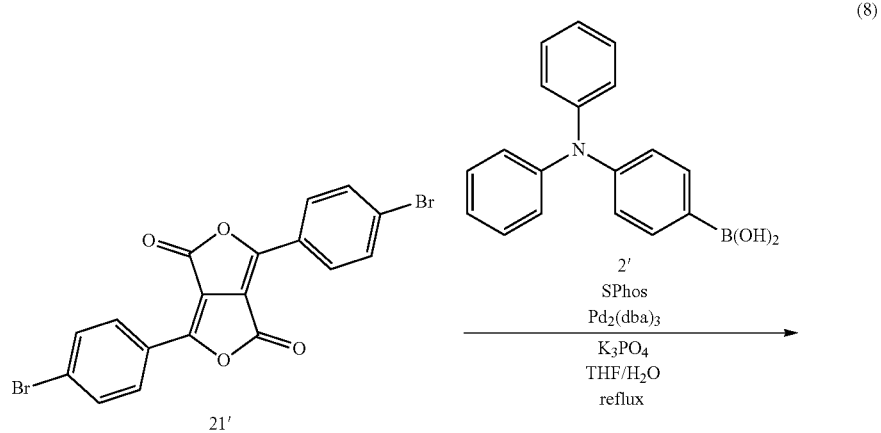

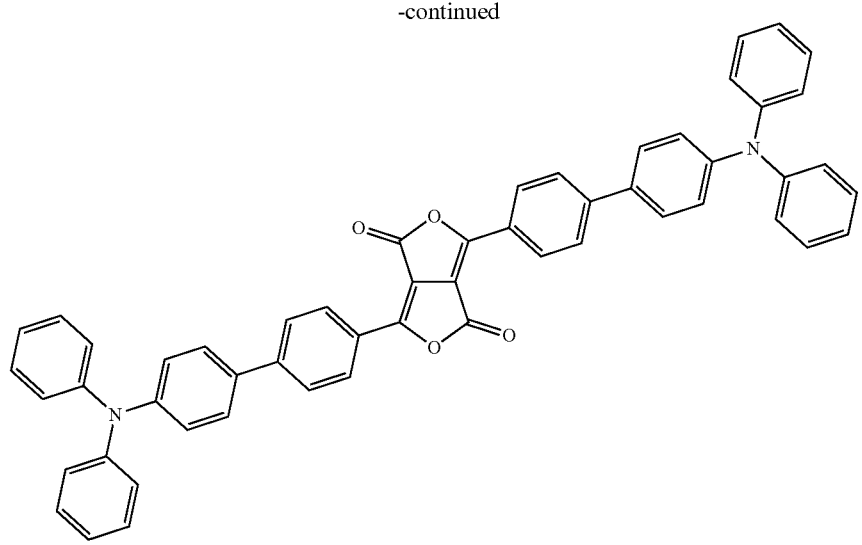

The compound 21' (0.72 g, 1.61 mmol), the compound 2' (1.70 g, 5.88 mmol), SPhos (130 mg, 0.32 mmol), Pd$_2$(dba)$_3$ (140 mg, 0.16 mmol), and tripotassium phosphate (770 mg, 3.63 mmol) were added to a mixture of toluene (30 mL) and water (7.5 mL), and the resultant was reacted for 4 hours under reflux under a nitrogen gas stream. After the resultant was returned to room temperature, water was added thereto, and extraction was performed on the resultant by using toluene. An oil layer was washed with water and saturated saline, and then the resultant was dried over magnesium sulfate, filtered, and concentrated. The obtained solid was purified by using a silica gel column, thereby obtaining the compound 16 (0.51 g, yield: 41%).

By performing $^1$H NMR spectrum analysis on the obtained compound 16, the compound was identified. $^1$H NMR (400 MHz, CDCl$_3$): δ=7.09 (t, 4H), 7.14-7.17 (m, 12H), 7.28-7.32 (t, 8H), 7.56 (d, 4H), 7.77 (d, 4H), 8.32 (d, 4H)

Synthesis Example 15: Synthesis of Compound 17

A compound 17 was synthesized according to the following scheme (9).

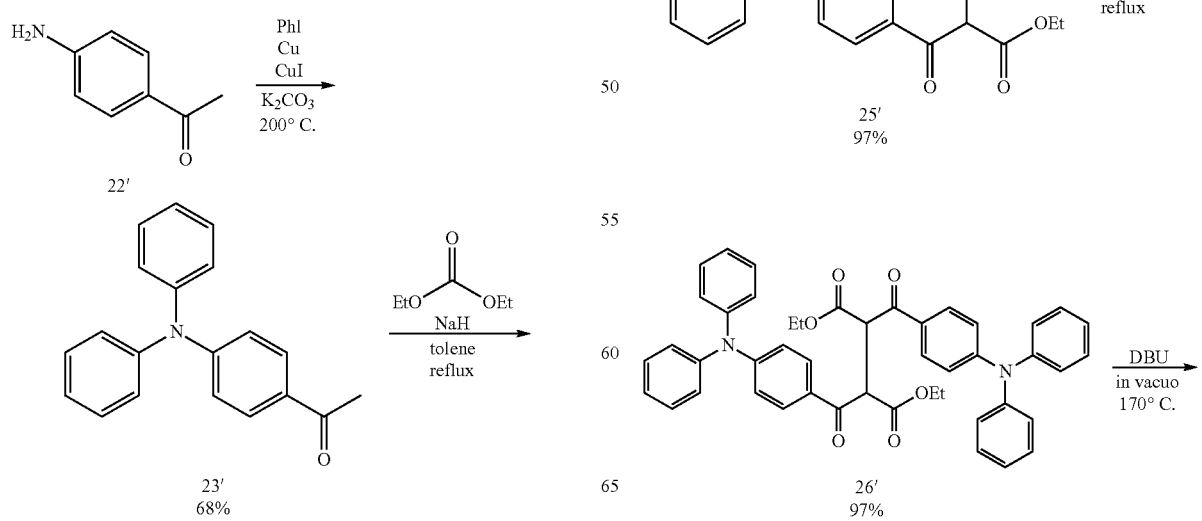

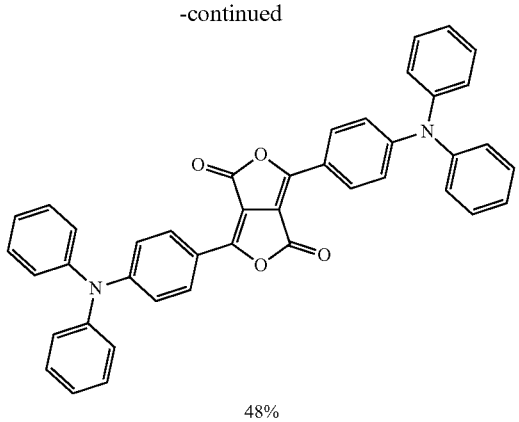

48%

A mixture of a compound 22' (25.0 g, 185 mmol), iodobenzene (151 g, 740 mmol), potassium carbonate (102.25 g, 740 mmol), copper powder (2.35 g, 37.0 mmol), and copper iodide (3.52 g, 18.5 mmol) was reacted for 7 hours at 200° C. After being returned to room temperature, the resultant was diluted with toluene and filtered, and the filtrate was concentrated. Subsequently, the resultant was purified by using a silica gel column (developing solvent: toluene), thereby obtaining a compound 23' (36.1 g, yield: 68%).

Sodium hydride (60 wt % dispersion in oil, 9.74 g, 244 mmol) and diethyl carbonate (35.9 g, 305 mmol) were added to toluene (200 mL), and the resultant was refluxed under a nitrogen gas stream. A solution, which was obtained by dissolving the compound 23' (35.0 g, 233 mmol) in toluene (24 mL), was added dropwise to the resultant over 15 minutes. After being refluxed for 2 hours, the resultant was returned to room temperature, 1 M hydrochloric acid (500 mL) was added thereto, and extraction was performed on the resultant by using ethyl acetate. An oil layer was washed with saturated saline, and then the resultant was dried over magnesium sulfate, filtered, and concentrated. The obtained oily substance was purified by using a silica gel column (toluene), thereby obtaining a compound 24' (38.2 g, yield: 91%).

The compound 24' (19.0 g, 55.3 mmol) and p-toluenesulfonic acid (0.42 g, 2.21 mmol) were added to toluene (380 mL), and the resultant was cooled to 0° C. Then, N-bromosuccinimide (9.95 g, 55.9 mmol) was added to the resultant. After being reacted for 1 hour, the resultant was returned to room temperature, water (500 mL) was added thereto, and extraction was performed on the resultant by using ethyl acetate. An oil layer was washed with water and saturated saline, and then the resultant was dried over magnesium sulfate, filtered, and concentrated. The obtained oily substance was purified by using a silica gel column (1% ethyl acetate/toluene), thereby obtaining a compound 25' (22.4 g, yield: 97%).

The compound 24' (17.89 g, 52.1 mmol) was dissolved in THF (180 mL), and sodium hydride (60 wt % dispersion in oil, 2.08 g, 52.1 mmol) was added thereto. The resultant was heated and stirred for 30 minutes at 40° C., and then a solution, which was obtained by dissolving the compound 25' (22.0 g, 52.1 mmol) in THF (220 mL), was added dropwise thereto over 10 minutes. After being reacted for 1.5 hours at 40° C., the resultant was returned to room temperature, water (200 mL) and 1 M hydrochloric acid (200 mL) were added thereto, and extraction was performed on the resultant by using ethyl acetate. An oil layer was washed with water and saturated saline, and then the resultant was dried over magnesium sulfate, filtered, and concentrated 26' (36.1 g, yield: 97%).

DBU (5 drops) was added to the compound 26' (10.0 g, 14.0 mmol), and the resultant was heated to 170° C. in a vacuum and reacted for 8 hours. After being left to cool, the resultant was dissolved in methylene chloride (300 mL), passed through a silica gel column, and repeatedly recrystallized from acetonitrile, thereby obtaining the compound 17 (4.20 g, yield: 48%).

By performing $^1$H NMR spectrum analysis on the obtained compound 17, the compound was identified. $^1$H NMR (400 MHz, CDCl$_3$): δ=7.04 (d, 4H), 7.17-7.21 (m, 12H), 7.36 (t, 8H), 8.05 (d, 4H)

Synthesis Example 16: Synthesis of Compound 14

By using a compound 27' instead of the compound 23' in the scheme (9), a compound 14 was synthesized under the same synthesis conditions. By performing $^1$H NMR spectrum analysis on the obtained compound 14, the compound was identified. $^1$H NMR (400 MHz, CDCl$_3$): δ=1.78 (s, 12H), 6.30 (d, 2H), 6.36 (d, 2H), 6.98-7.04 (m, 4H), 7.33 (d, 4H), 7.50-7.59 (m, 4H), 7.67 (t, 4H), 7.88 (d, 2H), 8.39 (s, 2H)

A compound 27' was synthesized according to the following scheme (10).

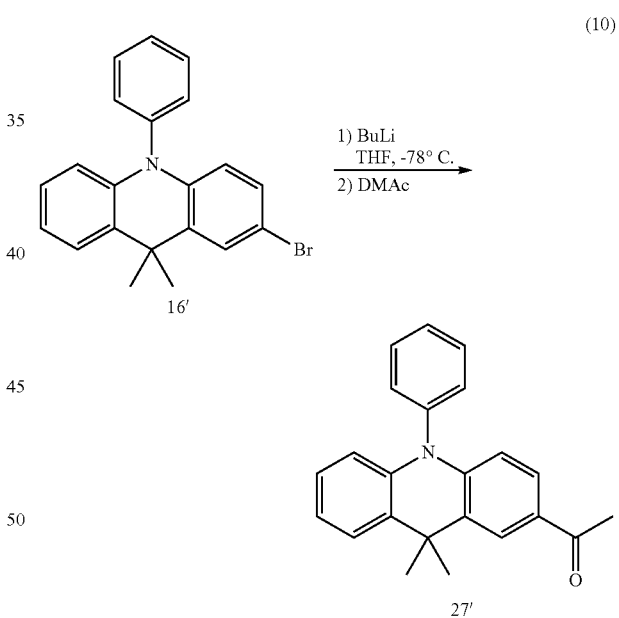

The compound 16' (27.5 g, 75.5 mmol) was dissolved in THF (755 mL), the resultant was cooled to −78° C., and butyllithium (1.6 M hexane solution, 51.9 mL, 83.0 mmol) was added dropwise thereto over 15 minutes. The resultant was stirred for 15 minutes, and then N,N'-dimethylacetamide (7.89 g, 90.6 mmol) was added dropwise thereto over 15 minutes. After being reacted for 30 minutes, the resultant was returned to room temperature, 1 M hydrochloric acid (1,500 mL) was added thereto, and extraction was performed on the resultant by using ethyl acetate. An oil layer was washed with saturated saline, and the resultant was dried over magnesium sulfate, filtered, and concentrated.

The obtained oily substance was recrystallized from methanol, thereby obtaining the compound 27' (21.7 g, yield: 59%).

Synthesis Example 17: Synthesis of Compound 19

By using a compound 28' instead of the compound 23' in the scheme (9), a compound 19 was synthesized under the same synthesis conditions. By performing ¹H NMR spectrum analysis on the obtained compound 19, the compound was identified. ¹H NMR (400 MHz, CDCl₃): δ=1.65 (s, 12H), 3.56 (s, 6H), 7.02-7.13 (m, 6H), 7.25-7.30 (m, 2H), 7.48 (d, 2H), 8.16 (d, 2H), 8.37 (s, 2H)

By using a compound 19' instead of the compound 16' in the scheme (10), the compound 28' was synthesized under the same conditions.

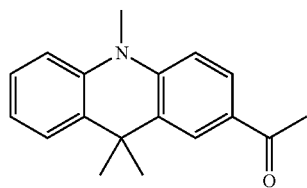

28'

Synthesis Example 18: Synthesis of Compound 20

By using a compound 31' instead of the compound 23' in the scheme (9), a compound 20 was synthesized under the same synthesis conditions. By performing ¹H NMR spectrum analysis on the obtained compound 20, the compound was identified. ¹H NMR (400 MHz, CDCl₃): δ=2.30 (s, 12H), 6.08 (d, 2H), 6.53 (d, 2H), 6.89-6.98 (m, 4H), 7.33 (d, 4H), 7.48-7.57 (m, 6H), 7.63 (t, 4H), 8.31 (t, 2H), 8.45 (s, 2H), 8.59 (d, 2H)

The compound 31' was synthesized according to the following scheme (11). A compound 29' was synthesized by the method described in JP 2012-77064 Å.

(11)

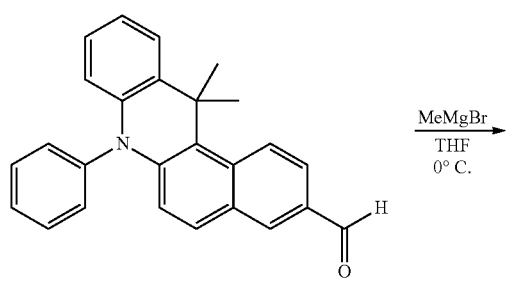

29'

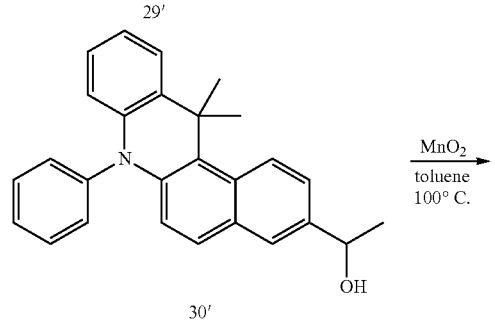

30'

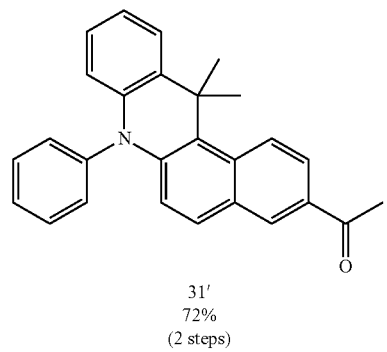

31'
72%
(2 steps)

The compound 29' (19.3 g, 53.0 mmol) was dissolved in THF (212 mL), the resultant was cooled to −78° C., and methylmagnesium bromide (3 M ether solution, 34 mL, 103 mmol) was added dropwise thereto. After the resultant was heated to 0° C. and reacted for 1 hour, 1 M hydrochloric acid (300 mL) was added thereto, and extraction was performed on the resultant by using ethyl acetate. An oil layer was washed with water and saturated saline, and then the resultant was dried over magnesium sulfate, filtered, and concentrated, thereby obtaining a compound 30'. The compound 30' was dissolved in toluene (265 mL), manganese(IV) oxide (15.2 g, 175 mmol) was added thereto, and the resultant was reacted for 5 hours at 100° C. After being returned to room temperature, the resultant was filtered so as to remove insoluble matter and concentrated. The obtained oily substance was purified by using silica gel column (toluene), thereby obtaining a compound 31' (14.4 g, yield: 72%).

Synthesis Example 19: Synthesis of Compound 21

By using the corresponding raw materials and using a compound 35' instead of the compound 23' in the scheme (9), a compound 21 was synthesized under the same synthesis conditions. By performing MS spectrum analysis on the obtained compound 21, the compound was identified. MS (ESI⁺) m/z: 681.3 ([M+H]⁺)

The compound 35' was synthesized according to the following scheme (12). A compound 32' was synthesized by the method described in JP 2012-77064 Å.

(12)

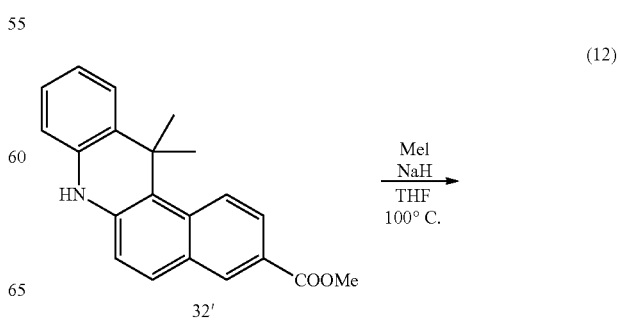

32'

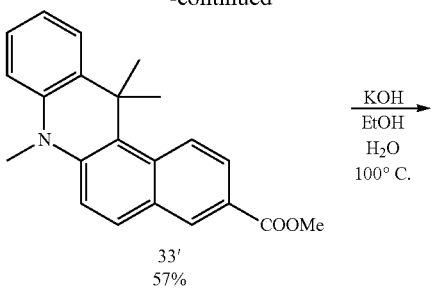

33'
57%

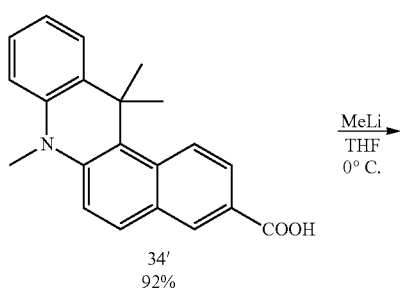

34'
92%

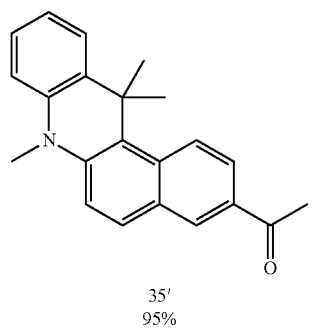

35'
95%

The compound 32' (20.0 g, 63.0 mmol) was dissolved in THF (315 mL), and sodium hydride (60 wt % dispersion in oil, 5.04 g, 126 mmol) was added thereto. After being refluxed for 2 hours, the resultant was returned to room temperature, and iodomethane (26.8 g, 189 mmol) was added thereto. After the resultant was reacted for 3 hours at room temperature, 1 M hydrochloric acid (500 mL) was added thereto, and extraction was performed on the resultant by using ethyl acetate. An oil layer was washed with water and saturated saline, and the resultant was dried over magnesium sulfate and then filtered and concentrated. The obtained solid was recrystallized from methanol, thereby obtaining a compound 33' (12.5 g, yield: 57%).

The compound 33' (12.5 g, 37.7 mmol) and potassium hydroxide (10.6 g, 188 mmol) were added to a mixture of ethanol (200 mL) and water (40 mL), and the resultant was reacted for 1 hour under reflux. After the resultant was returned to room temperature, 1 M hydrochloric acid (1,000 mL) was added thereto, and the precipitate was filtered. Then, the resultant was washed with water and methanol, thereby obtaining a compound 34' (11.0 g, yield: 92%).

The compound 34' (11.0 g, 34.7 mmol) was dissolved in THF (174 mL), the resultant was cooled to −78° C., and methyllithium (1.1 M ether solution, 77.0 mL, 86.8 mmol) was added dropwise thereto. After the resultant was heated to 0° C. and reacted for 30 minutes, 1 M hydrochloric acid (200 mL) was added thereto, and extraction was performed on the resultant by using ethyl acetate. An oil layer was washed with water and saturated saline, and then the resultant was dried over magnesium sulfate, filtered, and concentrated. The obtained solid was recrystallized from methanol, thereby obtaining the compound 35' (10.4 g, yield: 95%).

Synthesis Example 20: Synthesis of Compound 25

A compound 25 was synthesized under the same synthesis conditions as the synthesis conditions for synthesizing the compound 14, except that 3-bromo-9-phenylcarbazole was used instead of the compound 16'. By performing MS spectrum analysis on the obtained compound 25, the compound was identified. MS (ESI$^+$) m/z: 621.2 ([M+H]$^+$)

Synthesis Example 21: Synthesis of Compound 26

A compound 26 was synthesized under the same synthesis conditions as the synthesis conditions for synthesizing the compound 17, except that 4-(methylphenylamino)acetophenone was used instead of the compound 23'. By performing MS spectrum analysis on the obtained compound 26, the compound was identified. MS (ESI$^+$) m/z: 501.2 ([M+H]$^+$)

Synthesis Example 22: Synthesis of Compound 27

A compound 27 was synthesized under the same synthesis conditions as the synthesis conditions for synthesizing the compound 14, except that 3-bromopyridine was used instead of iodobenzene. By performing MS spectrum analysis on the obtained compound 27, the compound was identified. MS (ESI$^+$) m/z: 707.3 ([M+H]$^+$)

Synthesis Example 23: Synthesis of Compound 28

By using a compound 37' instead of the compound 23' in the scheme (9), a compound 28 was synthesized under the same synthesis conditions. By performing MS spectrum analysis on the obtained compound 28, the compound was identified. MS (ESI$^+$) m/z: 707.3 ([M+H]$^+$)

By using a compound 36', the compound 37' was synthesized according to the following scheme (13) under the same conditions as the conditions in the scheme (10).

(13)

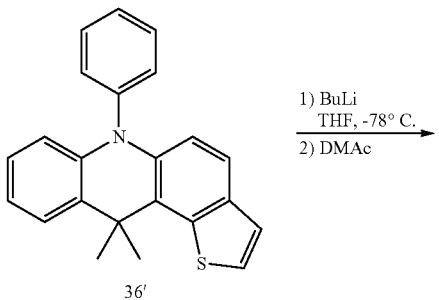

36'

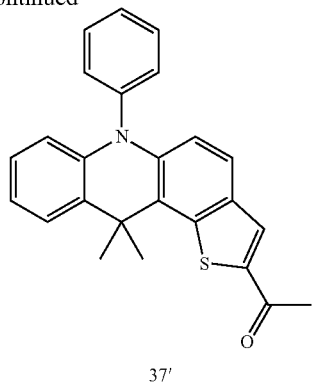

37'

Synthesis Example 24: Synthesis of Compound 29

By using p-dimethylaminoacetophenone instead of the compound 23' in the scheme (9), a compound 29 was synthesized under the same synthesis conditions. By performing MS spectrum analysis on the obtained compound, the compound was identified. MS (ESI$^+$) m/z: 377.2 ([M+H]$^+$)

Synthesis Example 25: Synthesis of Compound 30

A compound 30 was synthesized under the same synthesis conditions as the synthesis conditions for synthesizing the compound 17, except that N-(t-butyl)dithieno[3,2-b;2,3-d]pyrrole was used instead of the compound 36' in the scheme (13). By performing MS spectrum analysis on the obtained compound 30, the compound was identified. MS (ESI$^+$) m/z: 604.2 ([M+H]$^+$)

All of the compounds 1 to 30 and comparative compounds 1 and 2 used in the present examples and comparative examples are shown below.

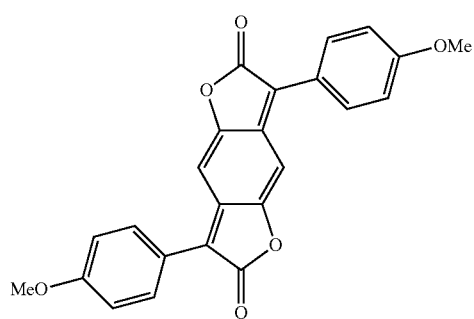

1

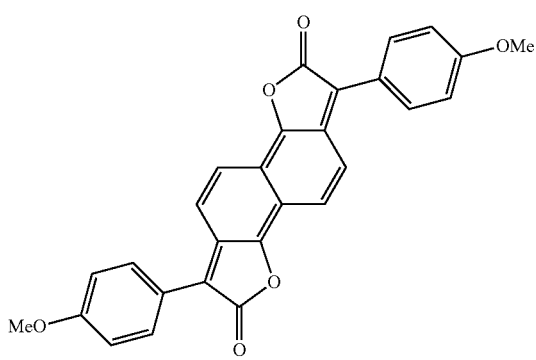

2

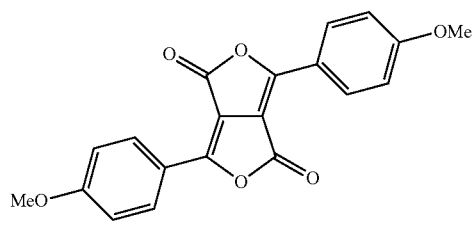

3

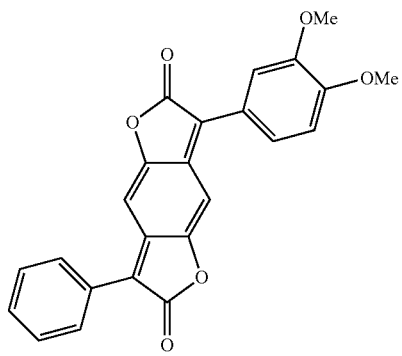

4

-continued
5
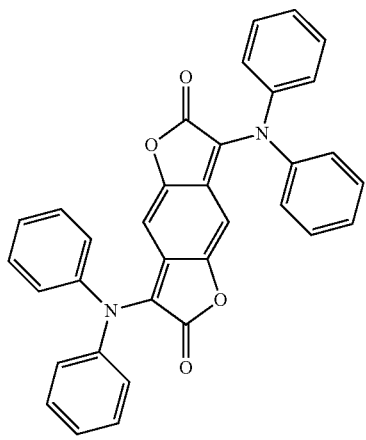
6
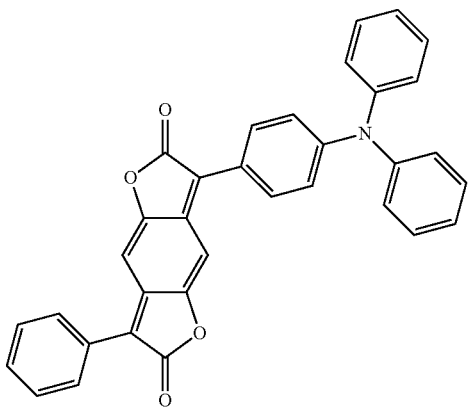
7
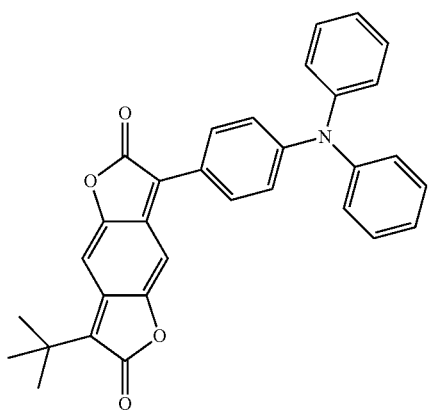
8
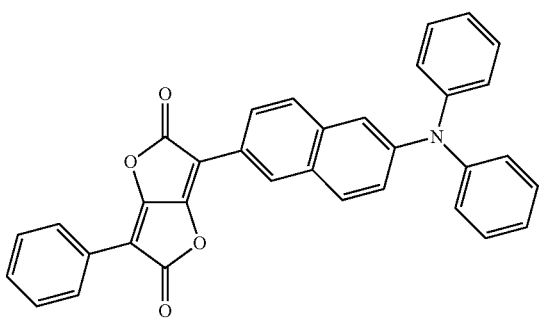
9
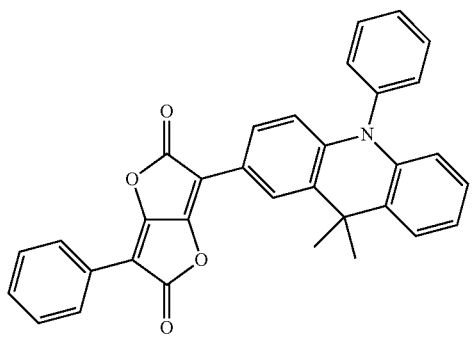
10
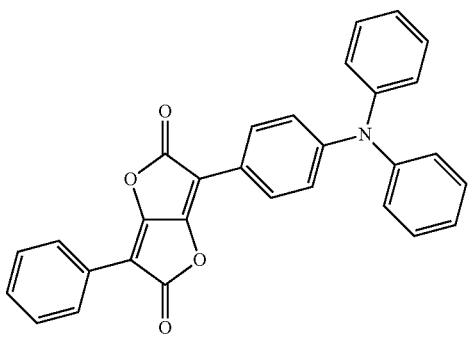
11
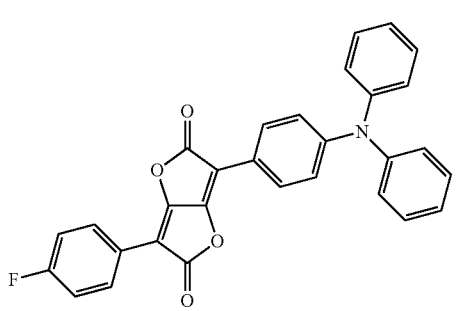
12
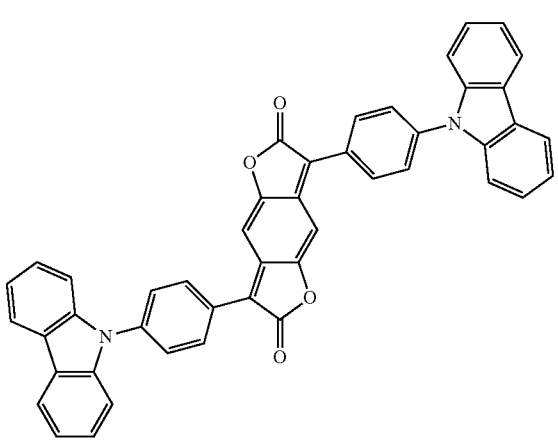

-continued
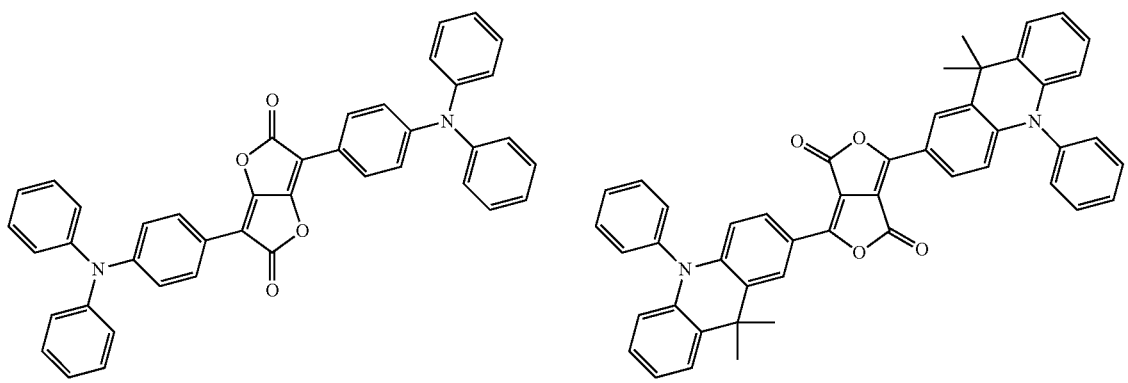
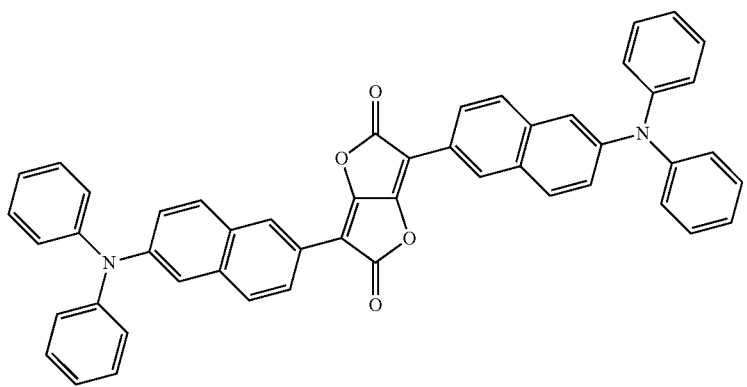
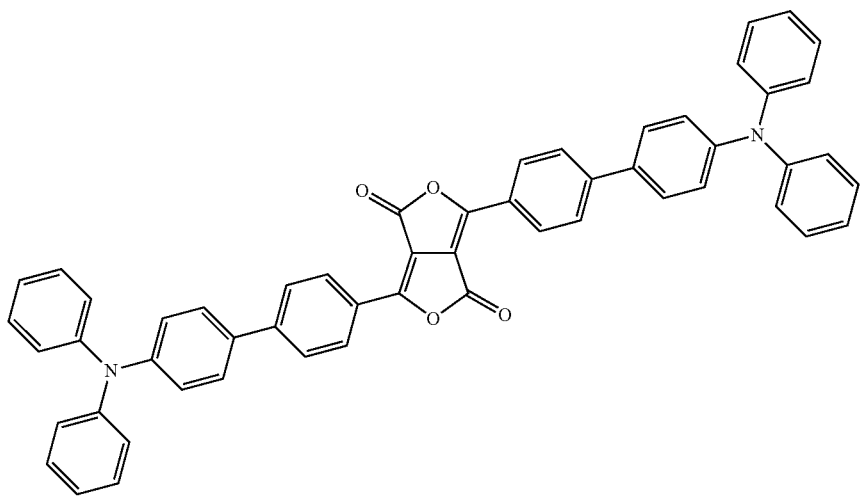

-continued
17
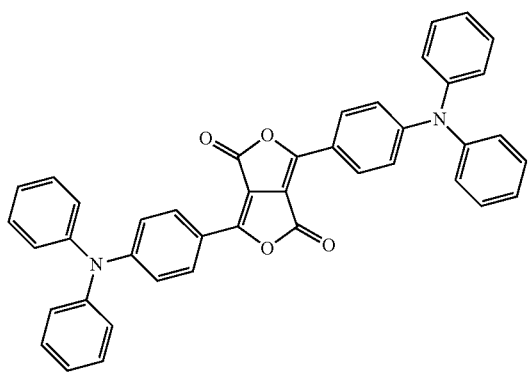
18
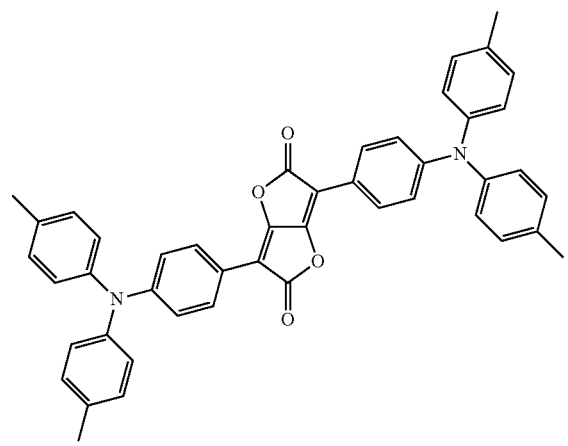
19
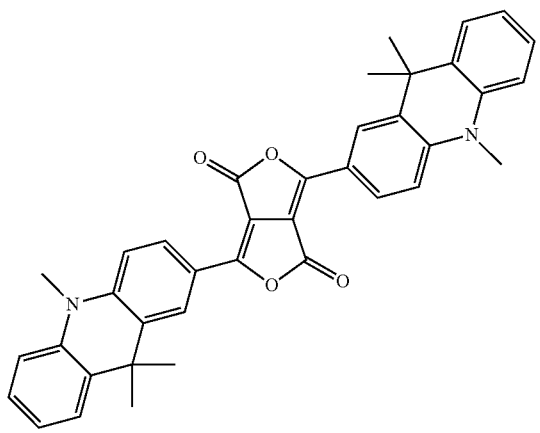
20
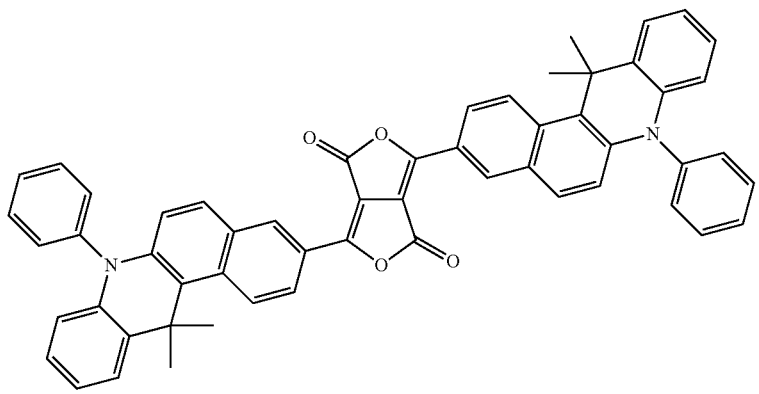
21
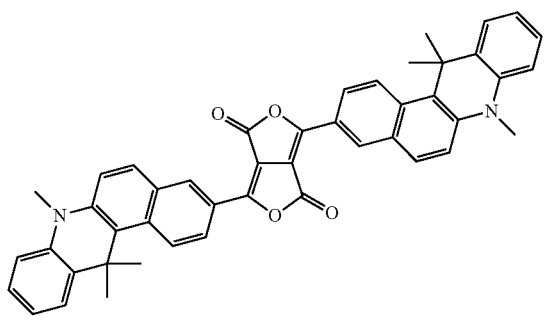
22
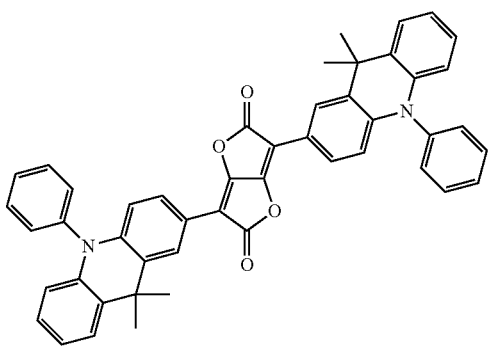

-continued
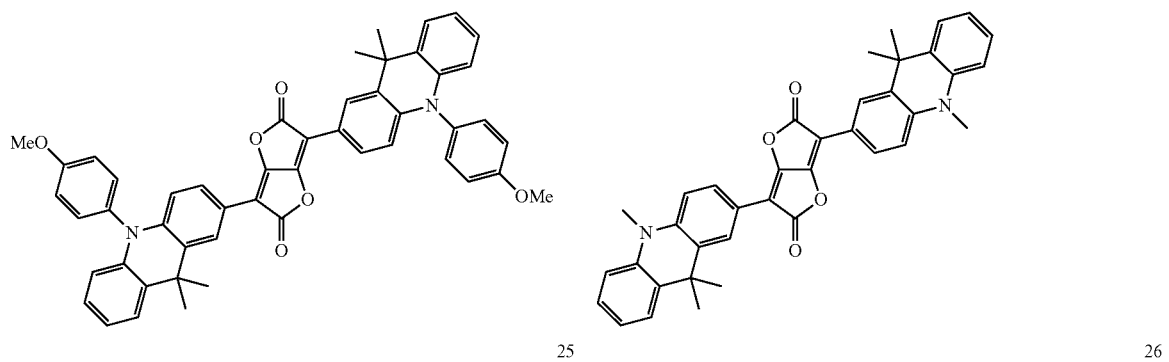
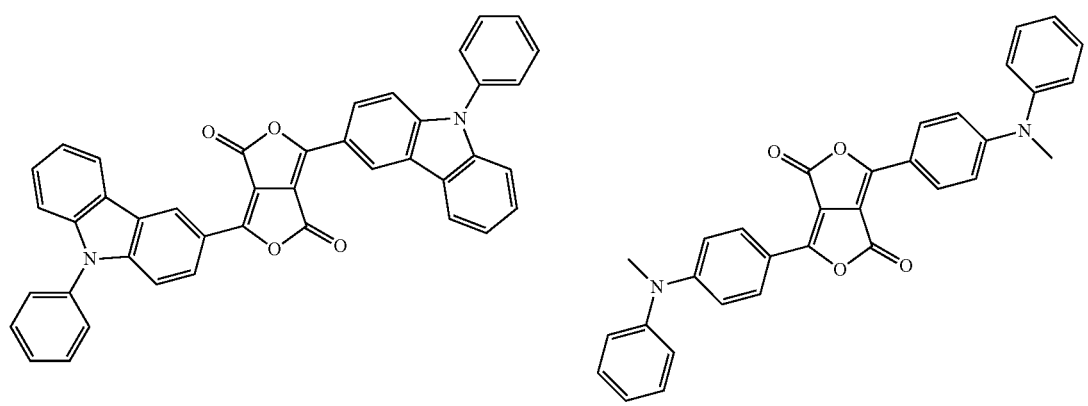
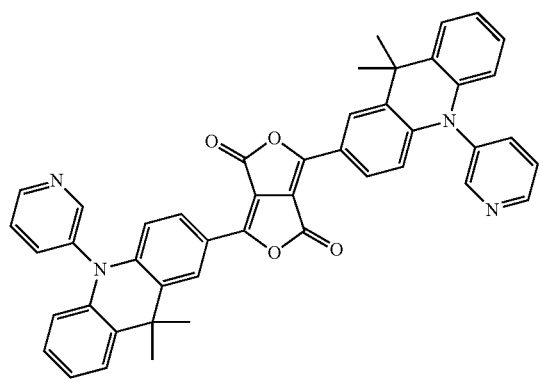
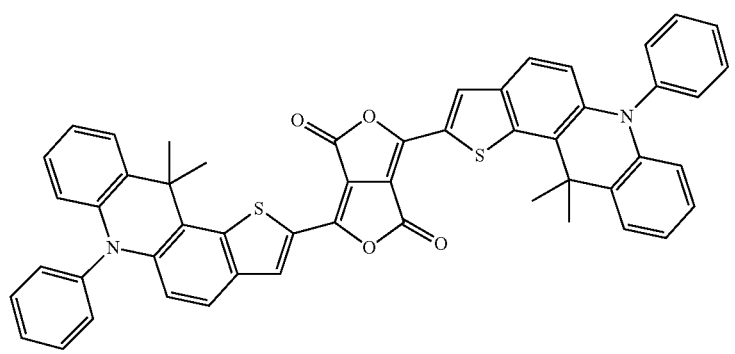

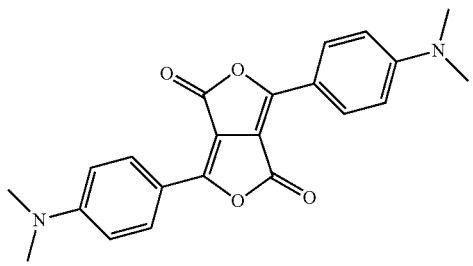

Comparative Compound 1

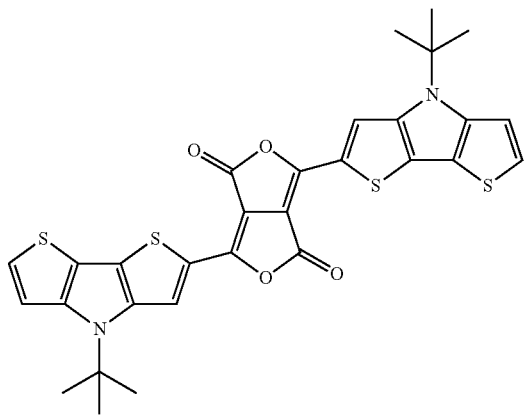

Comparative Compound 2

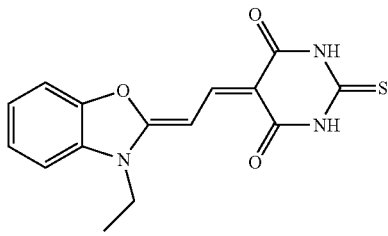

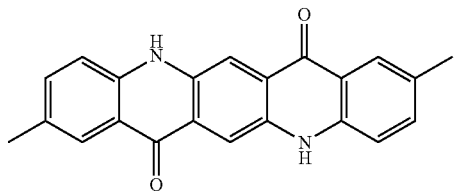

<Preparation of Photoelectric Conversion Element>

The photoelectric conversion element in the form shown in FIG. 1A was prepared. Herein, the photoelectric conversion element was constituted of the lower electrode 11, the electron blocking film 16A, the photoelectric conversion film 12, and the upper electrode 15.

Specifically, on a glass substrate, amorphous ITO was formed into a film by a sputtering method, thereby forming the lower electrode 11 (thickness: 30 nm). Thereafter, on the lower electrode 11, the following compound (EB-1) was formed into a film by a vacuum heating vapor deposition method, thereby forming the electron blocking film 16A (thickness: 100 nm). Moreover, in a state where the substrate temperature was being controlled to be 25° C., on the electron blocking film 16A, the compound (one of the compounds 1 to 30 and the comparative compounds 1 and 2) and fullerene $C_{60}$ were co-deposited and formed into a film by vacuum heating vapor deposition such that the thicknesses thereof became 120 nm and 280 nm, respectively, in terms of a single layer, thereby forming the photoelectric conversion film 12. The compound was formed into a film at a vapor deposition rate of 2.6 Å/sec. Furthermore, on the photoelectric conversion film 12, amorphous ITO was formed into a film by a sputtering method, thereby forming the upper electrode 15 (transparent conductive film) (thickness: 10 nm). On the upper electrode 15, a SiO film was formed as a sealing layer by heating vapor deposition, and on this film, an aluminum oxide ($Al_2O_3$) layer was formed by an ALCVD method, thereby preparing the photoelectric conversion element.

In the photoelectric conversion film 12, a content ratio of fullerene $C_{60}$ (a film thickness of the fullerene $C_{60}$ expressed in terms of a single layer/(a film thickness of the compound expressed in terms of a single layer+a film thickness of the fullerene $C_{60}$ expressed in terms of a single layer)) was 70% by volume.

Compound (EB-1)

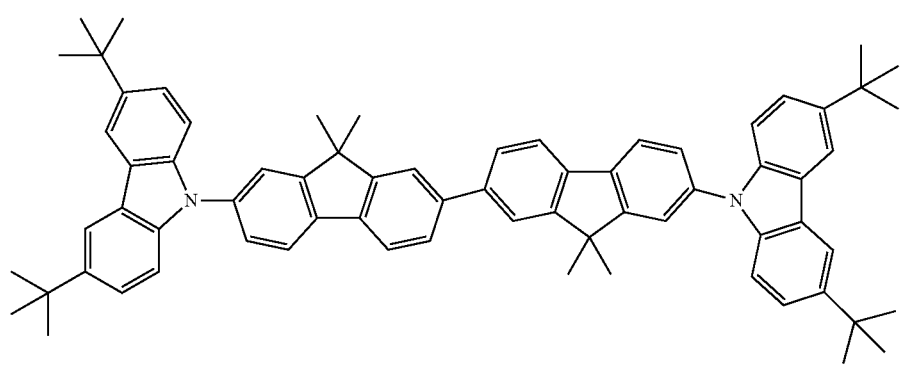

<Checking of Driving of Element (Measurement of Dark Current)>

Each of the obtained elements was checked so as to confirm whether the element functions as a photoelectric conversion element.

To the lower electrode and the upper electrode of each of the elements (Examples 1 to 30 and Comparative examples 1 and 2), voltage was applied such that an electric field intensity became $2.5 \times 10^5$ V/cm. As a result, in any of the elements, a dark current of equal to or lower than 100 nA/cm$^2$ was observed in a dark place, whereas a current of equal to or higher than 10 µA/cm$^2$ was observed in a bright place. Therefore, the photoelectric conversion element was confirmed to function.

<Evaluation of Photoelectric Conversion Efficiency (External Quantum Efficiency)>

Each of the obtained photoelectric conversion elements was evaluated in terms of photoelectric conversion efficiency.

First, voltage was applied to each photoelectric conversion element such that the electric field intensity became $2.0 \times 10^5$ V/cm. Thereafter, by irradiating the photoelectric conversion element with light from the side of the upper electrode (transparent conductive film), the external quantum efficiency at a maximum sensitivity wavelength was measured. The external quantum efficiency was measured by using a constant energy quantum efficiency measurement apparatus manufactured by OPTEL CORPORATION. The amount of light irradiated was 50 uW/cm$^2$. Furthermore, in order to eliminate the influence of light reflected from the surface of the photoelectric conversion element, the external quantum efficiency at the maximum sensitivity wavelength was divided by the absorbance of light at the maximum sensitivity wavelength, and the result was taken as the external quantum efficiency. The external quantum efficiency of each of the examples and comparative examples was determined as a relative value with respect to the external quantum efficiency of Comparative example 1 that was regarded as being 1.0. As the evaluation criteria, the external quantum efficiency of equal to or greater than 2.0 was rated as AA; the external quantum efficiency of equal to or greater than 1.5 and less than 2.0 was rated as A; the external quantum efficiency of equal to or greater than 1.2 and less than 1.5 was rated as B; the external quantum efficiency of equal to or greater than 0.8 and less than 1.2 was rated as C; and the external quantum efficiency of less than 0.8 was rated as D. The results are shown in Table 1. For practical use, the external quantum efficiency is preferably at least B, more preferably at least A, and particularly preferably at least AA.

<Evaluation of Response Speed (Responsiveness Evaluation)>

Each of the obtained photoelectric conversion elements was evaluated in terms of responsiveness.

Specifically, voltage was applied to each photoelectric conversion element such that the electric field intensity became $2.0 \times 10^5$ V/cm. Thereafter, by instantaneously lighting an LED, the photoelectric conversion element was irradiated with light from the side of the upper electrode (transparent conductive film). The photocurrent occurring at this time was measured by using an oscilloscope, and a rise time taken for the signal intensity to reach 95% from 0% was measured. The responsiveness of each of the examples and comparative examples was determined as a relative value with respect to the rise time of Comparative example 1 that was regarded as being 1.0. As the evaluation criteria, the response speed of less than 0.1 was rated as AA; the response speed of equal to or greater than 0.1 and less than 0.2 was rated as A; the response speed of equal to or greater than 0.2 and less than 0.5 was rated as B; the response speed of equal to or greater than 0.5 and less than 1.5 was rated as C; and the response speed of equal to or greater than 1.5 was rated as D. The results are shown in Table 1. For practical use, the response speed is preferably at least B, more preferably at least A, and particularly preferably at least AA.

<Dark Current at the Time when the Aforementioned Compound is Vapor-Deposited at 5.0 Å/sec>

In each of Examples 12 to 30 and Comparative examples 1 and 2, the photoelectric conversion element was prepared by setting a vapor deposition rate of the aforementioned compound to be 5.0 Å/sec, and a dark current thereof was evaluated. The value of the dark current was determined as a relative value with respect to a dark current of a photoelectric conversion element prepared at 2.6 Å/sec regarded as being 1.0. As the evaluation criteria, a value of a dark current of less than 1.5 was rated as AA; a value of a dark current of equal to or greater than 1.5 and less than 3.0 was rated as A; a value of a dark current of equal to or greater than 3.0 and less than 10 was rated as B; a value of a dark current of equal to or greater than 10 and less than 50 was rated as C; and a value of a dark current of equal to or greater than 50 was rated as D. For practical use, the value of the dark current is preferably at least B, more preferably at least A, and particularly preferably at least AA.

TABLE 1

| | Type of compound | Photoelectric conversion efficiency | Response speed | Dark current of compound vapor-deposited at 5.0 Å/sec |
|---|---|---|---|---|
| Example 1 | Compound 1 | B | A | — |
| Example 2 | Compound 2 | B | B | — |
| Example 3 | Compound 3 | B | B | — |
| Example 4 | Compound 4 | A | B | — |
| Example 5 | Compound 5 | B | B | — |
| Example 6 | Compound 6 | B | A | — |
| Example 7 | Compound 7 | B | B | — |
| Example 8 | Compound 8 | AA | B | — |
| Example 9 | Compound 9 | A | A | — |
| Example 10 | Compound 10 | A | A | — |
| Example 11 | Compound 11 | B | AA | — |
| Example 12 | Compound 12 | A | A | AA |
| Example 13 | Compound 13 | AA | AA | A |
| Example 14 | Compound 14 | AA | AA | AA |
| Example 15 | Compound 15 | AA | AA | A |
| Example 16 | Compound 16 | AA | AA | A |
| Example 17 | Compound 17 | AA | AA | A |
| Example 18 | Compound 18 | AA | AA | B |
| Example 19 | Compound 19 | A | AA | AA |
| Example 20 | Compound 20 | AA | AA | AA |
| Example 21 | Compound 21 | A | AA | AA |
| Example 22 | Compound 22 | AA | AA | AA |
| Example 23 | Compound 23 | AA | AA | AA |
| Example 24 | Compound 24 | A | AA | AA |
| Example 25 | Compound 25 | AA | AA | AA |
| Example 26 | Compound 26 | A | AA | B |
| Example 27 | Compound 27 | A | AA | AA |
| Example 28 | Compound 28 | A | AA | AA |
| Example 29 | Compound 29 | B | A | B |
| Example 30 | Compound 30 | A | A | AA |
| Comparative Example 1 | Comparative Compound 1 | C | C | D |
| Comparative Example 2 | Comparative Compound 2 | D | D | C |

As shown in Table 1, it was confirmed that the photoelectric conversion element of the present invention exhibits excellent heat resistance and responsiveness.

In particular, as shown in Examples 8 to 12, it was confirmed that in a case where at least one of $R^1$ and $R^2$ in General formulae (1) to (3) is represented by General formula (14) and n in General formulae (1) to (3) is 0, or in a case where $R^1$ and $R^2$ in General formulae (1) to (3) represent the same substituent, both the photoelectric conversion efficiency and the response speed are A, or at least one of the photoelectric conversion efficiency and the response speed is AA. That is, compared to Examples 1 to 7, it was confirmed that the effects are further improved.

As shown in Examples 13 to 16, it was confirmed that in a case where $R^1$ and $R^2$ in General formulae (1) to (3) are represented by General formula (14), n in General formulae (1) to (3) is 0, and $R^1$ and $R^2$ represent the same substituent, both the photoelectric conversion efficiency and the response speed are AA. That is, it was confirmed that the effects are further improved.

As shown in Examples 13 to 28, it was confirmed that in a case where $R^1$ and $R^2$ in General formulae (1) to (3) are represented by General formula (18), n in General formulae (1) to (3) is 0, and $R^1$ and $R^2$ represent the same substituent, the balance between the photoelectric conversion efficiency and the response speed is further improved.

From the comparison between Examples 6 and 10, it was confirmed that the effects are further improved when n=0.

From the comparison between Examples 17, 26, and 29, it was confirmed that in a case where $R^1$ and $R^2$ in General formulae (1) to (3) are represented by General formula (14), and each of $R^{30}$ and $R^{31}$ represents an aryl group which may have a substituent, the effects are further improved.

By comparing Examples 12 to 30 with each other, it was confirmed that in a case where $R^1$ and $R^2$ in General formulae (1) to (3) are represented by General formula (14), and $R^{30}$ to $R^{32}$ in General formula (14) form a ring by being linked to each other, the effect is further improved in the field "dark current at the time when the aforementioned compound is vapor-deposited at 5.0 Å/sec".

In contrast, in a case where the example compound 1 used in the example section of JP 2006-100767 A or the example compound 2 disclosed in JP 2011-253861 A was used (Comparative examples 1 and 2), the photoelectric conversion efficiency and the responsiveness were poor.

<Preparation of Imaging Device>

An imaging device in the same form shown in FIG. 2 was prepared. That is, on a CMOS substrate, amorphous TiN was formed into a film with a thickness of 30 nm by a sputtering method, and then patterning was performed by photolithography such that one pixel was formed on each photodiode (PD) on the CMOS substrate, thereby forming a lower electrode. Thereafter, the processes from the formation of a film of an electron blocking material were performed in the same manner as in Examples 1 to 30 and Comparative examples 1 and 2, thereby preparing an imaging device. The imaging device was also evaluated in the same manner as described above, and the same results as shown in Table 1 were obtained. Consequentially, it was revealed that the compounds are appropriate for manufacturing an imaging device and exhibit excellent performance.

What is claimed is:

1. A compound represented by General formula (17),

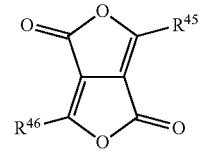

General formula (17)

in General formula (17), each of $R^{45}$ and $R^{46}$ independently represents an aryl group which may have a substituent or a heteroaryl group which may have a substituent, and at least one of $R^{45}$ and $R^{46}$ is a group represented by General formula (14),

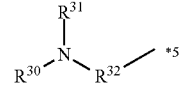

General formula (14)

in General formula (14), each of $R^{30}$ and $R^{31}$ independently represents an alkyl group, an aryl group which may have a substituent, or a heteroaryl group which may have a substituent; $R^{32}$ represents an arylene group which may have a substituent or a heteroarylene group which may have a substituent; $R^{30}$ and $R^{31}$, $R^{30}$ and $R^{32}$, or $R^{31}$ and $R^{32}$ form a ring by being directly bonded to each other or by being bonded to each other through a linking group; and *5 represents a bonding position, wherein each of $R^{30}$, $R^{31}$ and $R^{32}$ are directly bonded to the N.

2. The compound according to claim 1, wherein in General formulae (17), at least one of $R^{45}$ and $R^{46}$ is a group represented by General formula (18),

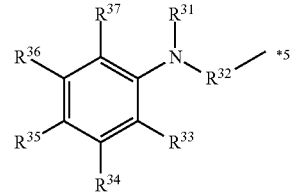

General formula (18)

in General formula (18), each of $R^{33}$ to $R^{37}$ independently represents a hydrogen atom or a substituent; $R^{32}$ represents an arylene group which may have a substituent or a heteroarylene group which may have a substituent; $R^{31}$ represents an alkyl group, an aryl group which may have a substituent, or a heteroaryl group which may have a substituent; $R^{33}$ and $R^{32}$, $R^{37}$ and $R^{31}$, or $R^{31}$ and $R^{32}$ form a ring by being directly bonded to each other or by being bonded to each other through a linking group; and *5 represents a bonding position.

3. The compound according to claim 1, wherein in General formulae (17), at least one of $R^{45}$ and $R^{46}$ is a group represented by General formula (15), General formula (15)

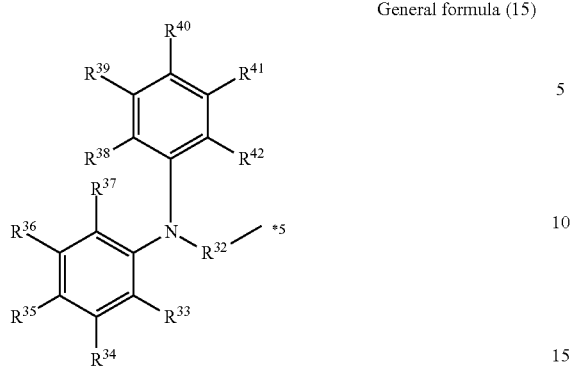

in General formula (15), each of $R^{33}$ to $R^{42}$ independently represents a hydrogen atom or a substituent; $R^{32}$ represents an arylene group which may have a substituent or a heteroarylene group which may have a substituent; $R^{37}$ and $R^{38}$, $R^{32}$ and $R^{33}$, and $R^{32}$ and $R^{42}$ form a ring by being directly bonded to each other or by being bonded to each other through a linking group; and *5 represents a bonding position.

* * * * *